United States Patent
Isogai et al.

(10) Patent No.: US 9,801,802 B2
(45) Date of Patent: Oct. 31, 2017

(54) VISCOUS COMPOSITION

(71) Applicant: DAI-ICHI KOGYO SEIYAKU CO., LTD., Kyoto-shi, Kyoto (JP)

(72) Inventors: Akira Isogai, Tokyo (JP); Hideyuki Sumi, Kyoto (JP); Yousuke Goi, Kyoto (JP)

(73) Assignee: DAI-ICHI KOGYO SEIYAKU CO., LTD., Kyoto (JP)

( * ) Notice: Subject to any disclaimer, the term of this patent is extended or adjusted under 35 U.S.C. 154(b) by 0 days.

(21) Appl. No.: 14/950,573

(22) Filed: Nov. 24, 2015

(65) Prior Publication Data

US 2016/0074305 A1    Mar. 17, 2016

Related U.S. Application Data

(62) Division of application No. 13/574,264, filed as application No. PCT/JP2010/050800 on Jan. 22, 2010, now Pat. No. 9,248,090.

(51) Int. Cl.

| | | |
|---|---|---|
| *A61K 47/38* | (2006.01) |
| *C08B 15/00* | (2006.01) |
| *A61Q 19/00* | (2006.01) |
| *A61K 8/73* | (2006.01) |
| *A61K 8/92* | (2006.01) |
| *A61K 8/02* | (2006.01) |
| *A61K 8/04* | (2006.01) |
| *C08B 15/02* | (2006.01) |
| *A01N 25/04* | (2006.01) |
| *A01N 37/40* | (2006.01) |
| *A61K 8/19* | (2006.01) |
| *A61K 8/29* | (2006.01) |
| *A61K 8/31* | (2006.01) |
| *A61K 8/34* | (2006.01) |
| *A61K 8/37* | (2006.01) |
| *A61K 8/86* | (2006.01) |
| *A61K 8/891* | (2006.01) |
| *A61Q 13/00* | (2006.01) |
| *A61Q 15/00* | (2006.01) |
| *A61Q 19/10* | (2006.01) |

(52) U.S. Cl.

CPC ............ *A61K 8/731* (2013.01); *A01N 25/04* (2013.01); *A01N 37/40* (2013.01); *A61K 8/027* (2013.01); *A61K 8/042* (2013.01); *A61K 8/046* (2013.01); *A61K 8/19* (2013.01); *A61K 8/29* (2013.01); *A61K 8/31* (2013.01); *A61K 8/34* (2013.01); *A61K 8/345* (2013.01); *A61K 8/37* (2013.01); *A61K 8/73* (2013.01); *A61K 8/86* (2013.01); *A61K 8/891* (2013.01); *A61K 8/92* (2013.01); *A61K 8/922* (2013.01); *A61K 47/38* (2013.01); *A61Q 13/00* (2013.01); *A61Q 15/00* (2013.01); *A61Q 19/00* (2013.01); *A61Q 19/007* (2013.01); *C08B 15/02* (2013.01); *A61K 2800/10* (2013.01); *A61K 2800/413* (2013.01); *A61K 2800/48* (2013.01); *A61K 2800/54* (2013.01); *A61Q 19/10* (2013.01)

(58) Field of Classification Search

CPC C08B 15/00; C08L 1/02; A01N 25/04; A61K 2800/10; A61K 47/38; A61K 8/027; A61K 8/042; A61Q 19/00

See application file for complete search history.

(56) References Cited

U.S. PATENT DOCUMENTS

| 5,039,519 | A | 8/1991 | Inoue et al. |
| 5,780,618 | A | 7/1998 | Banker et al. |
| 6,599,999 | B1 * | 7/2003 | Chandran ............... A61K 8/817 424/70.11 |
| 2007/0196401 | A1 | 8/2007 | Naruse et al. |
| 2008/0138300 | A2 | 6/2008 | Yu et al. |

FOREIGN PATENT DOCUMENTS

| CN | 1281469 | 1/2001 |
| EP | 1036799 | 9/2000 |
| EP | 1577361 | 9/2005 |

(Continued)

OTHER PUBLICATIONS

Extended European Search Report dated Nov. 2, 2015 in corresponding European Application No. 10843875.5.

(Continued)

*Primary Examiner* — Tracy Liu

(74) *Attorney, Agent, or Firm* — Wenderoth, Lind & Ponack, L.L.P.

(57) ABSTRACT

A viscous composition of the present invention comprises specific cellulose fibers (A), (A') and (A") and the specific cellulose fibers (A), (A') and (A") are used with appropriate selection according to uses of a cosmetic composition, a gel-like composition and a spray composition. Therefore, in case where the composition is used as the cosmetic composition, a cosmetic composition which is excellent in shape retention ability and dispersion stability and excellent in water tolerance to satisfy the properties and the performance which is necessary for cosmetics is obtained. Additionally, in case where the composition is used as a gel-like composition, gel-state can be kept without separation or water release. Furthermore, in case where the composition is used as a spray composition, since it is possible to time-dependently keep stable gel state even if functional additives such as electrolytes, ionic substances, etc. are contained, it is possible to mix various functional additives which is necessary for the use without any problem.

4 Claims, No Drawings

(56) References Cited

FOREIGN PATENT DOCUMENTS

| | | |
|---|---|---|
| EP | 2 216 345 | 8/2010 |
| GB | 2066145 | 7/1981 |
| JP | 56-100801 | 8/1981 |
| JP | 5-32519 | 2/1993 |
| JP | 7-101851 | 4/1995 |
| JP | 9-165323 | 6/1997 |
| JP | 9-241115 | 9/1997 |
| JP | 11-116427 | 4/1999 |
| JP | 2000-309503 | 1/2000 |
| JP | 2000-51682 | 2/2000 |
| JP | 2000-319117 | 11/2000 |
| JP | 2001-89359 | 4/2001 |
| JP | 2002-255741 | 9/2002 |
| JP | 2003-73229 | 3/2003 |
| JP | 2003-137729 | 5/2003 |
| JP | 2003-180812 | 7/2003 |
| JP | 2003-252903 | 9/2003 |
| JP | 2006-321760 | 11/2006 |
| JP | 2007-91618 | 4/2007 |
| JP | 2007-169413 | 7/2007 |
| JP | 2007-291192 | 11/2007 |
| JP | 2008-1728 | 1/2008 |
| JP | 2008001728 A * | 1/2008 |
| JP | 2008-308802 | 12/2008 |
| JP | 2009-161723 | 7/2009 |
| JP | 2009-161893 | 7/2009 |
| JP | 2009-242991 | 10/2009 |
| JP | 2010-37199 | 2/2010 |
| JP | 2010-37200 | 2/2010 |
| JP | 2010-37348 | 2/2010 |
| WO | 2004/061043 | 7/2004 |
| WO | 2009/069641 | 6/2009 |

OTHER PUBLICATIONS

Saito et al., "Cellulose Nanofibers Prepared by TEMPO-Mediated Oxidation of Native Cellulose", *American Chemical Society*, 2007, vol. 8, No. 8, pp. 2485-2491.
Kamel, S. et al., Pharmaceutical significance of cellulose: A review, eXPRESS Polymer Letters, vol. 2, No. 11 (2008) 758-778.
Korean Office Action, dated Jan. 24, 2014, from the Korean Patent Office in corresponding Korean Application No. 10-2012-7019510, and English translation.
Chinese Office Action dated Feb. 27, 2013, from the Chinese Patent Office in corresponding Chinese Application No. 201080062120, and English translation.
Notification of Reasons for Refusal dated Feb. 12, 2013, from the Japanese Patent Office in corresponding Japanese Application No. 2008-197848, and English translation.
Notification of Reasons for Refusal dated Feb. 12, 2013, from the Japanese Patent Office in corresponding Japanese Application No. 2008-197849, and English translation.
Saito, T., et al. Homogeneous Suspensions of Individualized Microfibrils from TEMPO-Catalyzed Oxidation of Native Cellulose. Biomacromolecules 7(6):1687-1691(2006).
Notification of Reasons for Refusal, dated Sep. 10, 2012, issuing in counterpart Japanese Appln. No. 2008-197847.
International Search Report for PCT/JP2010/050800, dated Apr. 6, 2010.
Royal Society of Chemistry. Surfactants: the ubiquitous amphiphiles. Jul. 2003. pp. 1-8.
CSC Scientific Company, Inc. How does surface tension relate to viscosity? Jan. 17, 2011. pp. 1-2.
FDA. Is it a Cosmetic, a Drug, or Both? (Or is it Soap?). Jul. 8, 2002. pp. 1-5.

* cited by examiner

VISCOUS COMPOSITION

TECHNICAL FIELD

The present invention relates to a viscous composition including cellulose fibers.

BACKGROUND ART

As a viscous composition, there are mentioned a cosmetic composition for use for various cosmetics and others; a gel-type composition for use for promotion of viscosity increase or for gelation; and further a spray composition for use for spray nebulization, etc.

Heretofore, for cream-type, gel-type, emulsion-type or liquid-type cosmetic materials, a composition is used wherein a polymer material or the like is mixed with a dispersant medium such as water, alcohol, oil or the like. The polymer material is used for the purpose of imparting shape retention performance (shape retention capability) for maintaining viscosity increase and dispersion stability, and for example, water-soluble cellulose derivatives such as methyl cellulose, carboxymethyl cellulose salt, etc.; synthetic polymers such as polyvinyl alcohol, polyvinyl pyrrolidone, carboxyvinyl polymer, polyethylene glycol, etc.; natural polymer polysaccharides such as quince seed, bee gum, xanthane gum, hyaluronic acid salt, etc. are used. Most of these polymer materials are soluble in water, and are therefore stringy and are not felt good to use, and many of them have poor salt tolerance.

In the background, a cosmetic composition not having the feeling in use specific to water-soluble polymer but excellent in dispersion stability is desired. For the cosmetic composition of the type, for example, a cosmetic composition which includes cellulose particles prepared through hydrolysis and physical grinding of natural cellulose without regeneration (Patent Reference 1) is proposed. This is a composition in which the fat fraction is lowered than in conventional cosmetic compositions and which can attain creamy or emulsion-like properties. However, since it contains coarse grains having a large grain size, the dispersiveness thereof is insufficient to cause a rough feel of the composition.

As a technique of highly dispersing cellulose, a method for producing microfibrillar cellulose by processing an aqueous suspension of pulp with a high-pressure homogenizer to grind it to a microfibril level t is proposed (Patent Reference 2). Since the high-degree dispersion of cellulose to be obtained according to the production method must be processed by the use of an extremely large quantity of energy and the degree of dispersion thereof is insufficient, it is impossible to erase the rough feel specific to the dispersion. Furthermore, the conventional microfibrillated cellulose dispersions are all white and nontransparent, and therefore have a problem in that they could not be applied to cosmetic materials required to be transparent.

To solve the problem, a cosmetic composition that includes cellulose microfibrillated in nanosize is proposed (Patent Reference 3). However, those described in the patent publications are still insufficient for solving the above-mentioned problems, as described below.

On the other hand, as a tackifier and a gelling agent, natural polymer compounds such as Jerangam, carrageenan, agar, xanthan gum, etc.; nonionic water-soluble celluloses such as methyl cellulose, hydroxylmethyl cellulose, etc.; ionic celluloses such as carboxymethyl cellulose, cationized cellulose, etc.; synthetic polymers such as polyvinyl alcohol, polyvinyl pyrrolidone, sodium polyacrylate, carboxyvinyl polymer, polyethylene glycol, etc.; water-swellable clay minerals such as smectite, etc are conventionally used.

However, since the above-mentioned natural polymer compounds are poorly soluble in water, heat treatment of water in the process of producing gel-type compositions is required and consequently have a problem of poor producibility. Additionally, there is another problem that when fragrance or the like is added thereto, a part of the added fragrance or the like may evaporate away. On the other hand, since the above-mentioned nonionic water-soluble celluloses have high solubility in water, heat treatment of water is not necessary. However, for obtaining gel-type compositions, there is a problem in that a large quantity of the water-soluble cellulose must be added. In addition, the above-mentioned synthetic polymers such as sodium polyacrylate, carboxyvinyl polymer and the like are troublesome in that a special attention must be paid thereto so as not to form unmixed-in lumps in dispersing and dissolving them and that they require pH control. It is disclosed that the above-mentioned xanthan gum is stringy and, in use for cosmetics and the like, it causes a sticky feeling (Non-Patent Reference 1). Most of these natural polymer compounds, water-soluble celluloses and synthetic polymers have many problems in point of the range of use and the designability thereof in that their viscosity greatly lowers depending on co-existing salts and they are stringy.

In the situation, a nasal gel using a carboxyvinyl polymer as the gelling agent therein has been proposed, and it is disclosed that the gel has been improved to prevent dripping and has an effect of promoting the absorbability of the pharmaceutical ingredient therein (Patent Reference 4). In addition, it is disclosed that cellulose particles downsized to a few 10 nm have high transparency and can show high performance of thickening, dispersion and emulsion stabilization and structure stabilization even when a small amount thereof is added (Patent Reference 5). However, those described in these patent references are still unsatisfactory for solving the above-mentioned problems, as described below.

In general, spray products are used as products in a broad field of hair-care products, skincare products, aromatic substances, detergents, various coating agents, agricultural chemicals and others. Many spray products are commercialized by charging a liquid composition in a spray apparatus. The properties necessary for spray products are that they can be sprayed by using ordinary spray containers under broad environmental condition (temperature, humidity, etc.); that the sprayed droplets could have a suitable size depending on the intended use and are free from spraying unevenness; and that they are also free from dripping when sprayed onto vertical faces or inclined faces.

Recently, a lot of sprayable gel-type compositions have been proposed (see Patent References 6 to 9). These sprayable gel-type compositions have excellent characteristics in that they are free from a trouble of dripping when they are sprayed on vertical faces or inclined faces.

For example, in Patent Reference 6, a gel-type mist cosmetic product using a clay mineral, smectite is proposed. In Patent Reference 7, a gel-type composition for spray, also using a clay mineral, hectorite is proposed. Since these clay minerals are in the form of extremely small particles, they can swell with water or with any other solvent and disperse thereinto to form a sol/gel. Since the dispersion of the clay mineral has thixotropy, when a pressure (force) on a certain level or more is given, it liquefies, while when released from the pressure (force), it immediately change into gels. Using the property specific to the clay mineral, the above-mentioned composition for spray may be combined with a spray container, to enable spraying the composition without the trouble by dripping.

In Patent Reference 8, an aerosol composition which is for mist-like spraying of an aqueous liquid concentrate having a high viscosity for uniform adhesion with no dripping is proposed. In the aqueous liquid concentrate, a cellulosic thickener and a crosslinked acrylic thickener are used. In case of these thickeners, stringiness is not shown even in a high viscosity and show high-level thixotropy. Therefore they can be excellent gel-type spray compositions.

In Patent Reference 9, a composition for spray agent, which includes cellulose fine particles having a mean degree of polymerization (DP) of 100 or less, a fraction of cellulose I-type crystal component of 0.1 or less, a fraction of cellulose II-type crystal component of 0.4 or less and a mean particle size of 2 μm or less, and a liquid dispersion medium, wherein the cellulose concentration is from 0.1 to 5.0% by weight and on the viscosity-shear stress curve of the composition, which is measured with a cone-plate type rotatory viscometer at 25° C. in a shear rate region including at least from $1\times10^{-3}$ $S^{-1}$ to $1\times10^2$ $S^{-1}$, the maximum value of the viscosity ($\eta_{max}$) is $\eta_{max} \geq 1\times10^3$ mPa·s. The cellulose fine particles used in the spray composition can be obtained through acid hydrolysis of natural cellulose or regenerated cellulose. The spray composition including the above-mentioned cellulose particles is transparent in an aqueous medium and have excellent properties in that its mother droplets can well fix on the sprayed surface with little spraying unevenness and the sprayed mother droplets are free from a trouble of dripping on vertical faces and inclined faces. However, those described in these patent publications are still unsatisfactory for solving the above-mentioned problems, as described below.

RELATED ART REFERENCES

Patent References

Patent Reference 1: JP-A-5-32519
Patent Reference 2: JP-A-56-100801
Patent Reference 3: JP-A-2000-26229
Patent Reference 4: JP-A-2001-89359
Patent Reference 5: WO99/28350
Patent Reference 6: JP-A-9-241115
Patent Reference 7: JP-A-2000-51682
Patent Reference 8: JP-A-2006-321760
Patent Reference 9: JP-A-2003-73229

Non-Patent Reference

Non-Patent Reference 1: "Newest Trend of Polymer Gel", supervised by Mitsuhiro Shibayama and Kanji Kajiwara, published by CMC Publishing, Apr. 30, 2004, pp. 216-226

SUMMARY OF THE INVENTION

Problems to be Solved by the Invention

Of the above-mentioned patent publications relating to cosmetic compositions, since one described in the newest the Patent Publication 3 includes nanoparticulated cellulose fine particles, it gives a good feel in use with neither sticky feeling nor rough feeling. However, since the production of the cellulose fine particles requires a large quantity of sulfuric acid, there are problems in view of the environmental load and the workability. In addition, since the dispersion of cellulose fine particles has poor salt tolerance, there is an another problem in that its application field is greatly limited.

As in the above, in conventional techniques, various problems that sufficient performance as materials for cosmetics cannot be obtained such as that the degree of dispersiveness is insufficient; the rough feeling of dispersions could not be overcome; and the salt tolerance of dispersions is poor and the application range thereof is therefore limited.

Of the Patent References 4 and 5 relating to conventional thickeners and gelling agents, those described in the Patent Reference 4 have difficulties in production such as that it requires pH control with a basic substance in their preparation and requires strong stirring for uniform mixing and dispersion of pharmaceutical ingredients in high-viscosity base material. The cellulose particles described in Patent Reference 5 have difficulties such that their viscosity lowers in the co-presence of an electrolyte such as salts or a high-concentration ionic surfactant and that, in addition, the cellulose particles settle out and could not take a form of dispersion as a recult.

Of the Patent References 6 to 8 relating to spray compositions, the dispersion of the spray compositions described in the Patent Reference 6 and the Patent Reference 7 are nontransparent owing to the clay minerals dispersed therein, and in addition, they are colored specifically to the clay minerals. Therefore, the spray compositions are problematic in that they could not be used for applications that require transparency. Another problem with them is that, when the sprayed coating film is dried, it often forms powder on the surface thereof. Still another problem is that, when an alcohol exists in the solvent, the clay mineral may aggregate to greatly worsen the spray properties (spraying performance).

In the spray composition of the Patent Reference 8, since the function of the thickener (especially, crosslinked acrylic thickener) worsens in the co-presence of an electrolyte or the like salt or an ionic substance, the viscosity of the composition greatly lowers. Consequently, in case where it is used as a spray composition that requires a viscosity, there is a problem that the functional additives (electrolyte, ionic substance, etc.) which can be incorporated therein are limited.

In the spray composition of Patent Reference 9, in case where an ionic substance such as an anionic surfactant, an inorganic salt, a carboxymethyl cellulose or the like is incorporated, even when the amount thereof added is small, the hydration of the cellulose particles would be inhibited to cause coagulation and precipitation of the particles. In general, various functional additives such as ionic substance and others are mixed in a spray composition. However, the cellulose fine particles described in the Patent Reference 9 are problematic in that the functional additives capable of being added thereto are limited for the reasons mentioned above.

As in the above, the sprayable gel compositions which is conventionally proposed in the art have, in summary, the following problems (1) and (2):

(1) The applicable use and object are limited, and when the sprayed coating film is dried, it may form a powder on the surface thereof.

(2) In the co-presence of an ionic substance, an electrolyte or the like, the viscosity greatly lowers and the compositions could not keep a gel state, or the thickener itself may aggregate or settle out.

In the situation as above, an object of the present invention is to provide a viscous composition which is useful as a cosmetic composition excellent in shape retention ability, dispersion stability and salt tolerance; to provide a viscous composition which is useful as a gel-type composition capable of maintaining the high viscosity thereof even in the co-presence of a salt, an ionic surfactant or the like; and to provide a viscous composition which is useful as a spray composition of which the viscosity does not lower even in the co-presence of a functional additive such as an electrolyte, an ionic substance or the like and which can therefore maintain a stable gel state and can be sprayed.

Means for Solving the Problems

For achieving the above-mentioned object, the first aspect of the viscous composition of the present invention has a constitution including one component selected from the following components (A), (A') and (A"), and the component (B):

(A) cellulose fibers having a maximum fiber diameter of 1000 nm or less and a number-average fiber diameter of from 2 to 100 nm, wherein the cellulose has a cellulose I-type crystal structure; the hydroxyl group at the C6-position of the glucose unit in the cellulose molecule is selectively oxidized and modified into an aldehyde group and a carboxyl group; and the amount of the carboxyl group is from 0.6 to 2.2 mmol/g, (A') cellulose fibers having a maximum fiber diameter of 1000 nm or less and a number-average fiber diameter of from 2 to 150 nm, wherein the cellulose has a cellulose I-type crystal structure; the hydroxyl group at the C6-position of the glucose unit in the cellulose molecule is selectively oxidized and modified into an aldehyde group and a carboxyl group; and the amount of the aldehyde group is from 0.08 to 0.3 mmol/g and the amount of the carboxyl group is from 0.6 to 2.0 mmol/g, (A") cellulose fibers having a maximum fiber diameter of 1000 nm or less and a number-average fiber diameter of from 2 to 150 nm, wherein the cellulose has a cellulose I-type crystal structure; the hydroxyl group at the C6-position of the glucose unit in the cellulose molecule is selectively oxidized and modified into an aldehyde group and a carboxyl group; and the amount of the carboxyl group is from 0.6 to 2.0 mmol/g, and the amount of the aldehyde group is from 0.05 to 0.3 mmol/g, (B) water.

The second aspect of the present invention is a cosmetic composition of the viscous composition of the first aspect of the present invention, comprising the following components (B) and (C) in addition to the following component (A):

(A) cellulose fibers having a maximum fiber diameter of 1000 nm or less and a number-average fiber diameter of from 2 to 100 nm, wherein the cellulose has a cellulose I-type crystal structure; the hydroxyl group at the C6-position of the glucose unit in the cellulose molecule is selectively oxidized and modified into an aldehyde group and a carboxyl group; and the amount of the carboxyl group is from 0.6 to 2.2 mmol/g, (B) water, (C) a functional additive.

The third aspect of the present invention is a gel-type composition of the viscous composition of the first aspect of the present invention, comprising the following component (B) in addition to the following component (A'), wherein the blend ratio of the component (A') falls within a range of from 0.3 to 5.0% by weight of the entire gel-type composition.

(A') cellulose fibers having a maximum fiber diameter of 1000 nm or less and a number-average fiber diameter of from 2 to 150 nm, wherein the cellulose has a cellulose I-type crystal structure; the hydroxyl group at the C6-position of the glucose unit in the cellulose molecule is selectively oxidized and modified into an aldehyde group and a carboxyl group; and the amount of the aldehyde group is from 0.08 to 0.3 mmol/g, and the amount of the carboxyl group is from 0.6 to 2.0 mmol/g, (B) water.

The fourth aspect of the present invention is a spray composition of the viscous composition of the first aspect of the present invention, which comprises the following component (B) in addition to the component (A"), and wherein the content of the cellulose fibers of the component (A") is within a range of from 0.1 to 3.0% by weight; the maximum value of the viscosity ($\eta_{max}$) of the composition, which is measured with a cone-plate type rotatory viscometer at 20° C. in a shear rate region including from $1\times10^{-3}$ $S^{-1}$ to $1\times10^{3}$ $S^{-1}$, is $\eta_{max} \geq 1\times10^{4}$ mPa·s; and the minimum value of the viscosity ($\eta_{min}$) thereof is $\eta_{min} \leq 1\times10^{2}$ mPa·s:

(A") cellulose fibers having a maximum fiber diameter of 1000 nm or less and a number-average fiber diameter of from 2 to 150 nm, wherein the cellulose has a cellulose I-type crystal structure; the hydroxyl group at the C6-position of the glucose unit in the cellulose molecule is selectively oxidized and modified into an aldehyde group and a carboxyl group; and the amount of the carboxyl group is from 0.6 to 2.0 mmol/g, and the amount of the aldehyde group is from 0.05 to 0.3 mmol/g, (B) water.

BACKGROUND TO THE INVENTION

The inventors of the present invention made a series of studies for the purpose of finding out cellulose fibers useful for use in the above-mentioned cosmetics, thickeners and gelling agents, sprays, etc. Among them, the inventors made assiduous studies many times for obtaining a cosmetic composition excellent in shape retention ability, dispersion stability and salt tolerance. In the process of the studies, the inventors have reached fine cellulose fibers (A) having a maximum fiber diameter of 1000 nm or less and a number-average fiber diameter of from 2 to 100 nm, wherein the cellulose has a cellulose I-type crystal structure; the hydroxyl group at the C6-position of the glucose unit in the cellulose molecule is selectively oxidized and modified into an aldehyde group and a carboxyl group; and the amount of the carboxyl group is from 0.6 to 2.2 mmol/g. Using a dispersion prepared by dispersing the specific fine cellulose fibers in a liquid dispersion medium, water, the inventors have found that a viscous composition useful as a cosmetic composition excellent in shape retention ability, dispersion stability and salt tolerance can be obtained.

In addition, the inventors made assiduous studies further many times for obtaining a viscous composition especially useful as a gel-type composition capable of maintaining a high viscosity even in the co-presence of a salt, an ionic surfactant or the like. In the process of the studies, the inventors have specifically noted fine cellulose fibers having a maximum fiber diameter of 1000 nm or less and a number-average fiber diameter of from 2 to 150 nm, wherein the cellulose has a cellulose I-type crystal structure, the hydroxyl group at the C6-position of the glucose unit in the cellulose molecule is selectively oxidized and modified into an aldehyde group and a carboxyl group. With that, the inventors have reached a gel-type composition by combining the specific fine cellulose fibers, in which the amount of the aldehyde group is from 0.08 to 0.3 mmol/g and that of the carboxyl group is from 0.6 to 2.0 mmol/g (water-insoluble cellulose fibers) (A″), and a liquid dispersion medium, water. The inventors made experiments many times relating to the preferable content of the specific cellulose fibers in the gel-type composition, and have found that, when the content of the specific cellulose fibers falls within a range of from 0.3 to 5.0% by weight of the entire gel-type composition, the composition can attain the intended object.

Further, the inventors recalled use of the special fine cellulose fibers that the inventors had developed as the material for a spray composition as a type of the viscous composition for material for a spray composition. The fine cellulose fibers (A″) have a maximum fiber diameter of 1000 nm or less and a number-average fiber diameter of from 2 to 150 nm, and when it is dispersed in a dispersion medium, water, they form a transparent gel while maintaining flowability without forming flocculates of cellulose fibers therein. However, they are sprayed, they immediately liquefy owing to the spraying pressure, and can be well sprayed to a subject to coat it. In addition, the cellulose is in the form of surface-oxidized microtine fibers of a naturally-derived cellulose solid material having an I-type crystal structure; and shows features that the sprayed mother liquid droplets to coat the subject can again gel; its fixity is good; and it is free from spraying unevenness and from a trouble of dripping of the mother droplets thereof on vertical faces or inclines faces. Furthermore, the inventors have found that a part of the hydroxyl group of the cellulose (the hydroxyl group at the C6-position of the glucose unit in the cellulose molecule) is, through selective oxidation thereof, modified into a functional group such as a carboxyl group and an aldehyde group and the amount of the functional group is defined to fall within a specific range. Therefore, even when a small amount of the cellulose is added, the resulting composition can be highly thickened and can efficiently maintain the gel state thereof, and at the same time, even in the co-presence of an electrolyte or an ionic substance, the composition does not cause separation or water release and can well keep the gel state thereof having a high viscosity, and can therefore attain the intended object.

Effect of the Invention

As in the above, the viscous composition of the present invention includes the above-mentioned special cellulose fibers (A), (A′) or (A″). For use as a cosmetic composition, the cellulose fibers of the above component (A) are combined with water (B) and the functional additive (C) such as a water-releasing material or the like to give a cosmetic composition which is excellent in shape retention ability and dispersion stability and excellent in water tolerance to satisfy the properties and the performance which is necessary for cosmetics. Since the specific cellulose fibers (A) are extremely fine, the composition provides an excellent feeling in use for when application to skin, with neither sticky feeling nor rough feeling. In addition, the cosmetic composition is free from viscosity decrease even at a high temperature of 50° C. or more, and is excellent in temperature stability.

Furthermore, since the cellulose fibers in which the hydroxyl group at the C6 position of the glucose unit on the surface of the cellulose fibers is selectively oxidized into an aldehyde group and a carboxyl group are used therein, the cosmetic composition can easily provide surface smoothness which conventional cellulose fine particles could not provide, and is free from a feeling of stickiness which is specific to water-soluble polymers. In addition, the cosmetic composition containing salts here can be thickened and the dispersion stability thereof can be obtained which are difficult in the conventional cases containing cellulose fine particles and a water-soluble polymer and salt tolerance is to enhance salt tolerance is enhances as a result.

In case where the cellulose fibers of the component (A) are such that a part of the hydroxyl group of the cellulose fibers is oxidized with a co-oxidizing agent in the co-presence of an N-oxyl compound such as 2,2,6,6-tetramethylpiperidine (TEMPO) or the like, the cellulose fibers may be easily processed to give microfine fibers having a number-average fiber diameter of rom 2 to 100 nm to facilitate the production of the cosmetic composition.

In case where the viscous composition of the present invention is used as a gel-type composition, the cellulose fibers (A′) of the above-mentioned special cellulose fibers are combined with (B) water. In the gel-type composition including the components, the content of the fine cellulose fibers (A′) falls within a range of from 0.3 to 5.0% by weight of the entire gel-type composition. Therefore, even in the co-presence of a salt, an ionic surfactant or the like, the composition can maintain the gel state thereof without separation or water release. In addition, the gel-type composition of the present invention is easy to use, since it is not stringy and is easily mixed with various types of functional additives.

In addition, since the gel-type composition can sufficiently keep the viscosity thereof even in high-temperature environments, it is usable, for example, for in-car applications to be used at high in-car temperatures of 70° C. or more (aromatic substances, deodorants, air refreshers, etc. for automobiles). On the other hand, since natural polysaccharide gelling agents such as gelatin, agarose and others undergo sol-gel transition at high temperatures and could not keep the viscosity as gel, they are unsuitable for such applications.

The gel-type composition including the specific cellulose fibers and water (liquid dispersion medium) is well miscible with functional additives such as inorganic salts, surfactants and the like, and can be widely favorably used as a gel substrate for toiletry goods such as aromatic substances, etc.

In the cellulose fibers of the component (A′), when a part of the hydroxyl group is oxidized with a co-oxidizing agent in the co-presence of an N-oxyl compound into a carboxyl group and an aldehyde group and when the amount to be used of the co-oxidizing agent and the time for oxidation are controlled, then the oxidized and modified functional groups may be controlled to fall within a specific range. Therefore the resulting gel-type composition can exhibit better results.

In case where the viscous composition of the present invention is used as a spray composition, the special cellulose fibers of (A″) are combined with (B) water. The spray composition including these components can maintain a stable gel state with time even if functional additives such as electrolytes, ionic substances and the like are contained. Consequently, various functional additives necessary for the use of the composition can be mixed in the composition with no trouble. The spray composition composed of the indispensable components alone is transparent and, when it is sprayed, it can be immediately liquefied owing to the spraying pressure, and can be well sprayed on a subject to coat it. The mother liquid droplets thus sprayed for coating can again gel and its fixity is good with little spraying unevenness, and the mother liquid droplets are free from a trouble of dripping on vertical faces or inclined faces. The coating film formed of the spray composition does not form a powder on the surface thereof, after drying.

In the spray composition, since the content of the special cellulose fibers is from 0.1 to 3.0% by weight, and the maximum value of the viscosity ($\eta_{max}$) of the composition, which is measured with a cone-plate type rotatory viscometer at 20° C. in a shear rate region including from $1 \times 10^{-3}$ $S^{-1}$ to $1 \times 10^3$ $S^{-1}$, is $\eta_{max} \geq 1 \times 10^4$ mPa·s, the composition enables good spray coating with no dripping. In addition, since the minimum value of the viscosity ($\eta_{min}$) of the composition is $\eta_{min} \leq 1 \times 10^2$ mPa·s, the composition can be sprayed as fine mother liquid droplets with no spraying unevenness.

In case where the special cellulose fibers (A") are oxidized with a co-oxidizing agent in the presence of an N-oxyl compound, the amount of the carboxyl group and the amount of the aldehyde group in the cellulose fibers can be readily controlled to fall within a suitable range, and better results can be obtained as the spray composition.

The spray atomizer charged with the spray composition can more effectively exhibit the effects which is specific to the spray composition of the present invention.

MODE FOR CARRYING OUT THE INVENTION

Next, the viscous composition of the present invention is described specifically in individual sections of the cosmetic composition, the gel-type composition and the spray composition.

[Cosmetic Composition]

The embodiment of the cosmetic composition is firstly described in detail.

The cosmetic composition of the present invention includes specific cellulose fibers (component A), water (component B) and a functional additive (component C).

The cosmetic composition of the present invention is characterized by using fine cellulose fibers (component A) that have a maximum fiber diameter of 1000 nm or less and a number-average fiber diameter of from 2 to 100 nm, wherein the cellulose has a cellulose I-type crystal structure, the hydroxyl group at the C6-position of the glucose unit in the cellulose molecule is selectively oxidized and modified into an aldehyde group and a carboxyl group, and the amount of the carboxyl group is from 0.6 to 2.2 mmol/g. This means that the cellulose fibers are surface-oxidized microfibrillated fibers of a naturally-derived cellulose solid material having an I-type crystal structure. Specifically, in a process of biosynthesis of natural cellulose, nanofibers called microfibrils are firstly formed almost unexceptionally, and these are multi-bundled to give a high-order solid structure. However, for attenuating the hydrogen bonding between the surfaces of the microfibrils, which serves as a locomotive for the strong aggregation force between these microfibrils, a part of the hydroxyl group is oxidized and converted into an aldehyde group and a carboxyl group.

In this connection, the fact the cellulose to constitute the specific cellulose fibers (component A) has an I-type crystal structure can be identified, for example, by the typical peaks appearing at two positions near 2θ=14 to 17° and near 2θ=22 to 23° in the diffraction profile in wide-angle X-ray diffractiometry thereof The specific cellulose fibers (component A) have a maximum fiber diameter of 1000 nm or less and a number-average fiber diameter of from 2 to 100 nm, and from the viewpoint of dispersion stability thereof, preferably having a number-average fiber diameter of from 3 to 80 nm. Specifically, when the number-average fiber diameter is less than 2 nm, then the fibers inherently dissolve in the dispersion medium, but on the contrary, when number-average fiber diameter is more than 100 nm, then the cellulose fibers would settle out and therefore could not express the functionality to be attained by incorporation of the cellulose fibers. Similarly, when the maximum fiber diameter is more than 1000 nm, the cellulose fibers would settle out. Therefore, the functionality to be attained by incorporation of the cellulose fibers cannot be obtained.

The number-average fiber diameter and the maximum fiber diameter of the specific cellulose fibers (component A) can be measured, for example, as follows: specifically, water is added to the cellulose fibers to prepare a mixture having a cellulose solid content of 1% by weight. This is dispersed, using an ultrasonic homogenizer, a high-pressure homogenizer, a blender having a power of revolution speed of at least 15,000 rpm or the like, and then freeze-dried to prepare a sample. This is observed with a scanning electronic microscope (SEM) or the like, and the number-average fiber diameter and the maximum diameter of the cellulose fibers can be measured and calculated by the obtained image.

In the specific cellulose fibers (component A), the hydroxyl group at the C6 position of the glucose unit in the cellulose molecule is selectively oxidized and modified into an aldehyde group and a carboxyl group, and the amount of the carboxyl group is from 0.6 to 2.2 mmol/g. Furthermore, from the viewpoint of the shape retention capability and the dispersion stability, the amount is especially preferably within a range of from 0.6 to 2.0 mmol/g. Specifically, when the amount of the carboxyl group is less than 0.6 mmol/g, then the dispersion stability of the cellulose fibers is poor and the fibers may settle out, but on the contrary, when the amount of the carboxyl group is more than 2.2 mmol/g, the water-solubility of the fibers may increase and the fibers may tend to give a sticky feeling.

The amount of the carboxyl group in the specific cellulose fibers (component A) may be measured, for example, through potentiometric titration. Namely, the cellulose fibers after drying are dispersed in water, and an aqueous 0.01 N sodium hydroxide solution is added thereto and fully stirred to disperse the cellulose fibers therein. Next, 0.1 N hydrochloric acid solution is added until the pH value of the resulting mixture could reach from 2.5 to 3.0. Then an aqueous 0.04 N sodium hydroxide solution is dropwise added thereto at a speed of 0.1 ml/min. From the difference between the neutralization point of the excess hydrochloric acid on the obtained pH curve and the neutralization point of the cellulose fibers-derived carboxyl group, the amount of the carboxyl group can be calculated.

The amount of the carboxyl group can be controlled by controlling the amount of the co-oxidizing agent to be added and the reaction time in the step of oxidation of the cellulose fibers, as described below.

In the specific cellulose fibers (component A) in the present invention, only the hydroxyl group at the C6 position of the glucose unit on the surfaces of the cellulose fibers is selectively oxidized into an aldehyde group and a carboxyl group. The matter as to whether or not only the hydroxyl group at the C6 position of the glucose unit on the surfaces of the cellulose fibers has been selectively oxidized into an aldehyde group and a carboxyl group can be confirmed on the $^{13}$C-NMR chart of the cellulose fibers. Namely, the peak at 62 ppm, corresponding to the C6 position of the primary hydroxyl group of the glucose unit, which is confirmed in the $^{13}$C-NMR chart of the cellulose before oxidization is lost after the oxidization reaction, and alternatively, a peak derived from the carboxyl group appears at 178 ppm. In that manner, the oxidization of only the C6-positioned hydroxyl group of the glucose unit into an aldehyde group and a carboxyl group can be confirmed.

Next, the cosmetic composition of the present invention includes water (component B) along with the specific cellulose fibers (component A).

The cosmetic composition of the present invention may further include a functional additive (component C) in addition to the above-mentioned specific cellulose fibers (component A) and water (component B). As the functional additive (component C), for example, usable are oily materials, surfactants, alcohols, functional components to be mentioned below and others; and these may be used either singly or as a mixture of two or more of them. Combining these components A to C gives the cosmetic composition.

[Oily Material]

The oily material includes, for example, natural animal and vegetable oils such as jojoba oil, macadamia nut, avocado oil, evening primrose oil, mink oil, rapeseed oil, castor oil, sunflower oil, corn oil, cacao oil, palm oil, rice bran oil, olive oil, almond oil, sesame oil, safflower oil, soybean oil, camellia oil, persic oil, cotton oil, Japan wax, palm oil, palm kernel oil, egg yolk oil, lanolin, squalene, etc.; hydrocarbons such as synthetic triglyceride, squalene, liquid paraffin, vaseline, ceresin, microcrystalline wax, isoparaffin, etc.; waxes such as carnauba wax, paraffin wax, sperm oil, bees wax, camellia wax, lanolin, etc.; higher alcohols such as cetanol, stearyl alcohol, lauryl alcohol, cetostearyl alcohol, oleyl alcohol, behenyl alcohol, lanolin alcohol, hydrogenated lanolin alcohol, hexyl decanol, octyl dodecanol, etc.; higher fatty acids such as lauric acid, myristic acid, palmitic acid, stearic acid, behenic acid, isostearic acid, oleic acid, linolenic acid, linolic acid, oxystearic acid, undecylic acid, lanoline fatty acid, hard lanolin fatty acid, soft lanolin fatty acid, etc.; cholesterol and its derivatives such as cholesteryl-octyldodecyl-behenyl, etc.; esters such as isopropyl myristate, isopropyl palmitate, isopropyl stearate, glycerol 2-ethylhexanoate, butyl stearate, etc.; polar oils such as diethylene glycol monopropyl ether, polyoxyethylene polyoxypropylene pentaerythritol ether, polyoxypropylene butyl ether, ethyl linoleate, etc. As the oily material, for example, there are further mentioned amino-modified silicones, epoxy-modified silicones, carboxyl-modified silicones, carbinol-modified silicones, methacryl-modified silicones, mercapto-modified silicones, phenol-modified silicones, one end-reactive silicones, heterofunctional group-modified silicones, polyether-modified silicones, methylstyryl-modified silicones, alkyl-modified silicones, higher fatty acid-modified silicones, hydrophilic special-modified silicones, higher alkoxy-modified silicones, higher fatty acid-containing silicones, fluorine-modified silicones, etc. More specifically, there are mentioned silicones including various derivatives such as silicone resins, methylphenylpolysiloxane, methylpolysiloxane, octamethylcyclotetrasiloxane, decamethylcyclopentasiloxane, dodecamethylcyclohexanesiloxane, methylcyclopolysiloxane, octanemethyltrisiloxane, decamethyltetrasiloxane, polyoxyethylene-methylpolysiloxane copolymer, polyoxypropylene-methylpolysiloxane copolymer, poly(oxymethylene-oxypropylene)methylpolysiloxane copolymer, methylhydrogenpolysiloxane, tetrahydrotetramethylcyclotetrasiloxane, stearoxymethylpolysiloxane, cetoxymethylpolysiloxane, methylpolysiloxane emulsion, high-polymerization methylpolysiloxane, trimethylsiloxysilicic acid, crosslinked methylpolysiloxane, crosslinked methylphenylpolysiloxane, crosslinked methylphenylpolysiloxane, crosslinked methylphenylpolysiloxane, etc. One or more of these may be used here either singly or in combination.

[Surfactant]

The surfactant includes, for example, nonionic surfactants and alkyl sulfate ester salts such as propylene glycol fatty acid ester, glycerin fatty acid ester, polyglycerin fatty acid ester, polyglycerin fatty acid ester sorbitan fatty acid ester, polyoxyethylene sorbitol fatty acid ester, polyethylene glycol fatty acid ester, polyoxyethylene castor oil, polyoxyethylene hardened castor oil, polyoxyethylene alkyl ether, polyoxyethylene phytosterol, polyoxyethylene polyoxypropylene alkyl ether, polyoxyethylene alkylphenyl ether, polyoxyethylene lanolin, polyoxyethylene lanolin alcohol, polyoxyethylene bees wax derivatives, polyoxyethylene alkylamine, polyoxyethylene fatty acid amide, polyoxyethylene alkylphenyl formaldehyde condensate, polyoxyethylene alkyl ether phosphoric acid (salt), etc.; anionic surfactants such as polyoxyethylene alkyl sulfate ester salt, alkylbenzene sulfonic acid salt, α-olefinsulfonic acid salt, etc.; cationic surfactants such as alkyltrimethylammonium chloride, dialkyldimethylammonium chloride, benzalkonium chloride, etc. natural substances with surface activity such as lecithin, lanolin, cholesterol, saponin, etc.; low-irritation surfactants such as sulfosuccinates, ethylene oxide-propylene oxide block copolymers, etc.; ampholytic surfactants such as lauryldimethylaminoacetic acid betaine, etc. These may be used here either singly or in combination.

[Alcohol]

The alcohol includes, for example, water-soluble alcohols such as ethanol, isopropanol and others soluble in water; water-soluble polyalcohols such as glycerin, ethylene glycol, propylene glycol, butanediol, etc.; and their mixtures.

[Functional Component]

For example, the functional component includes UV absorbents, for example, paraaminobenzoic acid and its derivatives, homomenthyl-7N-acetylalantoylanylate, butylmethoxybenzoylmethane, paramethoxycinnamic acid derivatives such as glycerin di-paramethoxycinnamate mono-2-ethylhexanoate, octyl cinnamate, etc., salicylic acid derivatives such as aminosalicylates, etc., benzophenone derivatives such as 2,4-dihydroxybenzophenone, etc., ethylhexyl dimethoxybenzylidene-dioxoimidazolinepropionate, liquid lanolin acetate, Baikal skullcup root extract, trianilino-p-carboethylhexyloxy-triazine, etc.; skin-whitening components, for example, ascorbic acid and its derivatives such as arbutin, kojic acid, magnesium phosphate ascorbate, etc., glutathione, licorice root extract, clove extract, tea extract, astaxanthin, bovine placenta extract, tocopherol and its derivatives, tranexamic acid and its salts, azulene, γ-hydroxybutyric acid, etc.; moisturizing agents, for example, polyalcohols such as maltitol, sorbitol, glycerin, propylene glycol, 1,3-butylene glycol, polyethylene glycol, glycol, etc., organic acids and their salts such as sodium pyrrolidonecarboxylate, sodium butyrate, sodium citrate, etc., hyaluronic acid and its salts such as sodium hyaluronate, etc., fermentation metabolites such as hydrolyzates of yeast and yeast extract, yeast culture broth, lactic acid bacteria culture broth, etc., water-soluble proteins such as collagen, elastin, keratin, sericin, etc., collagen hydrolyzates, casein hydrolyzates, silk hydrolyzates, peptides and their salts such as sodium polyaspartate, saccharides, polysaccharides and their derivatives such as trehalose, xylobiose, maltose, sucrose, glucose, vegetable viscous polysaccharides, etc., glycosaminoglycan and its salts such as water-soluble chitin, chitosan, pectin, chondroitin sulfate and its salts, etc, amino acids such as glycine, serine, threonine, alanine, aspartic acid, tyrosine, valine, leucine, arginine, glutamine, proline acid, etc., glycoamino acid compounds such as aminocarbonyl reaction product, etc., vegetable extracts such as aloe extract, horse chestnut extract, trimethylglycine, urea, uric acid, ammonia, lecithin, lanolin, squalane, squalene, glucosamine, creatinine, nucleic acid-related substances such as DNA, RNA, etc.; thickeners such as carboxymethyl cellulose, hydroxyethyl cellulose, hydroxypropyltrimethylammonium chloride ether, ethyl cellulose, hydroxylpropyl cellulose, methylhydroxypropyl cellulose, soluble starch, carboxymethyl starch, methyl starch, propylene glycol alginate, polyvinyl alcohol, polyvinyl pyrrolidone, polyvinyl methyl ether, carboxyvinyl polymer, polyacrylic acid, methyl cellulose, hydroxyethyl cellulose, gum arabic, xanthan gum, carrageenan, galactan, pectin, mannan, starch, dextran, succinoglycan, curdlan, hyaluronic acid, gelatin, casein, albumin, collagen, methoxyethylene-maleic anhydride copolymer, amphoteric methacrylate copolymer, polydimethylmethylenepiperidinium chloride, polyacrylate copolymer, polyvinyl alcohol, nitrocellulose, silicone resin, polyoxyethylene glycol fatty acid ester such as polyethylene glycol fatty acid ester, polyethylene glycol distearate, etc., polyoxyethylene fatty acid ester methyl glycoside such as polyoxyethylene dioleic acid methyl glycoside, etc., tetradecenesulfonic acid, etc., metal ion sequestering agents such as ethylenediamine-tetraacetic acid and its salts, phosphoric acid, ascorbic acid, succinic acid, gluconic acid, polyphosphoric acid salts, metaphosphoric acid salts, etc.; organic solvents such as ethanol, propylene glycol, 1,3-butylene glycol, etc.; antioxidants such as butylhydroxytoluene, tocopherol, phytic acid, etc.; antibacterial antiseptics such as benzoic acid and its salts, alkyl paraoxybenzoates (ethylparaben, butylparaben, etc.) and their salts, dehydroacetic acid and its salts, parachlorometacresol, hexachlorophene, boric acid, resorcin, tribromsalan, octophenylphenol, chlorhexidine gluconate, thiram, photosensitive element No. 201, Phenoxyethanol, benzalkonium chloride, benzotonium chloride, halocarban, chlorhexidine chloride, trichlorocarbanide, tocopherol acetate, zinc pyrithione, hinokitiol, phenol, isopropylmethylphenol, 2,4,4-trichloro-2-hydroxyphenol, hexachlorophene, etc.; organic acids such as citric acid, malic acid, tartaric acid, lactic acid, adipic acid, glutamic acid, aspartic acid, maleic acid, etc.; various pharmaceutical agents, for example, blood circulation promoters, e.g., vitamin A and its derivatives, B-complex vitamins such as vitamin B6 hydrochloride, vitamin B6 tripalmitate, vitamin B6 dioctanoate, vitamin B2 and its derivatives, etc., C-complex vitamins such as ascorbic acid, ascorbic acid sulfate ester, ascorbic acid phosphate ester, etc., E-complex vitamins such as α-tocopherol, β-tocopherol, γ-tocopherol, etc., D-complex vitamins, vitamin H, pantothenic acid, and other vitamins, nicotinic acid amide, benzyl nicotinate, γ-orizanol, allantoin, glycyrrhizinic acid (salts), glycyrrhetinic acid and its derivatives, hinokitiol, mucidin, bisabolol, eucalyptol, thymol inositol, saponins (quillaja saponins, bean saponins, luffa saponins, etc.), tranexamic acid, pantothenyl ethyl ether, ethynyl estradiol, cepharandine, placenta extract, swertia japonica extract, cepharanthine, vitamin E and its derivatives, gamma-oryzanol, etc.; regional stimulants such as capsicum tincture, ginger tincture, cantharides tincture, benzyl nicotinate, etc., nutrients such as amino acids, etc., antiinflammatory agents such as glycyrrhetinic acid, glycyrrhizic acid derivatives, carpronium chloride, nonylic acid vanillylamide, allantoin, azulene, aminocaproic acid, hydrocortisone acid, etc., astringents such as zinc oxide, zinc sulfate, allantoin hydroxyaluminium, aluminium chloride, zinc sulfocarbolate, tannic acid, etc., fresheners such as menthol, camphor, etc., antihistamine agents, silicone substances such as polymer silicones, cyclic silicones, etc., antioxidants such as BHA, BHT, gallic acid, NDGA, etc.; natural extracts prepared through extraction or hydrolysis of animals, vegetables, microorganisms or a part thereof with organic solvent, alcohol, polyalcohol, water, water-base alcohol or the like, for example, those from yeast such as saccharomyces, etc., fungi, bacteria, bovine placenta, human placenta, human umbilical cord, yeast, collagen, milk-derived protein, wheat, soybean, bovine blood, swine blood, cock's comb, dog fennel, cucumber, rice, shea butter, white birch, tea, tomato, garlic, hamamelis, rose, sponge cucumber, hop, peach, apricot, lemon, kiwi, dokudami (chameleon plant), capsicum, *Sophora angustifolia*, Japanese dock plant (*Rumex japonicus*), Japanese spatterdock (species of water lily, *Nuphar japonica*), sage, milfoil (*Achillea sibirica*), common mallow, cridium officinale, Japanese green gentian, thyme, dong dang gui (*Angelica acutiloba*), spruce tree, birch, field horsetail, malonie, saxifraga, arnica, lily, wormwood (*Artemisia vulgaris* indica), peony root, aloe, aloe vera, scutellaria root, phellodendron bark, safflower, safflower, *asarum* (Chinese wild ginger), lithospermum root, jujube fruit (Chinese date), citrus unshiu peel, carrot, coix seed, adlay (Job's tears), gardenia, sawara cypress, etc.; colorants; powdery ingredients such as calcium carbonate, talck, kaolin, mica, sulfur, lauroyl lysine, fine particulate silica, titanium dioxide, zinc dioxide, red iron oxide, yellow iron oxide, black iron oxide, nylon 12 powder, polymethyl methacrylate powder, polyethylene powder, polystyrene powder, etc.; polymer additives such as cationated cellulose, carboxyvinyl polymer, carbonylpyrrolidone, polyvinyl pyrrolidone-vinyl acetate copolymer, xanthan gum, hydroxyethyl cellulose, etc.; fragrances, chelating agents; alkalis such as triethanolamine, potassium hydroxide, borax, etc.; antioxidants, etc. One or more of these may be used here either singly or in combination.

The cellulose fibers (component A) for use in the cosmetic composition of the present invention can be produced, for example, as follows. Namely, firstly, a natural cellulose of soft wood pulp or the like is dispersed in water to be a slurry, then sodium bromide, N-oxyradical catalyst are added thereto, and fully stirred to disperse and dissolve them. Next, a co-oxidizing agent such as an aqueous hypochlorous acid solution or the like is added thereto, and then while an aqueous 0.5 N sodium hydroxide solution is dropwise added thereto so as to make it have a pH of 10.0, the reaction is continued until no pH change could be seen. The slurry obtained through the above reaction is purified by washing with water and filtration to remove the unreacted starting material, the catalyst and others to obtain the intended product, aqueous dispersion of specific, surface-oxidized cellulose fibers (component A). In case where higher transparency is required for the cosmetic composition, the dispersion may be further processed with a disperser having a strong dispersing power such as a high-pressure homogenizer or the like to obtain a composition having a higher transparency.

The above-mentioned N-oxyradical catalyst includes, for example, 2,2,6,6-tetramethylpiperidino-oxyradical (TEMPO), 4-acetamide-TEMPO, etc. Adding a catalytic amount of the N-oxyradical catalyst is enough, and preferably, the compound is added to the aqueous reaction solution in an amount falling within a range of from 0.1 to 4 mmol/l, more preferably from 0.2 to 2 mmol/l.

The co-oxidizing agent includes, for example, hypohalogenous acids or their salts, halogenous acids or their salts, perhalic acids or their salts, hydrogen peroxide, perorganic acids, etc. One or more of these may be used here either singly or in combination. Above all, preferred are alkali metal hypohalites such as sodium hypochlorite, sodium hypobromite, etc. In case where sodium hypochlorite is used, preferably, the reaction is promoted in the presence of an alkali metal bromide such as sodium bromide or the like, from the viewpoint of the reaction speed. The amount of the alkali metal bromide to be added may be from about 1 to 40 molar times the amount of the N-oxyradical catalyst, preferably from about 10 to 20 molar times.

The cosmetic composition of the present invention can be produced by suitably incorporating the functional additives (component C) for use for cosmetics, namely, the functional additives such as oily material, surfactant, alcohol, functional ingredient and others, into the aqueous dispersion of cellulose fibers (component A) prepared in the manner as above, followed by mixing and processing them. For the mixing treatment, for example, various kneading machines such as vacuum homomixer, disperser, propeller mixer, kneader, etc., as well as various grinders, blender, homogenizer, ultrasonic homogenizer, colloid mill, pebble mill, bead mill grinder, high-pressure homogenizer, ultrahigh-pressure homogenizer, etc can be used.

The amount of the specific cellulose fibers (component A) in the cosmetic composition of the present invention may vary depending on the desired function. In general, it falls within a range of from 0.01 to 6.0% by weight, and from the viewpoint of the feeling in use, it is preferably within a range of from 0.1 to 2.0% by mass. The amount of the oily material, the surfactant or the functional ingredient may be suitably defined depending on the use of the cosmetic material. By changing the concentration of the cellulose fibers (component A), the amount of various ingredients, and the dispersion treatment condition in mixing, cosmetic compositions having desired properties can be obtained.

The cosmetic composition of the present invention, thus obtained, can be used, for example, for skincare cosmetics such as face lotion, emulsion, cold cream, vanishing cream, massage cream, emollient cream, cleansing cream, beauty essence, pack, foundation, sunscreen cosmetic, sun-tanning cosmetic, moisture cream, hand cream, skin-whitening emulsion, various lotions, etc.; hair-care cosmetics such as shampoo, rinse, hair conditioner, rinse-in shampoo, hair-styling agent (hair foam, gel-type hair dressing, etc.), hair treatment agent (hair cream, treatment lotion, etc.), hair dye, lotion-type hair-growing agent, hair tonic, etc.; cleaning agents such as hand cleaner, etc.; as well as pre-shaving lotion, after-shaving lotion, air freshener, dentifrice, ointment, adhesive patch, etc.

[Gel-Type Composition]

The gel-type composition is explained next.

The gel-type composition of the present invention includes the specific cellulose fibers (component A') and water (component B).

In the gel-type composition of the present invention, the content of the specific cellulose fibers (component A') is defined to be from 0.3 to 5.0% by weight of the entire gel-type composition, preferably from 0.5 to 3.0% by weight. Specifically, when the content of the component A' falls within the above range, then the composition can keep high viscosity even in the co-presence of salts, ionic surfactants, etc. As opposed to this, when the content of the component A' is less than 0.3% by mass, the composition could not be in a gel stage when functional additives are added thereto, but would be fluid. On the contrary, when the content of the component A' is more than 5.0% by weight, then the composition is extremely highly viscous and could not be microfibrillated in the subsequent dispersion step. Therefore the composition could not be a macroscopically homogeneous gel-type composition, namely, the intended gel-type composition could not be substantially obtained.

The specific fine cellulose fibers (component A') for use in the gel-type composition of the present invention are, like the fine cellulose fibers for use in the above-mentioned cosmetic composition, cellulose fibers in which the hydroxyl groups are partly oxidized into an aldehyde group and a carboxyl group, and which have a maximum fiber diameter of 1000 nm or less. However, the number-average fiber diameter of the cellulose fibers is from 2 to 150 nm, and preferably, the maximum fiber diameter thereof is 500 nm or less and the number-average fiber diameter thereof is from 2 to 100 nm, and more preferably, the maximum fiber diameter thereof is 30 nm or less and the number-average fiber diameter thereof is from 2 to 10 nm. When cellulose fibers of which the maximum fiber diameter is more than 1000 nm or the number-average fiber diameter is more than 150 nm are used, then the cellulose fibers may settle down and the composition could not be in the form of a gel with keeping flowability.

Analyzing the fibers to determine the maximum fiber diameter and the number-average fiber diameter thereof can be attained in the same manner as that described hereinabove in the section of the cosmetic composition. Namely, for example, the fibers can be analyzed as follows. Briefly, an aqueous fine cellulose dispersion having a solid fraction of from 0.05 to 0.1% by weight is prepared, then the dispersion is cast onto a hydrophilicated carbon film-coated grid to prepare a sample for transmission electronic microscopy (TEM). In case where the sample contains fibers having a large fiber diameter which is not included the scope of the present invention, the surface of the sample cast onto a glass plate may be observed with a scanning electronic microscope (SEM). Depending on the size of the constituent fibers, the microscopic observation may be attained at any of 5000-power, 10000-power or 50000-power magnifications. In the picture image, vertical and horizontal axes for any desired image size are simulated, and the sample and the observation condition (magnification, etc.) are so controlled that at least 20 fibers could cross the axes. After obtaining the sample picture image satisfying the condition, vertical and horizontal two axes are drawn at random in one image, and the fiber diameter of the fibers crossing each axis is visually read. In that manner, at least three non-overlapping surface images are taken with the electron microscope, and the value of the fiber diameter of the fibers each crossing the two axes is read (accordingly, the information of fiber diameter of at least 120 fibers=20 fibers×2×3 can be thereby obtained). Based on the data of the fiber diameter thus obtained in the manner as above, the maximum fiber diameter and the number-average fiber diameter are calculated.

Next, the amount of the carboxyl group and that of the aldehyde group in the specific cellulose fibers (component A') for use in the present invention are described. In general, when the total amount of the carboxyl group and the aldehyde group existing in cellulose is large, then the fibers are preferred since it can be exist stably in the form of fine fibers having a finer fiber diameter. In the present invention, from the viewpoint that the composition can be thickened even with small added amount, the amount of the aldehyde group in the specific cellulose fibers (component A') is defined to fall within a range of from 0.08 to 0.3 mmol/g and the amount of the carboxyl group therein is within a range of from 0.6 to 2.0 mmol/g; and preferably, the amount of the aldehyde group is within a range of from 0.10 to 0.25 mmol/g and the amount of the carboxyl group therein is within a range of from 0.8 to 1.6 mmol/g. Specifically, when the amount of the carboxyl group and the amount of the aldehyde group are defined each to fall within the above range, then the specific cellulose fibers (component A') can stably exist in the gel with no aggregation and precipitation therein.

The desired amount of the carboxyl group and that of the aldehyde group can be controlled by controlling the amount of the co-oxidizing agent to be used in the step of oxidizing the cellulose fibers and the reaction time therein.

The amount of the carboxyl group can be measured according to the method mentioned below. The amount of the aldehyde group can be measured through potentiometric titration as follows.

[Measurement of Amount of Carboxyl Group]

Using a cellulose sample of which the dry weight has been measured accurately, 60 ml of a slurry having a concentration of from 0.5 to 1% by weight of the cellulose sample is prepared; its pH is controlled to be at about 2.5 with an aqueous 0.1 M hydrochloric acid solution added thereto; and then an aqueous 0.05 M sodium hydroxide solution is dropwise added thereto for measurement of the electric conductivity. The measurement is continued until the pH of the solution could reach about 11. From the amount of sodium hydroxide (V) consumed in the neutralization stage with a weak acid where the change of the electric conductivity is gentle, the amount 1 of the functional group (amount of carboxyl group) can be obtained according to the following formula (1).

[Numerical Formula 1]

$$\text{Amount of Functional Group 1 (mmol/g)} = V \text{ (ml)} \times 0.05/(\text{mass of cellulose, g}) \quad (1)$$

[Measurement of Amount of Aldehyde Group]

The same cellulose sample as above is further oxidized in an aqueous 2% sodium hypochlorite solution, which has been controlled to have a pH of from 4 to 5 with acetic acid, for 48 hours at room temperature (25° C.), and the amount 2 of the functional group is determined according to the above formula (1). With that, the amount of the functional group added by this oxidation (amount of functional group 2−amount of functional group 1) is calculated to obtain the amount of the aldehyde group.

Introduction of the aldehyde group or the carboxyl group into the cellulose of the specific cellulose fibers can be confirmed as follows. Namely, water is completely removed from the sample and the sample is analyzed through attenuated total IR reflectiometry (ATR), in which the presence of carbonyl group-caused absorption (at around 1608 $cm^{-1}$) and acid-type carboxyl group (COOH)-caused absorption (at around 1730 $cm^{-1}$) is confirmed.

Next, the above-mentioned specific cellulose fibers (component A') can be produced in the same manner as in the case of the above-mentioned cosmetic composition. More precisely, for example, the fibers can be produced in a process including (1) an oxidation step, (2) a purification step and (3) a dispersion step (microfibrillation step). The steps are described in order.

(1) Oxidation Step

A natural cellulose and an N-oxyl compound are dispersed in water (dispersion medium), then a co-oxidizing agent is added thereto and the reaction is started. During the reaction, an aqueous 0.5 M sodium hydroxide solution is dropwise added so as to keep the pH of the system to be from 10 to 11, and at the time when the pH change can be no more seen, the reaction is considered to have stopped. In this connection, the co-oxidizing agent is not a substance which directly oxidizes the cellulose hydroxyl group but a substance that oxidizes the N-oxyl compound serving as an oxidation catalyst.

The natural cellulose means a pure cellulose isolated from a biosynthetic system of cellulose such as a vegetable, animal or bacteria-produced gel or the like. More specifically, it includes cellulose isolated from cotton pulp such as soft wood pulp, hard wood pulp, cotton linter, cotton lint or the like, non-wood pulp such as wheat straw pulp, bagasse pulp, etc., or bacteria cellulose (BC), cellulose isolated from ascidian, cellulose isolated from sea weeds, etc. One or more of these may be used here either singly or in combination. Of those, preferred are cotton pulp such as soft wood pulp, hard wood pulp, cotton linter, cotton lint or the like, and non-wood pulp such as wheat straw pulp, bagasse pulp, etc. When the natural cellulose is specifically processed by beating so as to increase the surface area thereof, then the reaction efficiency thereof can be favorably increased and the producibility can be thereby enhanced. In case where the natural cellulose that has been isolated and purified and, without being dried (never dry), stored is used, the bundle of the microfibrils can be readily swollen. Therefore, the cellulose in the state is preferably used here as the reaction efficiency is enhanced and the number-average fiber diameter of the microfibrillated fibers can be downsized.

The dispersion medium for the natural cellulose in the above reaction is water, and the concentration of the natural cellulose in the aqueous reaction solution may be any one with no limitation thereon so far as it enables sufficient diffusion of the reagent (natural cellulose). In general, the concentration is at most about 5% relative to the weight of the aqueous reaction solution, but the reaction concentration can be increased by using an apparatus having a strong mechanical stirring force.

As the N-oxyl compound, for example, a compound having a nitroxy radical that is used as a general oxidizing catalyst is generally mentioned. The N-oxyl compound is preferably a water-soluble compound; and especially preferred is piperidinenitroxy oxyradical, more preferred is 2,2,6,6-tetramethylpiperidino-oxy radical (TEMPO) or 4-acetamide-TEMPO. Adding a catalytic amount of the N-oxyradical catalyst is enough, and preferably, the compound is added to the aqueous reaction solution in an amount falling within a range of from 0.1 to 4 mmol/l, more preferably from 0.2 to 2 mmol/l.

The co-oxidizing agent includes, for example, hypohalogenous acids or their salts, halogenous acids or their salts, perhalic acids or their salts, hydrogen peroxide, perorganic acids, etc. One or more of these may be used here either singly or in combination. Above all, preferred are alkali metal hypohalites such as sodium hypochlorite, sodium hypobromite, etc. In case where sodium hypochlorite is used, preferably, the reaction is promoted in the presence of an alkali metal bromide such as sodium bromide or the like, from the viewpoint of the reaction speed. The amount of the alkali metal bromide to be added may be from about 1 to 40 molar times, preferably from about 10 to 20 molar times, of the amount of the N-oxyradical catalyst.

Preferably, the pH of the aqueous reaction solution is kept within a range of from about 8 to 11. Although the temperature of the aqueous solution may be freely within a range of from about 4 to 40° C., the reaction may be attained at room temperature (25° C.) and the temperature control is not specifically needed.

For obtaining the desired amount of the carboxyl group and the desired amount of the aldehyde group, the oxidation degree is controlled by controlling the amount of the co-oxidizing agent to be added and the reaction time. In general, the reaction time may be from about 5 to 120 minutes, and the reaction could finish at longest within 240 minutes.

(2) Purification Step

Next, for the purpose of removing the unreacted co-oxidizing agent (hypochlorous acid, etc.) and various side products and others, the reaction product is purified. In this stage, the reaction product fibers are not broken and dispersed to the nanofiber unit. Therefore, the reaction product is purified according to an ordinary purification method of repeatedly washing it with water and filtering it to obtain an aqueous dispersion of high purity (99% by weight or more) reaction product fibers and water.

In the purification method of the purification step, any apparatus capable of attaining the intended object can be used, for example, according to a method of using centrifugal water removal (with, for example, a continuous decanter). Thus obtained, the aqueous dispersion of the reaction product fibers has, in the squeezed state thereof, a solid (cellulose) concentration of from about 10% by weight to 50% by weight. In consideration of the subsequent dispersion step, a higher concentration than 50% by weight is unfavorable since an extremely high level of energy would be needed for the dispersion.

(3) Dispersion Step (Microfibrillation Step)

The water-containing reaction product fibers obtained in the above purification step are dispersed in a dispersion medium. With the treatment, the viscosity of the system increases and a dispersion of microfibrillated cellulose fibers can be obtained. After that, the cellulose fiber dispersion is dried to obtain specific cellulose fibers (component A'). The cellulose fiber dispersion may be used directly without drying as it is in the gel-type composition with no problem.

As the dispersion medium for the specific cellulose fibers (component A') obtained in the manner as above, water (component B) is used.

As a dispersing apparatus to be used in the dispersion step, an apparatus having a strong beating force, such as high-speed revolution homomixer, high-pressure homogenizer, ultrahigh-pressure homogenizer, ultrasonic disperser, beater, disc-type refiner, conical refiner, double disc-type refiner, grinder or the like is preferable since it enable more efficient and high-level downsizing to obtain the intended gel-type composition in an economically advantageous manner. As the dispersing apparatus, for example, a screw-type mixer, a paddle mixer, a disperser-type mixer, a turbine-type mixer or the like may also be used with no problem.

Regarding the drying method for the cellulose fiber dispersion, for example, when the dispersion medium is water, a spray-drying method, a freeze-drying method or the like is used. When the dispersion medium is a mixed solution of water and an organic solvent, a drying method with a drier, a spray-drying method with a spray drier, or the like can be used.

The gel-type composition of the present invention may contain a functional additive (component C') along with the above-mentioned specific cellulose fibers (component A') and water (component B). The functional additive (component C') includes, for example, inorganic salts, organic salts, surfactants, oils, moisturizers, antiseptics, organic fine particles, inorganic fine particles, deodorants, fragrances, organic solvents, etc. One or more of these may be used here either singly or in combination.

The inorganic salts are preferably those soluble or dispersible in water (component B), and for example, include salts of hydrogen halides, sulfuric acid, carbonic acid or the like with alkali metals, alkaline earth metals, transition metals, etc. Specifically, NaCl, KCl, $CaCl_2$, $MgCl_2$, $(NH_4)_2SO_4$, $Na_2CO_3$, etc. are mentioned. One or more of these may be used here either singly or in combination.

Not specifically defined, the organic acid salts usable herein may be any substantially water-soluble or water-dispersible substances as prepared by neutralizing the carboxyl group, a phosphoric acid group, a sulfonic acid group or the like existing in molecules with hydroxides of alkali metals, alkaline earth metals or the like or with organic amines, etc.

The surfactants are preferably those soluble or dispersible in water (component B), and for example, sulfonic acid-type surfactants such as sodium alkylsulfosuccinates, sodium alkylsulfonates, alkylsulfate ester salts, etc.; phosphate-type surfactants such as polyoxyethylene alkylphosphate esters, etc.; nonionic surfactants such as higher alcohol alkylene oxide adducts, alkylarylphenol alkylene oxide adducts, etc are mentioned. One or more of these may be used here either singly or in combination.

The oils include, for example, silicone oils such as methylpolysiloxane, silicone polyether copolymer, etc.; vegetable oils such as olive oil, castor oil, etc.; animal oils, lanolin, liquid paraffin, squalene, etc. One or more of these may be used here either singly or in combination.

The moisturizers include, for example, hyaluronic acid, glycerin, 1,3-butylene glycol, sorbitol, dipropylene glycol, etc. One or more of these may be used here either singly or in combination.

The organic fine particles include, for example, styrene-butadiene latex, acrylic emulsion, urethane emulsion, etc. One or more of these may be used here either singly or in combination.

The inorganic fine particles include, for example, titanium oxide, silica compounds, carbon black, etc. One or more of these may be used here either singly or in combination.

The antiseptics include, for example, methylparaben, ethylparaben, etc. One or more of these may be used here either singly or in combination.

The deodorants and fragrances include, for example, D-limonene, decyl aldehyde, menthone, pulegone, eugenol, cinnamaldehyde, benzaldehyde, menthol, peppermint oil, lemon oil, orange oil, as well as deodorant effective ingredients extracted from various organs of vegetables (for example, oxalis, Korean houttynia, hemlock fir (*Tsuga sieboldii*), gingko, Japanese black pine, larch, Japanese red pine, empress tree, fortune tea olive, lilac, orange osmanthus (sweet tea), giant butterbur, tsuwabuki (*Farfugium japonicum*), forsythia, etc.) with water or hydrophilic organic solvent. One or more of these may be used here either singly or in combination.

The organic solvents include, for example, water-soluble alcohols (methanol, ethanol, isopropanol, isobutanoyl, sec-butanol, tert-butanol, methyl cellosolve, ethyl cellosolve, ethylene glycol, glycerin, etc.), ethers (ethylene glycol dimethyl ether, 1,4-dioxane, tetrahydrofuran, etc.), ketones (acetone, methyl ethyl ketone), N,N-dimethylformamide, N,N-dimethylacetamide, dimethyl sulfoxide, etc. One or more of these may be used here either singly or in combination.

Although the amount of the functional additive (component C') is preferably one necessary for expressing the intended effect of the functional additive, it is not specifically defined.

The gel-type composition of the present invention can be obtained, for example, by suitably blending the above-mentioned specific cellulose fibers (component A') and water (component B) and, if necessary, the functional additive (component C') followed by mixing them.

For mixing the components, for example, various kneading machines such as vacuum homomixer, disperser, propeller mixer, kneader, etc.; various grinding machines, as well as blender, homogenizer, ultrasonic homogenizer, colloid mill, pebble mill, bead mill grinder, high-pressure homogenizer, ultrahigh-pressure homogenizer, etc can be used.

The viscosity of the gel-type composition of the present invention, thus obtained, is preferably at least 15 Pa·s, preferably within a range of from 30 to 150 Pa·s.

The viscosity can be measured, for example, using a BH-type viscometer (No. 4 rotor), etc.

In this connection, the amount of water (component B) in the gel-type composition is so controlled that content of the specific cellulose fibers (component A') in the composition could be from 0.1 to 5.0% by weight of the entire composition. Specifically, in case where the gel-type composition of the present invention is composed of the specific cellulose fibers (component A') and water (component B) alone, the mixing amount of water (component B) in the composition (95% by weight to 99.9% by weight) is obtained after subtracting the content of the specific cellulose fibers (component A') (from 0.1 to 5.0% by weight) in the composition from the amount of the entire composition. On the other hand, in case where the gel-type composition of the present invention contains the functional additive (component C') or the like in addition to the specific cellulose fibers (component A') and water (component B), the mixing amount of water (component B) in the composition is obtained after subtracting the content of the specific cellulose fibers (component A') (from 0.1 to 5.0% by weight) and the content of the functional additive (component C') or the like in the composition from the amount of the entire composition.

[Spray Composition]

The spray composition is described next.

The spray composition of the present invention includes the following components (A") and (B), in which the content of the cellulose fibers of the component (A") is from 0.1 to 3.0% by weight, and the maximum value of the viscosity ($\eta_{max}$) of the composition, which is measured with a cone-plate type rotatory viscometer at 20° C. in a shear rate region including from $1 \times 10^{-3}$ $S^{-1}$ to $1 \times 10^{3}$ $S^{-1}$, is $\eta_{max} \geq 1 \times 10^{4}$ mPa·s, and the minimum value of the viscosity ($\eta_{min}$) is $\eta_{min} \leq 1 \times 10^{2}$ mPa·s.

(A") Cellulose fibers having a maximum fiber diameter of 1000 nm or less and a number-average fiber diameter of from 2 to 150 nm, wherein the cellulose has a cellulose I-type crystal structure, the hydroxyl group at the C6-position of the glucose unit in the cellulose molecule is selectively oxidized and modified into an aldehyde group and a carboxyl group, and the amount of the carboxyl group is from 0.6 to 2.0 mmol/g and the amount of the aldehyde group is from 0.05 to 0.3 mmol/l.

(B) Water.

The fine cellulose fibers of the above component (A") are, like those in the above-mentioned cosmetic composition and gel-type composition, have a maximum fiber diameter of 1000 nm or less and a number-average fiber diameter of from 2 to 150 nm. Preferably, the maximum diameter is 500 nm or less, and the number-average fiber diameter is from 2 to 100 nm; more preferably, the maximum fiber diameter is 30 nm or less, and the number-average fiber diameter is from 2 to 10 nm. This is because when cellulose fibers of which the maximum fiber diameter is larger than 1000 nm and the number-average fiber diameter is larger than 150 nm are used, the cellulose fibers settle down and could not form a uniform gel-like composition.

In this connection, the cellulose fibers may be analyzed for determining the maximum fiber diameter and the number-average fiber diameter thereof in the same manner as those for the gel-like composition. Specifically, an aqueous fine cellulose dispersion having a solid fraction of from 0.05 to 0.1% by weight is prepared, then the dispersion is cast onto a hydrophilicated carbon film-coated grid to prepare a sample for transmission electronic microscopy (TEM). In case where the sample contains fibers having a large fiber diameter which is not included in the scope of the present invention, the surface of the sample cast onto a glass plate may be observed with a scanning electronic microscope (SEM), and the image may be analyzed. Depending on the size of the constituent fibers, the microscopic observation may be attained at any of 5000-power, 10000-power or 50000-power magnifications. In the picture image, vertical and horizontal axes for any desired image size are simulated, and the sample and the observation condition (magnification, etc.) are so controlled that at least 20 fibers could cross the axes. After the sample picture image satisfying the condition is obtained, vertical and horizontal two axes are drawn at random in one image, and the fiber diameter of the fibers crossing each axis is visually read. In that manner, at least three non-overlapping surface images are taken with the electron microscope, and the value of the fiber diameter of the fibers each crossing the two axes is read (accordingly, the information of fiber diameter of at least 120 fibers=20 fibers×2×3 can be thereby obtained). Based on the data of the fiber diameter thus obtained in the manner as above, the maximum fiber diameter and the number-average fiber diameter are calculated.

The cellulose to constitute the cellulose fibers of the component (A") has a cellulose I-type crystal structure, and a part of the hydroxyl group of the cellulose (the hydroxyl group at the C6-position of the glucose unit in the cellulose molecule) is selectively oxidized into a carboxyl group and an aldehyde group. This means that the cellulose fibers of the component (A") are surface-oxidized microfibrillated fibers of a naturally-derived cellulose solid material having an I-type crystal structure. Specifically, in a process of biosynthesis of natural cellulose, nanofibers called microfibrils are firstly formed almost unexceptionally, and these are multi-bundled to give a high-order solid structure. However, in the present invention, for attenuating the hydrogen bonding between the surfaces of the microfibrils, which serves as a locomotive for the strong aggregation force between these microfibrils, a part of the hydroxyl group is oxidized and converted into an aldehyde group and a carboxyl group.

In case where the cellulose fibers of the component (A") are oxidized with a co-oxidizing agent in the presence of an N-oxyl compound, the amount of the carboxyl group and the amount of the aldehyde group in the cellulose fibers can be readily controlled to fall within a suitable range, and the spray composition of the type can exhibit better results. In this connection, the co-oxidizing agent is not a substance that directly oxidizes the cellulose hydroxyl group but a substance that oxidizes the N-oxyl compound serving as an oxidation catalyst.

In this connection, the cellulose to constitute the cellulose fibers of the component A" has an I-type crystal structure, which can be identified by wide-angle X-ray diffractiometry thereof like in the above. Briefly, the cellulose can be identified by the typical peaks appearing at two positions near 2θ=14 to 17° and near 2θ=22 to 23° in the diffraction profile. Since the cellulose has an I-type crystal structure, and in the spray composition of the present invention, the cellulose fibers do not dissolve in water but exist as microscopically dispersing therein. Consequently, the spray composition enables not only fine fog drip spraying but also, when it is used as a face lotion and applied to a face, another effect of giving a silky feeling to the skin.

In addition, in the spray composition of the present invention, the cellulose constituting the cellulose fibers of the component (A") has a carboxyl group in an amount of from 0.6 to 2.0 mmol/g, like that of the fine cellulose fibers (A') for use in the gel-type composition mentioned above. However, in this, the cellulose has an aldehyde group in an amount of from 0.05 to 0.3 mmol/g. Especially preferably, the cellulose has a carboxyl group in an amount of from 0.8 to 1.8 mmol/g and an aldehyde group in an amount of from 0.08 to 0.25 mmol/g. Falling within the range, the fine cellulose fibers (A") having such a small fiber diameter can stably exist in the gel without aggregating and settling out therein, and even when a small amount of the cellulose fibers of the type is in the composition, the composition can have a high viscosity and can efficiently keep the gel state thereof In this connection, the amount of the carboxyl group and the amount of the aldehyde group in the cellulose fibers can be determined in the same manner as those in the gel-type composition mentioned above. Namely, using a cellulose sample of which the dry weight has been measured accurately, 60 ml of a slurry having a concentration of from 0.5 to 1% by weight of the cellulose sample is prepared; its pH is controlled to be at about 2.5 with an aqueous 0.1 M hydrochloric acid solution added thereto; and then an aqueous 0.05 M sodium hydroxide solution is dropwise added thereto for measurement of the electric conductivity. The measurement is continued until the pH of the solution could reach about 11. From the amount of sodium hydroxide (V) consumed in the neutralization stage with a weak acid where the change of the electric conductivity is gentle, the amount of the functional group (a) can be obtained according to the following formula (2). The amount of the functional group (a) indicates the amount of the carboxyl group in the sample.
[Numerical Formula 2]

$$\text{Amount of Functional Group (mmol/g)} = V \text{ (ml)} \times 0.05 / \text{(mass of cellulose, g)} \quad (2)$$

Next, the same cellulose sample as above is further oxidized in an aqueous 2% sodium hypochlorite solution, which has been controlled to have a pH of from 4 to 5 with acetic acid, for 48 hours at room temperature. Then it is again neutralized according to the same method as above, and from the amount of sodium hydroxide (V) consumed for the neutralization, the amount of the functional group (b) is determined according to the above formula (2). The amount of the functional group added by the oxidation [(b)−(a)] indicates the amount of the aldehyde group in the sample.

Introduction of the carboxyl group and the aldehyde group into the cellulose of the cellulose fibers of the component (A") can be confirmed as follows. Namely, water is completely removed from the sample, and the sample analyzed through attenuated total IR reflectiometry (ATR), in which the presence of carbonyl group-caused absorption (at around 1608 $cm^{-1}$) is confirmed. In particular, the acid-type carboxyl group (COOH) shows the absorption at 1730 $cm^{-1}$.

Next, the cellulose fibers of component (A") can be produced in the same manner as in the case of the above-mentioned cosmetic composition and gel-type composition. Specifically, the fibers can be produced in a process including (1) an oxidation step, (2) a purification step and (3) a dispersion step (microfibrillation step). The steps are described in order.

(1) Oxidation Step

A dispersion of a natural cellulose in water for use in the oxidation step is firstly prepared. In this connection, the natural cellulose means a pure cellulose isolated from a biosynthetic system of cellulose such as a vegetable, animal or bacteria-produced gel or the like. More specifically, it includes cellulose isolated from cotton pulp such as soft wood pulp, hard wood pulp, cotton linter, cotton lint or the like, non-wood pulp such as wheat straw pulp, bagasse pulp, etc., or bacteria cellulose (BC), cellulose isolated from ascidian, cellulose isolated from sea weeds, etc. Of those, preferable ones for the cotton fibers for use in the present invention are cotton pulp such as soft wood pulp, hard wood pulp, cotton linter, cotton lint or the like, and non-wood pulp such as wheat straw pulp, bagasse pulp, etc. When the natural cellulose is specifically processed by beating so as to increase the surface area thereof, then the reaction efficiency thereof can be favorably increased and the producibility can be thereby enhanced. In case where the natural cellulose that has been isolated and purified and, without drying (never drying), stored is used, since the bundle of the microfibrils can be readily swollen, the cellulose in the state is preferably used here as the reaction efficiency is enhanced and the number-average fiber diameter of the microfibrillated fibers can be downsized.

Next, the cellulose fibers are oxidized, for example, with a co-oxidizing agent in the presence of an N-oxyl compound.

As the N-oxyl compound, herein usable is a compound having a nitroxy radical that is generally used as an oxidation catalyst. Above all, the N-oxyl compound for use in the present invention is a water-soluble compound. Especially preferred is piperidinenitroxy oxyradical, more preferred is TEMPO (2,2,6,6-tetramethylpiperidino-oxy radical) or 4-acetamide-TEMPO. Adding a catalytic amount of the N-oxyradical catalyst is enough, and preferably, the compound is added to the aqueous reaction solution in an amount falling within a range of from 0.1 to 4 mmol/l, more preferably from 0.2 to 2 mmol/l.

The co-oxidizing agent includes, for example, hypohalogenous acids or their salts, halogenous acids or their salts, perhalic acids or their salts, hydrogen peroxide, perorganic acids, etc. Preferred are alkali metal hypohalites such as sodium hypochlorite, sodium hypobromite, etc. In case where sodium hypochlorite is used, preferably, the reaction is promoted in the presence of an alkali metal bromide such as sodium bromide or the like, from the viewpoint of the reaction speed. The amount of the alkali metal bromide to be added may be from about 1 to 40 molar times the amount of the N-oxyradical catalyst, preferably from about 10 to 20 molar times.

Preferably, the pH of the aqueous reaction solution is kept within a range of from about 8 to 11. The temperature of the aqueous solution may be freely within a range of from about 4 to 40° C. and the reaction may be attained at room temperature and the temperature control is not specifically needed.

For obtaining the desired amount of the carboxyl group and the desired amount of the aldehyde group, the oxidation degree is controlled by controlling the amount of the co-oxidizing agent to be added and the reaction time. In general, the reaction time may be from about 5 to 120 minutes, and the reaction could finish at longest within 240 minutes.

(2) Purification Step

Next, for the fibers after the oxidation step (reaction product fibers) are purified. The reaction step is for removing the unreacted hypochlorous acid and various side products and others from the reaction product fibers to thereby purify the fibers. In this stage, the reaction product fibers are not broken and dispersed to the nanofiber unit, and is purified according to an ordinary purification method of repeatedly washing it with water and filtering it to obtain an aqueous dispersion of the reaction product fibers having a high purity (at least 99% by weight) and water. In the purification method of the purification step, any apparatus capable of attaining the intended object can be used, for example, according to a method of using centrifugal water removal (with, for example, a continuous decanter). Thus obtained, the aqueous dispersion of the reaction product fibers has, in the squeezed state thereof, a solid (cellulose) concentration of from about 10% by weight to 50% by weight. In consideration of the subsequent dispersion step of dispersing the fibers into nanofibers, a higher concentration than 50% by weight is unfavorable since an extremely high level of energy would be needed for the dispersion.

(3) Dispersion Step (Microfibrillation Step)

The reaction product fibers obtained after the above purification step are processed in a dispersion step (microfibrillation step). The dispersion (microfibrillation) of the reaction product fibers in the dispersion step depends on the degree of the reaction in the reaction product fibers (degree of conversion into the aldehyde group and the carboxyl group). Regarding the reaction product fibers in which the reaction has been appropriately proceeded, those after the purification step (aqueous dispersion) may be processed with general-purpose dispersing machine, for example, a screw-type mixer, a paddle mixer, a disperser-type mixer, a turbine-type mixer or the like, to obtain the intended dispersion. In the stage of dispersion treatment (microfibrillation treatment) of the reaction product fibers, if desired, a part or all of water (dispersion medium) of the above-mentioned component (B) and the functional additives may be added during the dispersion treatment. As the dispersing apparatus to be used in the dispersion step, an apparatus having a strong beating force, such as high-speed revolution homomixer, high-pressure homogenizer, ultrahigh-pressure homogenizer, ultrasonic disperser, beater, disc-type refiner, conical refiner, double disc-type refiner, grinder or the like is preferable since it enables more efficient and high-level downsizing to give the intended gel-type composition having a desired fiber diameter range in an economically advantageous manner.

As the dispersion medium for the cellulose fibers of the component (A″) obtained in the manner as above, water [component (B)] is used.

The optical functional additive [component (C″)] to be used along with the above-mentioned component (A″) and component (B) could cover a broader range than that of the additives used in the cosmetic composition. For example, it includes electrodes, ionic substances, surfactants, oils, moisturizers, organic fine particles, inorganic fine particles, antiseptics, deodorants, fragrances, organic solvents, etc. In particular, even when an electrolyte or an ionic substance (including an ionic surfactant) is incorporated in the spray composition of the present invention, the composition still has a high viscosity and shows a gel state to keep the gel state thereof not providing separation or water release. Therefore, the spray composition of the present invention exhibits excellent performance for those that need such functional additives to be incorporated therein.

The electrolytes and ionic substances include those capable of dissolving or dispersing in a dispersion medium such as water, for example, salts of a hydrogen halide, sulfuric acid, carbonic acid, an organic acid having at least one carboxyl group in the molecule or the like with an alkali metal, an alkaline earth metal, a transition metal or the like, such as sodium chloride, sodium edetate, sodium ascorbate, sulfonic acid-type surfactants such as sodium alkylsulfosuccinates, sodium alkylsulfonates, alkylsulfate ester salts, polyoxyethylene alkylsulfate ester salts, alkylbenzenesulfonate salts, etc.; phosphate-type surfactants such as polyoxyethylene alkylphosphate esters, etc.

The nonionic surfactants include, for example, propylene glycol fatty acid ester, glycerin fatty acid ester, polyoxyethylene glycerin fatty acid ester, polyglycerin fatty acid ester sorbitan fatty acid ester, polyoxyethylene sorbitol fatty acid ester, polyethylene glycol fatty acid ester, polyoxyethylene castor oil, polyoxyethylene hardened castor oil, polyoxyethylene alkyl ether, polyoxyethylene phytosterol, polyoxyethylene polyoxypropylene alkyl ether, polyoxyethylene alkylphenyl ether, polyoxyethylene lanolin, polyoxyethylene lanolin alcohol, polyoxyethylene bees wax derivatives, polyoxyethylene alkylamine, polyoxyethylene fatty acid amide, polyoxyethylene alkylphenyl formaldehyde condensate, etc.

The oils include, for example, natural animal and vegetable oils such as jojoba oil, macadamia nut, avocado oil, evening primrose oil, mink oil, rapeseed oil, castor oil, sunflower oil, corn oil, cacao oil, palm oil, rice bran oil, olive oil, almond oil, sesame oil, safflower oil, soybean oil, camellia oil, persic oil, mink oil, cotton seed oil, Japan wax, palm oil, palm kernel oil, egg yolk oil, lanolin, squalene, etc.; hydrocarbons such as synthetic triglyceride, squalene, liquid paraffin, vaseline, ceresin, microcrystalline wax, isoparaffin, etc.; waxes such as carnauba wax, paraffin wax, sperm oil, bees wax, camellia wax, lanolin, etc.; higher alcohols (cetanol, stearyl alcohol, lauryl alcohol, cetostearyl alcohol, oleyl alcohol, behenyl alcohol, lanolin alcohol, hydrogenated lanolin alcohol, hexyl decanol, octyl dodecanol, etc.); higher fatty acids such as lauric acid, myristic acid, palmitic acid, stearic acid, behenic acid, isostearic acid, oleic acid, linolenic acid, linolic acid, oxystearic acid, undecylic acid, lanoline fatty acid, hard lanolin fatty acid, soft lanolin fatty acid, etc.; cholesterol and its derivatives such as cholesteryl-octyldodecyl-behenyl, etc.; esters such as isopropyl myristate, isopropyl palmitate, isopropyl stearate, glycerol 2-ethylhexanoate, butyl stearate, etc.; polar oils such as diethylene glycol monopropyl ether, polyoxyethylene polyoxypropylene pentaerythritol ether, polyoxypropylene butyl ether, ethyl linoleate, etc.; amino-modified silicones, epoxy-modified silicones, carboxyl-modified silicones, carbinol-modified silicones, methacryl-modified silicones, mercapto-modified silicones, phenol-modified silicones, one end-reactive silicones, heterofunctional group-modified silicones, polyether-modified silicones, methylstyryl-modified silicones, alkyl-modified silicones, higher fatty acid ester-modified silicones, hydrophilic special-modified silicones, higher alkoxy-modified silicones, higher fatty acid-containing silicones, fluorine-modified silicones, etc. One or more of these may be used here either singly or in combination.

More specifically, the silicones includes dimethylpolysiloxane, methylphenylpolysiloxane, methylpolysiloxane, octamethylcyclotetrasiloxane, decamethylcyclopentasiloxane, dodecamethylcyclohexanesiloxane, methylcyclopolysiloxane, octanemethyltrisiloxane, decamethyltetrasiloxane, polyoxyethylene-methylpolysiloxane copolymer, polyoxypropylene-methylpolysiloxane copolymer, poly(oxymethylene-oxypropylene)methylpolysiloxane copolymer, methylhydrogenpolysiloxane, tetrahydrotetramethylcyclotetrasiloxane, stearoxymethylpolysiloxane, cetoxymethylpolysiloxane, methylpolysiloxane emulsion, high-polymerization methylpolysiloxane, trimethylsiloxysilicic acid, crosslinked methylpolysiloxane, crosslinked methylphenylpolysiloxane, etc.

The moisturizers include, for example, polyalcohols such as glyceryl trioctanoate, maltitol, sorbitol, glycerin, propylene glycol, 1,3-butylene glycol, polyethylene glycol, glycol, etc., organic acids and their salts such as sodium pyrrolidonecarboxylate, sodium lactate, sodium citrate, etc., hyaluronic acid and its salts such as sodium hyaluronate, etc., fermentation metabolites such as hydrolyzates of yeast and yeast extract, yeast culture broth, lactic acid bacteria culture broth, etc., water-soluble proteins such as collagen, elastin, keratin, sericin, etc., collagen hydrolyzates, casein hydrolyzates, silk hydrolyzates, peptides and their salts such as sodium polyaspartate, saccharides, polysaccharides and their derivatives such as trehalose, xylobiose, maltose, sucrose, glucose, vegetable viscous polysaccharides, etc., glycosaminoglycan and its salts such as water-soluble chitin, chitosan, pectin, chondroitin sulfate and its salts, etc., amino acids such as glycine, serine, threonine, alanine, aspartic acid, tyrosine, valine, leucine, arginine, glutamine, proline acid, etc., glycoamino acid compounds such as aminocarbonyl reaction product, etc., vegetable extracts such as aloe extract, horse chestnut extract, trimethylglycine, urea, uric acid, ammonia, lecithin, lanolin, squalane, squalene, glucosamine, creatinine, nucleic acid-related substances such as DNA, RNA, etc. One or more of these may be used here either singly or in combination.

The organic fine particles include, for example, latex emulsion and polyurethane aqueous dispersion to be obtained through emulsion polymerization such as styrene-butadiene copolymer latex, acrylic emulsion, etc. The inorganic fine particles include, for example, those of zeolite, montmorillonite, asbestos, smectite, mica, fumed silica, colloidal silica, titanium oxide, etc. Not detracting the sprayability of the composition, the fine particles are preferably microparticulated ones having a mean particle size of 10 μm or less, more preferably 5 μm or less.

The antiseptics include, for example, methylparaben, ethylparaben, etc.

The deodorants and fragrances include, for example, D-limonene, decyl aldehyde, menthone, pulegone, eugenol, cinnamaldehyde, benzaldehyde, menthol, peppermint oil, lemon oil, orange oil, as well as deodorant effective ingredients extracted from various organs of vegetables (for example, deodorant effective ingredients extracted from oxalis, Korean houttynia, hemlock fir (*Tsuga sieboldii*), gingko, Japanese black pine, larch, Japanese red pine, empress tree, fortune tea olive, lilac, orange osmanthus (sweet tea), giant butterbur, tsuwabuki (*Farfugium japonicum*), forsythia or the like, with water or hydrophilic organic solvent), etc. One or more of these may be used here either singly or in combination.

The organic solvents include, for example, water-soluble alcohols (methanol, ethanol, isopropanol, isobutanoyl, sec-butanol, tert-butanol, methyl cellosolve, ethyl cellosolve, ethylene glycol, glycerin, etc.), ethers (ethylene glycol dimethyl ether, 1,4-dioxane, tetrahydrofuran, etc.), ketones (acetone, methyl ethyl ketone), N,N-dimethylformamide, N,N-dimethylacetamide, dimethyl sulfoxide, etc. One or more of these may be used here either singly or in combination.

The functional additive [component (C")] may be used here either singly or as a mixture of two or more different types of the compound, depending on the utilization field and the necessary performance of the spray composition of the present invention. The amount thereof may be within a suitable range depending on the necessary performance thereof The spray composition of the present invention can be prepared by dispersing the components of the above-mentioned components (A") and (B) [and optionally the component (C") and others], with using various types of dispersing machines. The dispersing machines may be the same as those used in preparing the cellulose fibers of the component (A"). As described above, water (dispersion medium) of the component (B) and the functional additive of the component (C") may be added in preparing the cellulose fibers of the component (A") (through microfibrillation). However, after preparation of the cellulose fibers of the component (A"), water (component B) and the functional additive (component C") may be added thereto, and then dispersed with the above-mentioned dispersing machine. Since the cellulose fibers of the component (A") serve also as an emulsion stabilizer, the cellulose fiber dispersion previously prepared may be mixed with an oil, if added thereto, according to an ordinary method of preparing an O/W emulsion. In this case, a nonionic surfactant or the like serving as an emulsion stabilizer may be additionally used, and the amount of the cellulose fibers may be determined in consideration of the emulsion stability and the sprayability of the composition.

The viscosity of the spray composition of the present invention and the content of the cellulose fibers of the component (A") in the composition are defined to fall within a specific range from the viewpoint of the size of the mother liquid droplets thereof. Specifically, in the present invention, the content of the cellulose fibers of the component (A") is from 0.1 to 3.0% by weight, and the maximum value of the viscosity ($\eta_{max}$) of the composition, which is measured with a cone-plate type rotatory viscometer at 20° C. in a shear rate region including from $1 \times 10^{-3}$ S$^{-1}$ to $1 \times 10^3$ S$^{-1}$, is $\eta_{max} \geq 1 \times 10^4$ mPa·s, which enables the composition show good spray coating with no dripping. In addition, since the minimum value of the viscosity ($\eta_{min}$) of the composition is $\eta_{min} \leq 1 \times 10^2$ mPa·s, the composition can be sprayed as fine mother liquid droplets with no spraying unevenness. Contrary to this, a low-viscosity composition of which the value of $\eta_{max}$ is lower than $1 \times 10^4$ mPa·s could not be expected to prevent the dripping in spraying, and when the value of $\eta_{min}$ is larger than $1 \times 10^2$ mPa·s, then the mother liquid droplets would be large to cause spray unevenness. In case where the coating density in spraying is relatively low, the composition can be fully expected to prevent dripping so far as it satisfies $\eta_{max} \geq 1 \times 10^4$ mPa·s. However, in case of thick spraying, the composition could not still prevent dripping even though satisfying $\eta_{max} \geq 1 \times 10^4$ mPa·s, and consequently, for preventing dripping in any and every spraying condition, the spray composition of the present invention preferably satisfies $\eta_{max} \geq 5 \times 10^4$ mPa·s in order that the composition can sufficiently exhibit the effect thereof. Also in spraying at an ordinary density, there may not occur spray unevenness when the composition satisfies $\eta_{min} \leq 1 \times 10^2$ mPa·s. However, in case of extremely thin and uniform spraying, the composition preferably satisfies $\eta_{min} \leq 5\times10^1$ mPa·s. For enabling stable spraying with the spray composition of the present invention, the value of $\eta_{max}$ of the composition is preferably not larger than $10^9$ mPa·s.

The spray composition of the present invention has high thixotropy. Therefore, when it is sprayed, its viscosity may lower for good spraying, and in addition, after spraying, the viscosity of the coating layer could be immediately restored on the coating surface to prevent dripping from the coated surface. Further, since the viscosity of the spray composition of the present invention does not lower even at a high temperature of 50° C. or higher, the composition is excellent in temperature stability. Consequently, the composition is free from a sticky feeling specific to water-soluble polymers and another excellent property thereof is that the composition can well spread after sprayed.

The spray atomizer to be charged with the spray composition of the present invention may be any one capable of being readily charged with the composition and capable of acting as an atomizer for spraying the composition. However, in consideration of the general versatility and the high accuracy thereof, the atomizer is preferably any of the following embodiments (1) to (3). Specifically, the spray atomizer is charged with the spray composition inside it.

(1) Dispenser-Type Atomizer Equipped with an Atomizable Pump-Type Nozzle:

The atomizer of the type can atomize the spray under atmospheric pressure, without requiring any pressure gas, and the vessel structure thereof is relatively simple and is highly safe. The atomizer of the type is suitable for mobile ones. The structure includes a push pump-type nozzle equipped with a suction tube, and a screw-type vessel that fixes the nozzle and is charged with the composition. The dispenser-type atomizer includes any and every modified one in which the structure of the pump-type nozzle is modified for increasing the atomizing performance. The atomizing performance depends on the orifice size of the jet nozzle and on the dose per one push. These conditions may be suitably selected depending on the intended object.

(2) Trigger-Type Atomizer

The trigger-type atomizer is an atomizer for house cleaners, cloth starches, kitchen cleaners, etc., and includes a pistol-type trigger spraying unit fitted to the mouth of the vessel body to be filled with the composition. The atomizer of the type enables spraying under atmospheric pressure and is very popular for liquid atomizers. The trigger-type atomizer as referred to herein includes any and every modified one in which a part of the trigger-type spray atomizer is modified for enhancing the atomizing performance.

(3) Aerosol-Type Atomizer

By filling a propellant in the container thereof, the aerosol-type atomizer enables continuous atomization or continuous foam formation that could not be realized by the above-mentioned two atomizers. The aerosol-type atomizer as referred to herein includes any and every modified one in which a part of the injector unit of the aerosol-type container is modified. In general, the atomizer of the type enables finer atomization in comparison with the above-mentioned two atomizers to be handled under atmospheric pressure. As the propellant to be used for aerosol atomization, dimethyl ether, liquefied petroleum gas, carbon dioxide, nitrogen gas, argon gas, air, oxygen gas, Freon gas, etc are mentioned. One or more of these may be used here either singly or in combination.

In case of using any of these atomizers, the spray composition of the present invention is used as the mother liquid therein, whereby the content in the atomizer can be in the form of a gel. Inside the container of those atomizers, the mother liquid does not flow and the spray atomizers enables atomization in all directions. In an extreme case, the atomizers enable atomization even when turned upside down, and can therefore favorably function as spraying devices.

EXAMPLES

Next, examples of the cosmetic composition, the gel-type composition and the spray composition are described below in separate sections.

[Examples of Cosmetic Composition]

Examples of the cosmetic composition along with Comparative Examples are firstly described. However, the present invention (cosmetic composition) should not be limited to these Examples.

Prior to Examples and Comparative Examples, cellulose fibers and cellulose fine particles were prepared as follows.

[Production of Cellulose Fibers T1]

To 2 g (dry weight) of softwood pulp, 150 ml of water, 0.025 g of sodium bromide and 0.025 g of TEMPO (N-oxy-radical catalyst) were added and well stirred and dispersed, and then an aqueous 13% by weight sodium hypochlorite solution (co-oxidizing agent) was added thereto in such a manner that the amount of sodium hypochlorite could be 5.4 mmol per gram of pulp, and while an aqueous 0.5 N sodium hydroxide solution was dropwise added thereto so as to keep the pH of the system at from 10 to 11, the reaction was continued until no pH change could be seen (reaction time: 120 minutes). After the reaction, this was neutralized with 0.1 N hydrochloric acid added thereto, and then purified by repletion of filtering and washing with water, thereby giving surface-oxidized cellulose fibers T1.

[Production of Cellulose Fibers T2 to T3, H1 to H2]

Other cellulose fibers were produced in the same manner as the production for the cellulose fibers T1 except that the amount of the aqueous sodium hypochlorite solution to be added and the reaction time were changed as in Table 1 below.

[Production of Cellulose Fibers H3]

Soft wood pulp was immersed overnight in an aqueous 18% sodium hydroxide solution to prepare mercerized cellulose in which the cellulose I-type crystal structure was changed to a cellulose II-type crystal structure, and was used here in place of soft wood pulp, and reacted under the same condition as that for the cellulose fibers T1. The cellulose fibers H3 dissolved during the reaction, and at the end of the reaction, they gave a uniform aqueous solution. The obtained aqueous solution was neutralized to have a pH of from 7 to 8, with aqueous 0.1 N hydrochloric acid solution added thereto, and then left in running water for 10 days through a dialysis cellulose membrane (Spectra/ProCE, fractionation molecular weight, 500) to remove the remaining salts, the unreacted materials and the catalyst. The obtained aqueous solution was freeze-dried to give a powder of cellulose fibers H3.

TABLE 1

| | Cellulose Fibers | | | | | |
|---|---|---|---|---|---|---|
| | for Examples | | | for Comparative Examples | | |
| | T1 | T2 | T3 | H1 | H2 | H3 |
| Amount of aqueous sodium hypochlorite solution (mmol/g) | 5.4 | 4.1 | 12.5 | 3.4 | 20.4 | 25.6 |

TABLE 1-continued

| | Cellulose Fibers | | | | | |
|---|---|---|---|---|---|---|
| | for Examples | | | for Comparative Examples | | |
| | T1 | T2 | T3 | H1 | H2 | H3 |
| Reaction time (min) | 120 | 60 | 120 | 60 | 180 | 120 |
| Amount of carboxyl group (mmol/g) | 1.00 | 0.75 | 1.98 | 0.54 | 2.35 | 5.45 |
| Amount of aldehyde group (mmol/g) | 0.18 | 0.25 | 0.05 | 0.32 | 0.02 | 0.00 |
| Maximum fiber diameter (nm) | 10 | 12 | 10 | 35 | 8 | — |
| Number-average fiber diameter (nm) | 7 | 7 | 6 | 15 | 6 | — |

[Production of Cellulose Fine Particles H4]

According to Example 1 described in JP-A 2000-26229, low-crystalline cellulose fine particles were produced. Specifically, wood pulp having a mean degree of polymerization (DP) of 760 was dissolved in an aqueous 60 wt. % sulfuric acid solution at −5° C. in such a manner that the cellulose concentration could be 4% by weight, to prepare a cellulose dope. The cellulose dope was poured into water (5° C.) in an amount of 2.5 times by weight of the dope with stirring, thereby preparing a suspension of cellulose flocs. After heating up to 80° C., the suspension was hydrolyzed for 10 minutes, and then fully washed with water and water was removed under reduced pressure repeatedly many times until the pH of the wash waste could reach 4 or more to prepare a semitransparent white paste of pasty cellulose fine particles having a cellulose concentration of 6% by weight. The paste was diluted with water to have a cellulose concentration of 5% by weight, and stirred with a blender at a revolution speed of at least 15000 rpm for 5 minutes to give a semitransparent white paste containing low-crystalline cellulose fine particles H4.

The thus-obtained cellulose fibers and cellulose fine particles were analyzed for the following items, according to the criteria mentioned below. The results are shown in the above Table 1.

[Number-Average Fiber Diameter, Maximum Fiber Diameter]

Water was added to the cellulose fibers so that the cellulose solid content could be 1% by weight. It was dispersed, using an ultrahigh-pressure homogenizer (Mizuho Industry's Microfluidizer M-110EH), and then freeze-dried to prepare a sample, followed by observation with a scanning electron microscope (SEM) (JEOL's JSM-6380LV). Based on the image (magnification: 10000) thereof, the number-average fiber diameter and the maximum fiber diameter of the cellulose fibers were measured.

[Amount of Carboxyl Group]

The amount of the carboxyl group in the surface of the cellulose fibers were quantified through potentiometric titration. Specifically, 0.3 g of the dried cellulose fibers were dispersed in 55 ml of water, then 5 ml of an aqueous 0.01 N sodium hydroxide solution was added thereto and well stirred to prepare a dispersion of the cellulose fibers. Next, 0.1 N hydrochloric acid solution was added thereto until the pH of the dispersion could be from 2.5 to 3.0, and then an aqueous 0.04 N sodium hydroxide solution was dropwise added thereto at a speed of 0.1 ml/min. On the obtained pH curve, the amount of the carboxyl group was calculated from the difference between the point of neutralization of the excessive hydrochloric acid and the point of neutralization of the cellulose fibers-derived carboxyl group.

[Amount of Aldehyde Group]

The amount of the aldehyde group in the surface of the cellulose fibers were quantified according to the following method. Specifically, the sample was dispersed in water, and using sodium chlorite under an acid condition with acetic acid, the aldehyde group in the sample was completely oxidized into a carboxyl group, and the amount of the carboxyl group in the resulting sample was measured. The difference between the amount of the carboxyl group in the oxidized sample and that in the sample before oxidation indicates the amount of the aldehyde group in the sample.

[Confirmation on $^{13}$C-NMR Chart]

As to whether or not the hydroxyl group alone at the C6-position in the glucose unit in the surface of the cellulose fibers was selectively oxidized into a carboxyl group, the sample was confirmed on the $^{13}$C-NMR chart thereof. Specifically, the peak at 62 ppm corresponding to the C6-position of the primary hydroxyl group of the glucose unit, which is confirmed on the $^{13}$C-NMR chart of the cellulose before oxidation, disappeared after the oxidation. Alternatively, a peak derived from the carboxyl group appeared at 178 ppm. From this, it was confirmed that, in the cellulose fibers T1 to T3, the C6-position hydroxyl group alone of the glucose unit was oxidized into an aldehyde group and a carboxyl group.

Next, using the cellulose fibers, cosmetic composition of Examples and Comparative Examples were produced.

Example 1A

As shown in Table 2 below, the cellulose fibers T3 in an amount of 1.0% by weight as the solid content thereof, the surfactant A (disodium lauryl polyoxyethylenesulfosuccinate) in an amount of 10% by weight and water in an amount of 89% by weight were mixed, and in vacuum, stirred at a revolution speed of 15,000 rpm or more for 10 minutes to produce a cosmetic composition.

Examples 2A, 3A, Comparative Examples 1A to 4A

Cosmetic compositions were produced in the same manner as in Example 1A except that the constituent components and their amount were changed as in Table 2 below.

TABLE 2

| | Example | | | Comparative Example | | | (% by weight) |
|---|---|---|---|---|---|---|---|
| | 1A | 2A | 3A | 1A | 2A | 3A | 4A |
| Cellulose fibers T3 | 1.0 | 1.0 | 1.0 | — | — | — | — |
| Cellulose fibers H1 | — | — | — | 1.0 | — | — | — |
| Cellulose fibers H2 | — | — | — | — | 1.0 | — | — |
| Cellulose fibers H3 | — | — | — | — | — | 1.0 | — |

TABLE 2-continued (% by weight)

| | | Example | | | Comparative Example | | | |
|---|---|---|---|---|---|---|---|---|
| | | 1A | 2A | 3A | 1A | 2A | 3A | 4A |
| Cellulose fine particles H4 | | — | — | — | — | — | — | 1.5 |
| Surfactant*1 | A | 10 | — | — | 10 | 10 | 10 | — |
| | B | — | 10 | — | — | — | — | — |
| | C | — | — | 10 | — | — | — | 10 |
| Water | | 89 | 89 | 89 | 89 | 89 | 89 | 88.5 |
| Property | | transparent viscous matter | transparent viscous matter | transparent gel | Non transparent viscous matter | Transparent gel | Transparent liquid | Transparent liquid |
| Viscosity (Pa · s) | | 15.2 | 14.7 | 19.8 | 4.8 | 20.8 | 0.06 | 0.2 |
| Dispersion stability | | uniform | uniform | uniform and gel | nonuniform | *2 | uniform | separated |

*1: Surfactant A: disodium lauryl polyoxyethylenesulfosuccinate
Surfactant B: sodium polyoxyethylene alkylether sulfate
Surfactant C: sodium polyoxyethylene laurylether acetate
*2: The viscosity reduced with time and the dispersion became flowable.

Thus obtained, the cosmetic compositions of Examples 1A to 3A and Comparative Examples 1A to 4A were evaluated for the properties thereof according to the criteria mentioned below. The results are shown in the above Table 2.

[Viscosity]

The viscosity of each cosmetic composition was measured with a BH-type viscometer (Rotor No. 4; number of revolutions, 2.5 rpm; 3 minutes, 25° C.).

[Dispersion Stability]

The change with time of the homogeneity of each cosmetic composition after mixing was investigated to evaluate the dispersion stability of the composition. Briefly, each cosmetic composition was left in a closed environment at 40° C. for 10 days, and checked for the condition thereof From the results in the above Table 2, it is known that the compositions of Examples had a high viscosity and were excellent in dispersion stability. In addition, it is confirmed that the compositions of Examples were kept stable for 2 months or more in evaluation of the dispersion stability thereof As opposed to these, the composition of Comparative Example 1A using the cellulose fibers H1 had a low viscosity and became nonhomogeneous in dispersion stability evaluation and was poor in dispersion stability. The composition of Comparative Example 2A using the cellulose fibers H2 had a high viscosity but was poor in dispersion stability. The composition of Comparative Example 3A using the cellulose fibers H3 had an extremely low viscosity; and the composition of Comparative Example 4A using the cellulose fine particles H4 had a low viscosity and separated and was poor in dispersion stability.

Example 1B

Water was added to the cellulose fibers T3 so that the cellulose solid content could be 1% by weight. This was processed one time with a high-pressure disperse (Sugino Machine's Ultimizer HJP-25003, operation pressure 150 MPa) to prepare a transparent gel. Next, as shown in Table 3 below, 30 g of polyoxyethylene glyceryl isostearate, 30 g of silicone oil A (Shin-Etsu Chemical's KF96-100CS) and 30 g of squalane were added to 10 g of the gel, and mixed using a homomixer (Primix's T.K. Robomix, 8,000 rpm×1 min) to produce a cosmetic composition.

Example 2B

A cosmetic composition was produced in the same manner as in Example 1B, except that silicone oil B (Shin-Etsu Chemical's KF995) was used in place of the silicone oil A in Example 1B, as shown in Table 3 below.

Comparative Example 1B

A cosmetic composition was produced in the same manner as in Example 1B, except that water was used in place of the gel in Example 1B, as shown in Table 3 below.

Comparative Example 2B

A cosmetic composition was produced in the same manner as in Example 2B, except that water was used in place of the gel in Example 2B, as shown in Table 3 below.

TABLE 3

(g)

| | Example | | Comparative Example | |
|---|---|---|---|---|
| | 1B | 2B | 1B | 2B |
| Cellulose fibers T3-containing gel | 10 | 10 | — | — |
| Water | — | — | 10 | 10 |
| Polyoxyethylene glyceryl isostearate | 30 | 30 | 30 | 30 |
| Silicon oil A | 30 | — | 30 | — |
| Silicon oil B | — | 30 | — | 30 |
| Squalane | 30 | 30 | 30 | 30 |
| Property | white viscous matter | transparent viscous matter | white viscous matter | transparent viscous matter |
| Viscosity (mPa · s) | 12.4 | 7.6 | 6.8 | 1.9 |
| Sticky feeling | ⊚ | ⊚ | Δ | Δ |
| Rough feeling | ⊚ | ⊚ | ⊚ | ⊚ |
| Dispersion stability | uniform | uniform | partly separated | uniform |

Thus obtained, the cosmetic compositions of Examples 1B and 2B and Comparative Examples 1B and 2B were evaluated for the properties thereof according to the criteria mentioned below. The results are shown in the above Table 3.

[Viscosity]

The viscosity was evaluated according to the same criteria as above.

[Sticky Feeling]

Each cosmetic composition was applied on the upper arm of each of randomly-selected 10 panelists. The composition was evaluated in three stages of (A) not sticky, (B) sticky, and (C) extremely sticky. The samples with which at least 8 panelists gave (A) were ranked as "⊚"; from 5 to 7 panelists as "○"; from 2 to 4 panelists as "Δ"; and at most 1 panelist as "x".

[Rough Feeling]

Each cosmetic composition was applied on the upper arm of each of randomly-selected 10 panelists. The composition was evaluated in three stages of (A) extremely smooth, (B) somewhat rough, and (C) extremely rough. The samples with which at least 8 panelists gave (A) were ranked as "⊚"; from 5 to 7 panelists as "○"; from 2 to 4 panelists as "Δ"; and at most 1 panelist as "x".

[Dispersion Stability]

The compositions were evaluated according to the same criteria as above.

From the results in the above Table 3, it is known that the compositions of Examples 1B and 2B had a high viscosity and were excellent in dispersion stability, and had good results in evaluation of sticky feeling and rough feeling. In addition, it is confirmed that the compositions of Examples 1B and 2B were good in evaluation of dispersion stability, as kept almost stable for 2 months or more.

As opposed to these, the composition of Comparative Example 1B not containing the cellulose fibers T3-containing gel had a lower viscosity than that of the compositions of Examples, had a sticky feeling and was poor in evaluation of dispersion stability. The composition of Comparative Example 2B not containing the cellulose fibers T3-containing gel was good in point of dispersion stability, but had a low viscosity and had a sticky feeling.

Example 1C

As shown in Table 4 below, the cellulose fibers T1 in an amount of 1.0% by weight as the solid content thereof, liquid paraffin in an amount of 20% by weight and glycerin in an amount of 5% by weight were added and dispersed using a homomixer (Primix's T.K. Robomix, 12,000 rpm×10 min) to produce a cosmetic composition.

Examples 2C to 3C

Cosmetic compositions were produced in the same manner as in Example 1C, except that the cellulose fibers T2 and T3, respectively, were used in place of the cellulose fibers T1 in Example 1C, as shown in Table 4 below.

Comparative Example 1C

A cosmetic composition was produced in the same manner as in Example 1C, except that the cellulose fibers T1 in Example 1C were not used but water was used in place of it (the amount of water was increased), as shown in Table 5 below.

Comparative Example 2C

A cosmetic composition was produced in the same manner as in Example 1C, except that hydroxyethyl cellulose (by Tokyo Chemical Industry) was used in place of the cellulose fibers T1 in Example 1C, as shown in Table 5 below.

Comparative Examples 3C to 5C

Cosmetic compositions were produced in the same manner as in Example 1C, except that the cellulose fibers H1 to H3, respectively, were used in place of the cellulose fibers T1 in Example 1C, as shown in Table 5 below.

TABLE 4

| | Example (% by weight) | | |
|---|---|---|---|
| | 1C | 2C | 3C |
| Cellulose fibers T1 | 1.0 | — | — |
| Cellulose fibers T2 | — | 1.0 | — |
| Cellulose fibers T3 | — | — | 1.0 |
| Liquid paraffin | 20 | 20 | 20 |
| Glycerin | 5 | 5 | 5 |
| Water | 74.0 | 74.0 | 74.0 |
| Property | uniform cream | uniform cream | uniform cream |
| Viscosity (mPa·s) | 5.9 | 7.1 | 4.2 |
| Sticky feeling | ⊚ | ⊚ | ○ |
| Rough feeling | ⊚ | ⊚ | ⊚ |
| Dispersion stability | uniform | uniform | uniform |

TABLE 5

| | Comparative Example (% by weight) | | | | |
|---|---|---|---|---|---|
| | 1C | 2C | 3C | 4C | 5C |
| Hydroxyethyl cellulose | — | 2.0 | — | — | — |
| Cellulose fibers T1 | — | — | 1.0 | — | — |
| Cellulose fibers T2 | — | — | — | 1.0 | — |
| Cellulose fibers T3 | — | — | — | — | 1.0 |
| Liquid paraffin | 20 | 20 | 20 | 20 | 20 |
| Glycerin | 5 | 5 | 5 | 5 | 5 |
| Water | 75.0 | 73.0 | 74.0 | 74.0 | 74.0 |
| Property | transparent liquid | transparent liquid | non-transparent liquid | non-transparent liquid | non-transparent liquid |
| Viscosity (mPa·s) | 0.01 | 0.01 | 1.2 | 2.8 | 0.04 |
| Sticky feeling | X | X | Δ | X | X |
| Rough feeling | ○ | ○ | X | ⊚ | ⊚ |
| Dispersion stability | separated | separated | separated | uniform | uniform |

Thus obtained, the cosmetic compositions of Examples 1C to 3C and Comparative Examples 1C to 5C were evaluated for the properties thereof according to the same criteria as above. The results are shown in the above Table 4 and Table 5.

From the results in the above Table 4, it is known that the compositions of Examples had a high viscosity and were excellent in dispersion stability, and had good results in evaluation of sticky feeling and rough feeling. In addition, it is confirmed that the compositions of Examples were good in evaluation of dispersion stability, as kept almost stable for 2 months or more. In particular, the compositions of Examples 1C to 3C using the cellulose fibers T1 to T3 each having a high carboxyl group content had better results in every evaluation.

As opposed to these, the composition of Comparative Example 1C not containing the cellulose fibers T1 had a low viscosity, had a sticky feeling and was poor in evaluation of dispersion stability. The composition of Comparative Example 2C using hydroxyethyl cellulose in place of the cellulose fibers T1 had a low viscosity, had a sticky feeling and was poor in evaluation of dispersion stability. The composition of Comparative Example 3C using the cellulose fibers H1 had a lower viscosity than that of the compositions of Examples, had a sticky feeling and a rough feeling and was poor in evaluation of dispersion stability. The composition of Comparative Example 4C using the cellulose fibers H2 also had a lower viscosity than that of the compositions of Examples, and had a sticky feeling. The composition of Comparative Example 5C using the cellulose fibers H3 had a low viscosity, and had a sticky feeling.

[Examples of Gel-Type Composition]

Examples of the gel-type composition along with Comparative Examples are described next. However, the present invention (gel-type composition) should not be limited to these Examples.

Prior to Examples and Comparative Examples, cellulose fibers S1' to S3' for Examples and cellulose fibers H1' and H2' for Comparative Examples were prepared as follows.

[Production of Cellulose Fibers S1' (for Examples)]

(1) Oxidation Step

Undried sulfite-bleached soft wood pulp (mainly including fibers having a fiber size of more than 1000 nm) in an amount corresponding to 200 g of the dry weight thereof, and 2.5 g of TEMPO and 25 g of sodium bromide were dispersed in 1500 ml of water, and an aqueous 13 wt. % sodium hypochlorite solution was added thereto so that the amount of sodium hypochlorite could be 5.4 mmol relative to 1.0 g of the pulp, and the reaction was started. During the reaction, an aqueous 0.5 M sodium hydroxide solution was kept dropwise added thereto to keep the pH at from 10 to 11, and at the time when no pH change could be seen, the reaction was considered to have ended (reaction time, 120 minutes).

(2) Purification Step

The reaction product was filtered through a glass filter; washed with a sufficient amount of ion-exchanged water; and filtered, and the electric conductivity of the resulting filtrate was measured. At the time when there could be seen no electric conductivity change of the filtrate after repeated washing with water, the purification step was finished. In that manner, water-containing cellulose fibers S1' having a solid content of 15% by weight were produced.

[Production of Cellulose Fibers S2' and S3' (for Examples), and Cellulose Fibers H1' and H2' (for Comparative Examples)]

Cellulose fibers S2', S3', H1' and H2' were produced in the same manner as that for the production of the cellulose fibers S1' except that the amount of sodium hypochlorite to be added and the reaction time were changed as in the following Table 6.

TABLE 6

|  | Cellulose Fibers | | | | |
| --- | --- | --- | --- | --- | --- |
|  | S1' | S2' | S3' | H1' | H2' |
| Amount of sodium hypochlorite (mmol/g) | 5.4 | 4.2 | 10.3 | 3.4 | 15.2 |
| Reaction time (min) | 120 | 120 | 120 | 120 | 180 |
| Maximum fiber diameter (nm) | 10 | 12 | 10 | 35 | 10 |
| Number-average fiber diameter (nm) | 7 | 7 | 6 | 15 | 6 |
| Amount of carboxyl group (mmol/g) | 1.00 | 0.82 | 1.60 | 0.50 | 2.10 |
| Amount of aldehyde group (mmol/g) | 0.18 | 0.23 | 0.08 | 0.36 | 0.03 |
| Sum total of amount of carboxyl group and amount of aldehyde group (mmol/g) | 1.18 | 1.05 | 1.68 | 0.86 | 2.13 |

Thus obtained, the cellulose fibers S1' to S3' and H1' and H2' were analyzed for the following items, according to the criteria mentioned below. The results are shown in the above Table 6.

[Maximum Fiber Diameter, Number-Average Fiber Diameter]

Water was added to each of the above-mentioned cellulose fibers S1' to S3' and H1' and H2' to give a 2 wt. % slurry, and using a disperser-type mixer, followed by fibrillating at a number of revolutions of 8,000 rpm for 10 minutes to observation with a transmission electronic microscope (TEM) (JEOL's JEM-1400) to determine the maximum fiber diameter and the number-average fiber diameter of the cellulose fibers. Specifically, the cellulose fibers were cast onto a hydrophilicated carbon film-coated grid, and stained with 2% uranyl acetate. On the stained negative TEM image (10000-power magnifications) of the sample, the maximum fiber diameter and the number-average fiber diameter of the cellulose fibers were calculated according to the method mentioned above.

[Determination of Amount of Carboxyl Group]

By processing with the above-mentioned disperser-type mixer for about 10 minutes, 60 ml of a slurry was prepared, and its pH was controlled to be about 2.5 with an aqueous 0.1 M hydrochloric acid solution added thereto. An aqueous 0.05 M sodium hydroxide solution was dropwise added thereto, and its electric conductivity was measured. The measurement was continued until the pH could reach about 11. From the amount of sodium hydroxide (V) consumed in the neutralization stage of the weak acid having a gentle change of electric conductivity, the amount 1 of the functional group (the amount of the carboxyl group) was calculated according to the following formula (1). [Numerical Formula]

$$\text{Amount of Functional Group 1 (mmol/g)} = V \text{ (ml)} \times 0.05/(\text{mass of cellulose, g}) \quad (1)$$

[Measurement of Amount of Aldehyde Group]

The cellulose fibers were further oxidized in an aqueous 2% sodium hypochlorite solution, which had been controlled to have a pH of from 4 to 5 with acetic acid, for 48 hours at room temperature (25° C.), and the amount 2 of the functional group was determined according to the above formula (1). With that, the amount of the functional group added by this oxidation (amount of functional group 2—amount of functional group 1) was calculated, and this is the amount of the aldehyde group.

[Confirmation of Cellulose I-Type Crystal Structure, Carboxyl Group and Aldehyde Group]

A part of the slurry was dried to give a transparent cellulose film, and the wide-angle X-ray diffraction image of the film confirmed the presence of the cellulose I-type crystal structure in the fibers. In addition, in the attenuated total IR reflectiometry (ATR) of the sample, the presence of carbonyl group-caused absorption (at around 1608 $cm^{-1}$)

and acid-type carboxyl group (COOH)-caused absorption (at around 1730 cm$^{-1}$) was confirmed.

Examples 1D to 9D, Comparative Examples 1D to 8D

Water was added to each of the cellulose fibers S1' to S3' and H1' and H2' to obtain a slurry having the concentration shown in the following Table 7. Using a disperser-type mixer, the slurry was fibrillated at a number of revolutions of 8,000 rpm for 10 minutes to prepare a sample. In Table 7, the amount of water added (the same shall apply hereinunder) was calculated by subtracting the amount of the cellulose fibers added.

TABLE 7

|  | Cellulose Fibers | | Viscosity | State of Gel | | |
|---|---|---|---|---|---|---|
|  | Concentration (wt. %) | Type | (Pa · s) | after 1 day | after 1 week | after 2 weeks |
| Example 1D | 0.3 | S1' | 21.4 | ○ | ○ | ○ |
| Example 2D | 1 | S1' | 51.5 | ○ | ○ | ○ |
| Example 3D | 5 | S1' | 120 | ○ | ○ | ○ |
| Comparative Example 1D | 0.1 | S1' | 8.6 | x | x | x |
| Comparative Example 2D | 8 | S1' | unpreparable | — | — | — |
| Example 4D | 0.3 | S2' | 23.4 | ○ | ○ | ○ |
| Example 5D | 1 | S2' | 55.6 | ○ | ○ | ○ |
| Example 6D | 5 | S2' | 140 | ○ | ○ | ○ |
| Comparative Example 3D | 0.1 | S2' | 11.2 | x | x | x |
| Comparative Example 4D | 8 | S2' | unpreparable | — | — | — |
| Example 7D | 0.3 | S3' | 20.3 | ○ | ○ | ○ |
| Example 8D | 1 | S3' | 48.6 | ○ | ○ | ○ |
| Example 9D | 5 | S3' | 98.0 | ○ | ○ | ○ |
| Comparative Example 5D | 0.1 | S3' | 5.6 | x | x | x |
| Comparative Example 6D | 8 | S3' | unpreparable | — | — | — |
| Comparative Example 7D | 1 | H1' | 35.3 | separated | — | — |
| Comparative Example 8D | 1 | H2' | 25.6 | ○ | x | x |

Thus obtained, the samples were evaluated for the properties thereof according to the criteria mentioned below. The results are shown in the above Table 7.

[Measurement of Viscosity]

The obtained sample (composition) was left at 25° C. for 24 hours, and then its viscosity was measured with a BH-type viscometer (Rotor No. 4) (Toki Sangyo's BH-type viscometer) at a number of revolutions of 2.5 rpm (3 minutes).

[State of Gel]

Each sample was visually checked for the gel-like state thereof after 1 day, after 1 week and after 2 weeks. Gel-like samples were evaluated as "○"; liquid (flowable) samples were as "x"; and samples separated into gel and water were as "separated".

From the results in the above Table 7, it is known that the compositions of Examples 1D to 9D, in which any of the cellulose fibers S1' to S3' having an aldehyde group content of from 0.08 to 0.3 mmol/g and a carboxyl group content of from 0.6 to 2.0 mmol/g were used and in which the content of the cellulose fibers was from 0.3 to 5.0% by weight, kept gel after stored for 2 weeks.

As opposed to these, the compositions of Comparative Examples 1D, 3D and 5D, in which any of the cellulose fibers S1' to S3' having an aldehyde group content of from 0.08 to 0.3 mmol/g and a carboxyl group content of from 0.6 to 2.0 mmol/g were used and in which the content of the cellulose fibers was lower than the lower limit (0.3% by weight), could not be gel. The compositions of Comparative Examples 2D, 4D and 6D, in which any of the cellulose fibers S1' to S3' having an aldehyde group content of from 0.08 to 0.3 mmol/g and a carboxyl group content of from 0.6 to 2.0 mmol/g were used and in which the content of the cellulose fibers was more than the upper limit (5.0% by weight), could not disperse uniformly since their viscosity was high, and could not also be gel.

In the composition of Comparative Example 7D, in which the cellulose fibers H1' having a carboxyl group content of less than 0.6 mmol/g were used, the cellulose fibers partly settled out and separated after 1 day. The composition of Comparative Example 8D, in which the cellulose fibers H2' having a carboxyl group content of more than 2.0 mmol/g were used, failed to be gel with time and expressed flowability.

Next, using the above-mentioned cellulose fibers, water (liquid dispersion medium) and functional additives (inorganic salts, etc.), gel-type compositions were produced.

Examples 10D to 222D, Comparative Examples 9D to 148D

Water and functional additives (inorganic salts, surfactants, oils, moisturizers, antiseptics, inorganic fine particles, organic fine particles, organic solvents, fragrances, deodorants) shown in the following Table 8 to Table 38 were added to the cellulose fibers S1' to S3' and H1' and H2' in such a manner that the concentration of the cellulose fibers in the resulting slurry could be as in those Table 8 to Table 38, and, using a disperser-type mixer, the slurry was fibrillated at a number of revolutions of 8,000 rpm for 10 minutes, thereby preparing samples. In Table 8 to Table 38, the amount of water added (the same shall apply hereinunder) is calculated by subtracting the amount of the cellulose fibers and that of the functional additives.

Conventional Examples 1D to 27D

The cellulose fibers obtained according to the method described in WO99/28350 were used here. Specifically, a pulp sheet was cut into chips of 5 mm×5 mm to prepare a wood pulp having a degree of polymerization of 760, followed by dissolving in an aqueous 65% sulfuric acid solution at −5° C. in such a manner that the cellulose concentration in the resulting dope could be 5%, with stirring at 150 rpm for 10 minutes to give a transparent uniform cellulose dope. With stirring, the cellulose dope was poured into water (5° C.) in an amount of 2.5 times by weight the dope, to prepare a suspension of cellulose flocs. The suspension was hydrolyzed at 85° C. for 20 minutes, and then fully washed with water and filtered repeatedly many times until the pH of the wash waste could reach 4 or more to prepare white and transparent gel-like cellulose fibers having a cellulose concentration of 15%. The gel product was stirred and homogenized with a household-use food processor (knife cutter) for 3 minutes, and water and functional additives shown in the following Table 39 and Table 40 ([inorganic salts] NaCl, KCl, $CaCl_2$, $MgCl_2$, $(NH_4)_2SO_4$, $Na_2CO_3$, [surfactants] surfactants 1 to 3, [oils] oil 1 to 3, [organic solvents] organic solvent 1, 2) were added thereto to be in the predetermined concentration shown in the Tables, by which the sample was diluted to have a cellulose concentration of 1.5%, followed by further stirring with a blender at a number of revolutions of 15,000 rpm for 5 minutes. Next, the thus-diluted sample was homogenized four times with an ultrahigh-pressure homogenizer (Mizuho Industry's Microfluidizer M-110EH Model, operation pressure 1,750 kg/cm$^2$). The fibrillated cellulose fibers (A1') with water alone added thereto (blank) and processed four times had a mean particle size of 0.18 μm, and the transmittance of the dispersion was 95%.

Conventional Examples 28D to 51D

Using a disperser-type mixer, water and functional additives shown in the following Table 41 ([inorganic salts] NaCl, KCl, $CaCl_2$, $MgCl_2$, $(NH_4)_2SO_4$, $Na_2CO_3$, [surfactants] surfactant 3, [oils] oil 1 to 3, [inorganic fine particles] inorganic fine particles 1, 2) were mixed to prepare an aqueous solution or an aqueous dispersion so as to finally have the predetermined concentration as in the Table. Using a disperser-type stirrer, 0.50 g of carboxyvinyl polymer A2' (BF Goodrich's Carbopol 980 was gradually added to and dispersed in 97.5 g of the above aqueous solution or dispersion, with stirring at a number of revolutions of 8,000 rpm. For neutralization and thickening, 2.0 g of an aqueous 10% sodium hydroxide solution was dropwise added thereto. For fully homogenizing it, the sample was stirred for 10 minutes. The viscosity of the sample formed of water and carboxyvinyl polymer A2' alone (blank) was 61.0 Pa·s.

The functional additives shown in the following Table 8 to Table 41 are as follows.
[Inorganic Salts]
NaCl, KCl, $CaCl_2$, $MgCl_2$, $(NH_4)_2SO_4$, $Na_2CO_3$
[Surfactants]
Polyoxyethylene lauryl ether (surfactant 1)
Alkylpolyglucoside (surfactant 2)
Sodium polyoxyethylene lauryl ether sulfate (surfactant 3)
[Oils]
Dimethylpolysiloxane (oil 1)
Glyceryl triisooctanoate (oil 2)
Squalane (oil 3)
[Moisturizer]
Glycerin
[Antiseptic]
Methylparaben
[Inorganic Fine Particles]
Titanium oxide (inorganic fine particles 1)
Red iron oxide (inorganic fine particles 2)
[Organic Fine particles]
Urethane emulsion (Daiichi Kogyo Seiyaku's Superflex 150)
[Organic Solvents]
Ethanol (organic solvent 1)
Isopropanol (organic solvent 2)
[Fragrances, Deodorants]
D-limonene (fragrance, deodorant 1)
Orange oil (fragrance, deodorant 2)

TABLE 8

[NaCl added (amount 0.1% by weight)]

| | Cellulose Fibers | | Viscosity | State of Gel | | |
|---|---|---|---|---|---|---|
| | Concentration (wt. %) | Type | (Pa · s) | after 1 day | after 1 week | after 2 weeks |
| Example 10D | 0.3 | S1' | 21.0 | ○ | ○ | ○ |
| Example 11D | 1 | S1' | 49.9 | ○ | ○ | ○ |
| Example 12D | 5 | S1' | 105 | ○ | ○ | ○ |
| Comparative Example 9D | 0.1 | S1' | 7.5 | x | x | x |
| Comparative Example 10D | 13 | S1' | unpreparable | — | — | — |
| Example 13D | 0.3 | S2' | 23.5 | ○ | ○ | ○ |
| Example 14D | 1 | S2' | 54.8 | ○ | ○ | ○ |
| Example 15D | 5 | S2' | 120 | ○ | ○ | ○ |
| Comparative | 0.1 | S2' | 10.3 | x | x | x |

TABLE 8-continued

[NaCl added (amount 0.1% by weight)]

| | Cellulose Fibers | | Viscosity | State of Gel | | |
|---|---|---|---|---|---|---|
| | Concentration (wt. %) | Type | (Pa · s) | after 1 day | after 1 week | after 2 weeks |
| Example 11D Comparative Example 12D | 8 | S2' | unpreparable | — | — | — |
| Example 16D | 0.3 | S3' | 20.5 | ○ | ○ | ○ |
| Example 17D | 1 | S3' | 47.3 | ○ | ○ | ○ |
| Example 18D | 5 | S3' | 105 | ○ | ○ | ○ |
| Comparative Example 13D | 0.1 | S3' | 4.8 | x | x | x |
| Comparative Example 14D | 8 | S3' | unpreparable | — | — | — |
| Comparative Example 15D | 1 | H1' | 32.5 | separated | — | — |
| Comparative Example 16D | 1 | H2' | 21.6 | ○ | x | x |

TABLE 9

[NaCl added (amount 0.1% by weight)]

| | Cellulose Fibers | | Viscosity | State of Gel | | |
|---|---|---|---|---|---|---|
| | Concentration (wt. %) | Type | (Pa · s) | after 1 day | after 1 week | after 2 weeks |
| Example 19D | 0.3 | S1' | 20.8 | ○ | ○ | ○ |
| Example 20D | 1 | S1' | 49.5 | ○ | ○ | ○ |
| Example 21D | 5 | S1' | 99 | ○ | ○ | ○ |
| Comparative Example 17D | 0.1 | S1' | 5.5 | x | x | x |
| Comparative Example 18D | 8 | S1' | unpreparable | — | — | — |
| Example 22D | 0.3 | S2' | 21.2 | ○ | ○ | ○ |
| Example 23D | 1 | S2' | 53.8 | ○ | ○ | ○ |
| Example 24D | 5 | S2' | 135 | ○ | ○ | ○ |
| Comparative Example 19D | 0.1 | S2' | 7.8 | x | x | x |
| Comparative Example 20D | 8 | S2' | unpreparable | — | — | — |
| Example 25D | 0.3 | S3' | 20.1 | ○ | ○ | ○ |
| Example 26D | 1 | S3' | 46.5 | ○ | ○ | ○ |
| Example 27D | 5 | S3' | 118 | ○ | ○ | ○ |
| Comparative Example 21D | 0.1 | S3' | 3.5 | x | x | x |
| Comparative Example 22D | 11 | S3' | unpreparable | — | — | — |

TABLE 10

[KCl added (amount 0.1% by weight)]

| | Cellulose Fibers | | Viscosity | State of Gel | | |
|---|---|---|---|---|---|---|
| | Concentration (wt. %) | Type | (Pa · s) | after 1 day | after 1 week | after 2 weeks |
| Example 28D | 1 | S1' | 48.8 | ○ | ○ | ○ |
| Example 29D | 1 | S2' | 52.8 | ○ | ○ | ○ |
| Example 30D | 1 | S3' | 44.6 | ○ | ○ | ○ |

TABLE 11

[CaCl₂ added (amount 0.1% by weight)]

| | Cellulose Fibers | | Viscosity | State of Gel | | |
|---|---|---|---|---|---|---|
| | Concentration (wt. %) | Type | (Pa · s) | after 1 day | after 1 week | after 2 weeks |
| Example 31D | 1 | S1' | 48.7 | ○ | ○ | ○ |
| Example 32D | 1 | S2' | 59.5 | ○ | ○ | ○ |
| Example 33D | 1 | S3' | 50.2 | ○ | ○ | ○ |

TABLE 12

[MgCl₂ added (amount 0.1% by weight)]

| | Cellulose Fibers | | Viscosity | State of Gel | | |
|---|---|---|---|---|---|---|
| | Concentration (wt. %) | Type | (Pa · s) | after 1 day | after 1 week | after 2 weeks |
| Example 34D | 1 | S1' | 47.3 | ○ | ○ | ○ |
| Example 35D | 1 | S2' | 55.8 | ○ | ○ | ○ |
| Example 36D | 1 | S3' | 51.2 | ○ | ○ | ○ |

TABLE 13

[(NH₄)₂SO₄ added (amount 0.1% by weight)]

| | Cellulose Fibers | | Viscosity | State of Gel | | |
|---|---|---|---|---|---|---|
| | Concentration (wt. %) | Type | (Pa · s) | after 1 day | after 1 week | after 2 weeks |
| Example 37D | 1 | S1' | 49.9 | ○ | ○ | ○ |
| Example 38D | 1 | S2' | 55.3 | ○ | ○ | ○ |
| Example 39D | 1 | S3' | 48.9 | ○ | ○ | ○ |

TABLE 14

[Na₂CO₃ added (amount 0.1% by weight)]

| | Cellulose Fibers | | Viscosity | State of Gel | | |
|---|---|---|---|---|---|---|
| | Concentration (wt. %) | Type | (Pa · s) | after 1 day | after 1 week | after 2 weeks |
| Example 40D | 1 | S1' | 42.6 | ○ | ○ | ○ |
| Example 41D | 1 | S2' | 45.6 | ○ | ○ | ○ |
| Example 42D | 1 | S3' | 41.5 | ○ | ○ | ○ |

TABLE 15

[Polyoxyethylene lauryl ether (activator 1) added (amount 1.0% by weight)]

| | Cellulose Fibers | | Viscosity | State of Gel | | |
|---|---|---|---|---|---|---|
| | Concentration (wt. %) | Type | (Pa · s) | after 1 day | after 1 week | after 2 weeks |
| Example 43D | 0.3 | S1' | 21.0 | ○ | ○ | ○ |
| Example 44D | 1 | S1' | 48.7 | ○ | ○ | ○ |
| Example 45D | 5 | S1' | 107 | ○ | ○ | ○ |
| Comparative Example 23D | 0.1 | S1' | 7.5 | x | x | x |
| Comparative Example 24D | 8 | S1' | unpreparable | — | — | — |

TABLE 15-continued

[Polyoxyethylene lauryl ether (activator 1) added (amount 1.0% by weight)]

| | Cellulose Fibers | | Viscosity | State of Gel | | |
|---|---|---|---|---|---|---|
| | Concentration (wt. %) | Type | (Pa · s) | after 1 day | after 1 week | after 2 weeks |
| Example 46D | 0.3 | S2' | 23.6 | ○ | ○ | ○ |
| Example 47D | 1 | S2' | 51.5 | ○ | ○ | ○ |
| Example 48D | 5 | S2' | 125 | ○ | ○ | ○ |
| Comparative Example 25D | 0.1 | S2' | 10.5 | x | x | x |
| Comparative Example 26D | 8 | S2' | unpreparable | — | — | — |
| Example 49D | 0.3 | S3' | 20.1 | ○ | ○ | ○ |
| Example 50D | 1 | S3' | 46.2 | ○ | ○ | ○ |
| Example 51D | 5 | S3' | 107 | ○ | ○ | ○ |
| Comparative Example 27D | 0.1 | S3' | 5.0 | x | x | x |
| Comparative Example 28D | 8 | S3' | unpreparable | — | — | — |
| Comparative Example 29D | 1 | H1' | 34.5 | separated | — | — |
| Comparative Example 30D | 1 | H2' | 13.5 | x | x | x |

TABLE 16

[Polyoxyethylene lauryl ether (activator 1) added (amount 3.0% by weight)]

| | Cellulose Fibers | | Viscosity | State of Gel | | |
|---|---|---|---|---|---|---|
| | Concentration (wt. %) | Type | (Pa · s) | after 1 day | after 1 week | after 2 weeks |
| Example 52D | 0.3 | S1' | 21.0 | ○ | ○ | ○ |
| Example 53D | 1 | S1' | 42.6 | ○ | ○ | ○ |
| Example 54D | 5 | S1' | 98.0 | ○ | ○ | ○ |
| Comparative Example 31D | 0.1 | S1' | 7.2 | x | x | x |
| Comparative Example 32D | 8 | S1' | unpreparable | — | — | — |
| Example 55D | 0.3 | S2' | 22.3 | ○ | ○ | ○ |
| Example 56D | 1 | S2' | 49.5 | ○ | ○ | ○ |
| Example 57D | 5 | S2' | 105 | ○ | ○ | ○ |
| Comparative Example 33D | 0.1 | S2' | 8.6 | x | x | x |
| Comparative Example 34D | 8 | S2' | unpreparable | — | — | — |
| Example 58D | 0.3 | S3' | 18.5 | ○ | ○ | ○ |
| Example 59D | 1 | S3' | 43.0 | ○ | ○ | ○ |
| Example 60D | 5 | S3' | 95.0 | ○ | ○ | ○ |
| Comparative Example 35D | 0.1 | S3' | 4.2 | x | x | x |
| Comparative Example 35D | 8 | S3' | unpreparable | — | — | — |

TABLE 17

[Alkylpolyglucoside (activator 2) added (amount 3.0% by weight)]

| | Cellulose Fibers | | Viscosity | State of Gel | | |
|---|---|---|---|---|---|---|
| | Concentration (wt. %) | Type | (Pa·s) | after 1 day | after 1 week | after 2 weeks |
| Example 61D | 1 | S1' | 40.6 | ○ | ○ | ○ |
| Example 62D | 1 | S2' | 51.5 | ○ | ○ | ○ |
| Example 63D | 1 | S3' | 38.4 | ○ | ○ | ○ |

TABLE 18

[Sodium polyoxyethylene lauryl ether sulfate (activator 3) added (amount 1.0% by weight)]

| | Cellulose Fibers | | Viscosity | State of Gel | | |
|---|---|---|---|---|---|---|
| | Concentration (wt. %) | Type | (Pa·s) | after 1 day | after 1 week | after 2 weeks |
| Example 64D | 0.3 | S1' | 18.5 | ○ | ○ | ○ |
| Example 65D | 1 | S1' | 43.0 | ○ | ○ | ○ |
| Example 66D | 5 | S1' | 105 | ○ | ○ | ○ |
| Comparative Example 37D | 0.1 | S1' | 1.5 | x | x | x |
| Comparative Example 38D | 8 | S1' | unpreparable | — | — | — |
| Example 67D | 0.3 | S2' | 20.4 | ○ | ○ | ○ |
| Example 68D | 1 | S2' | 48.5 | ○ | ○ | ○ |
| Example 69D | 5 | S2' | 103 | ○ | ○ | ○ |
| Comparative Example 39D | 0.1 | S2' | 2.5 | x | x | x |
| Comparative Example 40D | 11 | S2' | unpreparable | — | — | — |
| Example 70D | 0.3 | S3' | 17.6 | ○ | ○ | ○ |
| Example 71D | 1 | S3' | 43.5 | ○ | ○ | ○ |
| Example 72D | 5 | S3' | 98.0 | ○ | ○ | ○ |
| Comparative Example 41D | 0.1 | S3' | 1.2 | x | x | x |
| Comparative Example 42D | 8 | S3' | unpreparable | — | — | — |
| Comparative Example 43D | 1 | H1' | 30.6 | separated | — | — |
| Comparative Example 44D | 1 | H2' | 14.3 | x | x | x |

TABLE 19

[Sodium polyoxyethylene lauryl ether sulfate (activator 3) added (amount 3.0% by weight)]

| | Cellulose Fibers | | Viscosity | State of Gel | | |
|---|---|---|---|---|---|---|
| | Concentration (wt. %) | Type | (Pa·s) | after 1 day | after 1 week | after 2 weeks |
| Example 73D | 0.3 | S1' | 19.0 | ○ | ○ | ○ |
| Example 74D | 1 | S1' | 38.6 | ○ | ○ | ○ |
| Example 75D | 5 | S1' | 86.0 | ○ | ○ | ○ |
| Comparative Example 45D | 0.1 | S1' | 1.3 | x | x | x |
| Comparative Example 46D | 8 | S1' | unpreparable | — | — | — |
| Example 76D | 0.3 | S2' | 20.1 | ○ | ○ | ○ |
| Example 77D | 1 | S2' | 46.3 | ○ | ○ | ○ |
| Example 78D | 5 | S2' | 90.5 | ○ | ○ | ○ |
| Comparative Example 47D | 0.1 | S2' | 1.8 | x | x | x |

TABLE 19-continued

[Sodium polyoxyethylene lauryl ether sulfate (activator 3) added (amount 3.0% by weight)]

| | Cellulose Fibers | | Viscosity (Pa·s) | State of Gel | | |
|---|---|---|---|---|---|---|
| | Concentration (wt. %) | Type | | after 1 day | after 1 week | after 2 weeks |
| Comparative Example 48D | 8 | S2' | unpreparable | — | — | — |
| Example 79D | 0.3 | S3' | 16.5 | ○ | ○ | ○ |
| Example 80D | 1 | S3' | 41.5 | ○ | ○ | ○ |
| Example 81D | 5 | S3' | 88.0 | ○ | ○ | ○ |
| Comparative Example 49D | 0.1 | S3' | 1.0 | x | x | x |
| Comparative Example 50D | 11 | S3' | unpreparable | — | — | — |

TABLE 20

[Dimethylpolysiloxane (oil 1) added (amount 10% by weight)]

| | Cellulose Fibers | | Viscosity (Pa·s) | State of Gel | | |
|---|---|---|---|---|---|---|
| | Concentration (wt. %) | Type | | after 1 day | after 1 week | after 2 weeks |
| Example 82D | 0.3 | S1' | 30.5 | ○ | ○ | ○ |
| Example 83D | 1 | S1' | 50.5 | ○ | ○ | ○ |
| Example 84D | 5 | S1' | 110 | ○ | ○ | ○ |
| Comparative Example 51D | 0.1 | S1' | 17.5 | x | x | x |
| Comparative Example 52D | 8 | S1' | unpreparable | — | — | — |
| Example 85D | 0.3 | S2' | 32.0 | ○ | ○ | ○ |
| Example 86D | 1 | S2' | 55.5 | ○ | ○ | ○ |
| Example 87D | 5 | S2' | 140 | ○ | ○ | ○ |
| Comparative Example 53D | 0.1 | S2' | 18.0 | x | x | x |
| Comparative Example 54D | 8 | S2' | unpreparable | — | — | — |
| Example 88D | 0.3 | S3' | 28.6 | ○ | ○ | ○ |
| Example 89D | 1 | S3' | 49.5 | ○ | ○ | ○ |
| Example 90D | 5 | S3' | 110 | ○ | ○ | ○ |
| Comparative Example 55D | 0.1 | S3' | 16.0 | x | x | x |
| Comparative Example 56D | 8 | S3' | unpreparable | — | — | — |
| Comparative Example 57D | 1 | H1' | 38.5 | separated | — | — |
| Comparative Example 58D | 1 | H2' | 13.0 | x | x | x |

TABLE 21

[Dimethylpolysiloxane (oil 1) added (amount 33% by weight)]

| | Cellulose Fibers | | Viscosity (Pa·s) | State of Gel | | |
|---|---|---|---|---|---|---|
| | Concentration (wt. %) | Type | | after 1 day | after 1 week | after 2 weeks |
| Example 91D | 0.3 | S1' | 28.6 | ○ | ○ | ○ |
| Example 92D | 1 | S1' | 47.0 | ○ | ○ | ○ |
| Example 93D | 5 | S1' | 100 | ○ | ○ | ○ |
| Comparative Example 59D | 0.1 | S1' | 18.0 | x | x | x |
| Comparative Example 60D | 8 | S1' | unpreparable | — | — | — |
| Example 94D | 0.3 | S2' | 30.5 | ○ | ○ | ○ |
| Example 95D | 1 | S2' | 50.0 | ○ | ○ | ○ |
| Example 96D | 5 | S2' | 120 | ○ | ○ | ○ |
| Comparative Example 61D | 0.1 | S2' | 18.0 | x | x | x |
| Comparative Example 62D | 8 | S2' | unpreparable | — | — | — |
| Example 97D | 0.3 | S3' | 27.0 | ○ | ○ | ○ |
| Example 98D | 1 | S3' | 45.0 | ○ | ○ | ○ |
| Example 99D | 5 | S3' | 105 | ○ | ○ | ○ |
| Comparative Example 63D | 0.1 | S3' | 16.0 | x | x | x |
| Comparative Example 64D | 8 | S3' | unpreparable | — | — | — |

TABLE 22

[Glyceryl triisooctanoate (oil 2) added (amount 33% by weight)]

| | Cellulose Fibers | | Viscosity (Pa·s) | State of Gel | | |
|---|---|---|---|---|---|---|
| | Concentration (wt. %) | Type | | after 1 day | after 1 week | after 2 weeks |
| Example 100D | 1 | S1' | 45.0 | ○ | ○ | ○ |
| Example 101D | 1 | S2' | 48.0 | ○ | ○ | ○ |
| Example 102D | 1 | S3' | 44.0 | ○ | ○ | ○ |

TABLE 23

[Squalane (oil 3) added (amount 33% by weight)]

| | Cellulose Fibers | | Viscosity (Pa·s) | State of Gel | | |
|---|---|---|---|---|---|---|
| | Concentration (wt. %) | Type | | after 1 day | after 1 week | after 2 weeks |
| Example 103D | 1 | S1' | 49.5 | ○ | ○ | ○ |
| Example 104D | 1 | S2' | 52.0 | ○ | ○ | ○ |
| Example 105D | 1 | S3' | 48.0 | ○ | ○ | ○ |

TABLE 24

[Glycerin added (amount 10% by weight)]

| | Cellulose Fibers | | | State of Gel | | |
|---|---|---|---|---|---|---|
| | Concentration (wt. %) | Type | Viscosity (Pa · s) | after 1 day | after 1 week | after 2 weeks |
| Example 106D | 0.3 | S1' | 18.5 | ○ | ○ | ○ |
| Example 107D | 1 | S1' | 52.0 | ○ | ○ | ○ |
| Example 108D | 5 | S1' | 120 | ○ | ○ | ○ |
| Comparative Example 65D | 0.1 | S1' | 8.9 | x | x | x |
| Comparative Example 66D | 8 | S1' | un-preparable | — | — | — |
| Example 109D | 0.3 | S2' | 20.2 | ○ | ○ | ○ |
| Example 110D | 1 | S2' | 57.0 | ○ | ○ | ○ |
| Example 111D | 5 | S2' | 150 | ○ | ○ | ○ |
| Comparative Example 67D | 0.1 | S2' | 10.0 | x | x | x |
| Comparative Example 68D | 8 | S2' | un-preparable | — | — | — |
| Example 112D | 0.3 | S3' | 16.0 | ○ | ○ | ○ |
| Example 113D | 1 | S3' | 51.0 | ○ | ○ | ○ |
| Example 114D | 5 | S3' | 120 | ○ | ○ | ○ |
| Comparative Example 69D | 0.1 | S3' | 7.0 | x | x | x |
| Comparative Example 70D | 8 | S3' | un-preparable | — | — | — |
| Comparative Example 71D | 1 | H1' | 38.0 | separated | — | — |
| Comparative Example 72D | 1 | H2' | 12.0 | x | x | x |

TABLE 25

[Glycerin added (amount 33% by weight)]

| | Cellulose Fibers | | | State of Gel | | |
|---|---|---|---|---|---|---|
| | Concentration (wt. %) | Type | Viscosity (Pa · s) | after 1 day | after 1 week | after 2 weeks |
| Example 115D | 0.3 | S1' | 17.0 | ○ | ○ | ○ |
| Example 116D | 1 | S1' | 50.0 | ○ | ○ | ○ |
| Example 117D | 5 | S1' | 120 | ○ | ○ | ○ |
| Comparative Example 73D | 0.1 | S1' | 9.0 | x | x | x |
| Comparative Example 74D | 8 | S1' | un-preparable | — | — | — |
| Example 118D | 0.3 | S2' | 19.0 | ○ | ○ | ○ |
| Example 119D | 1 | S2' | 51.0 | ○ | ○ | ○ |
| Example 120D | 5 | S2' | 130 | ○ | ○ | ○ |
| Comparative Example 75D | 0.1 | S2' | 11.5 | x | x | x |
| Comparative Example 76D | 8 | S2' | un-preparable | — | — | — |
| Example 121D | 0.3 | S3' | 17.0 | ○ | ○ | ○ |
| Example 122D | 1 | S3' | 48.0 | ○ | ○ | ○ |
| Example 123D | 5 | S3' | 120 | ○ | ○ | ○ |
| Comparative Example 77D | 0.1 | S3' | 8.4 | x | x | x |
| Comparative Example 78D | 8 | S3' | un-preparable | — | — | — |

TABLE 26

[Methylparaben added (amount 0.3% by weight)]

| | Cellulose Fibers | | | State of Gel | | |
|---|---|---|---|---|---|---|
| | Concentration (wt. %) | Type | Viscosity (Pa · s) | after 1 day | after 1 week | after 2 weeks |
| Example 124D | 0.3 | S1' | 21.0 | ○ | ○ | ○ |
| Example 125D | 1 | S1' | 51.5 | ○ | ○ | ○ |
| Example 126D | 5 | S1' | 130 | ○ | ○ | ○ |
| Comparative Example 79D | 0.1 | S1' | 8.5 | x | x | x |
| Comparative Example 80D | 8 | S1' | un-preparable | — | — | — |
| Example 127D | 0.3 | S2' | 24.0 | ○ | ○ | ○ |
| Example 128D | 1 | S2' | 55.5 | ○ | ○ | ○ |
| Example 129D | 5 | S2' | 140 | ○ | ○ | ○ |
| Comparative Example 81D | 0.1 | S2' | 11.0 | x | x | x |
| Comparative Example 82D | 8 | S2' | un-preparable | — | — | — |
| Example 130D | 0.3 | S3' | 21.0 | ○ | ○ | ○ |
| Example 131D | 1 | S3' | 49.0 | ○ | ○ | ○ |
| Example 132D | 5 | S3' | 110 | ○ | ○ | ○ |
| Comparative Example 83D | 0.1 | S3' | 5.0 | x | x | x |
| Comparative Example 84D | 8 | S3' | un-preparable | — | — | — |
| Comparative Example 85D | 1 | H1' | 35.5 | separated | — | — |
| Comparative Example 86D | 1 | H2' | 54.8 | ○ | x | x |

TABLE 27

[Methylparaben added (amount 0.5% by weight)]

| | Cellulose Fibers | | | State of Gel | | |
|---|---|---|---|---|---|---|
| | Concentration (wt. %) | Type | Viscosity (Pa · s) | after 1 day | after 1 week | after 2 weeks |
| Example 133D | 0.3 | S1' | 21.0 | ○ | ○ | ○ |
| Example 134D | 1 | S1' | 51.5 | ○ | ○ | ○ |
| Example 135D | 5 | S1' | 100 | ○ | ○ | ○ |
| Comparative Example 87D | 0.1 | S1' | 8.5 | x | x | x |
| Comparative Example 88D | 8 | S1' | un-preparable | — | — | — |
| Example 136D | 0.3 | S2' | 24.0 | ○ | ○ | ○ |
| Example 137D | 1 | S2' | 55.5 | ○ | ○ | ○ |
| Example 138D | 5 | S2' | 110 | ○ | ○ | ○ |
| Comparative Example 89D | 0.1 | S2' | 11.0 | x | x | x |
| Comparative Example 90D | 8 | S2' | un-preparable | — | — | — |
| Example 139D | 0.3 | S3' | 21.0 | ○ | ○ | ○ |
| Example 140D | 1 | S3' | 49.0 | ○ | ○ | ○ |
| Example 141D | 5 | S3' | 98 | ○ | ○ | ○ |
| Comparative Example 91D | 0.1 | S3' | 5.0 | x | x | x |
| Comparative Example 92D | 8 | S3' | un-preparable | — | — | — |

TABLE 28

[Titanium oxide (inorganic fine particles 1) added (amount 2.0% by weight)]

| | Cellulose Fibers | | | State of Gel | | |
|---|---|---|---|---|---|---|
| | Concentration (wt. %) | Type | Viscosity (Pa·s) | after 1 day | after 1 week | after 2 weeks |
| Example 142D | 0.3 | S1' | 22.0 | ○ | ○ | ○ |
| Example 143D | 1 | S1' | 52.0 | ○ | ○ | ○ |
| Example 144D | 5 | S1' | 105 | ○ | ○ | ○ |
| Comparative Example 93D | 0.1 | S1' | 9.0 | x | x | x |
| Comparative Example 93D | 8 | S1' | un-preparable | — | — | — |
| Example 145D | 0.3 | S2' | 24.0 | ○ | ○ | ○ |
| Example 146D | 1 | S2' | 57.0 | ○ | ○ | ○ |
| Example 147D | 5 | S2' | 120 | ○ | ○ | ○ |
| Comparative Example 95D | 0.1 | S2' | 12.0 | x | x | x |
| Comparative Example 96D | 8 | S2' | un-preparable | — | — | — |
| Example 148D | 0.3 | S3' | 21.0 | ○ | ○ | ○ |
| Example 149D | 1 | S3' | 48.0 | ○ | ○ | ○ |
| Example 150D | 5 | S3' | 100 | ○ | ○ | ○ |
| Comparative Example 97D | 0.1 | S3' | 7.0 | x | x | x |
| Comparative Example 98D | 8 | S3' | un-preparable | — | — | — |
| Comparative Example 99D | 1 | H1' | 36.0 | separated | — | — |
| Comparative Example 100D | 1 | H2' | 26.0 | ○ | x | x |

TABLE 29

[Titanium oxide (inorganic fine particles 1) added (amount 20.0% by weight)]

| | Cellulose Fibers | | | State of Gel | | |
|---|---|---|---|---|---|---|
| | Concentration (wt. %) | Type | Viscosity (Pa·s) | after 1 day | after 1 week | after 2 weeks |
| Example 151D | 0.3 | S1' | 23.0 | ○ | ○ | ○ |
| Example 152D | 1 | S1' | 53.0 | ○ | ○ | ○ |
| Example 153D | 5 | S1' | 110 | ○ | ○ | ○ |
| Comparative Example 101D | 0.1 | S1' | 10.0 | x | x | x |
| Comparative Example 102D | 8 | S1' | un-preparable | — | — | — |
| Example 154D | 0.3 | S2' | 26.0 | ○ | ○ | ○ |
| Example 155D | 1 | S2' | 58.0 | ○ | ○ | ○ |
| Example 156D | 5 | S2' | 140 | ○ | ○ | ○ |
| Comparative Example 103D | 0.1 | S2' | 11.0 | x | x | x |
| Comparative Example 104D | 8 | S2' | un-preparable | — | — | — |
| Example 157D | 0.3 | S3' | 22.0 | ○ | ○ | ○ |
| Example 158D | 1 | S3' | 49.0 | ○ | ○ | ○ |
| Example 159D | 5 | S3' | 100 | ○ | ○ | ○ |
| Comparative Example 105D | 0.1 | S3' | 9.0 | x | x | x |
| Comparative Example 106D | 8 | S3' | un-preparable | — | — | — |

TABLE 30

[Red iron oxide (inorganic fine particles 2) added (amount 20.0% by weight)]

| | Cellulose Fibers | | | State of Gel | | |
|---|---|---|---|---|---|---|
| | Concentration (wt. %) | Type | Viscosity (Pa·s) | after 1 day | after 1 week | after 2 weeks |
| Example 160D | 1 | S1' | 53.0 | ○ | ○ | ○ |
| Example 161D | 1 | S2' | 58.0 | ○ | ○ | ○ |
| Example 162D | 1 | S3' | 48.0 | ○ | ○ | ○ |

TABLE 31

[Urethane emulsion added (amount 2.0% by weight)]

| | Cellulose Fibers | | | State of Gel | | |
|---|---|---|---|---|---|---|
| | Concentration (wt. %) | Type | Viscosity (Pa·s) | after 1 day | after 1 week | after 2 weeks |
| Example 163D | 0.3 | S1' | 21.0 | ○ | ○ | ○ |
| Example 164D | 1 | S1' | 52.0 | ○ | ○ | ○ |
| Example 165D | 5 | S1' | 110 | ○ | ○ | ○ |
| Comparative Example 107D | 0.1 | S1' | 9.0 | x | x | x |
| Comparative Example 108D | 8 | S1' | un-preparable | — | — | — |
| Example 166D | 0.3 | S2' | 24.0 | ○ | ○ | ○ |
| Example 167D | 1 | S2' | 57.0 | ○ | ○ | ○ |
| Example 168D | 5 | S2' | 140 | ○ | ○ | ○ |
| Comparative Example 109D | 0.1 | S2' | 10.0 | x | x | x |
| Comparative Example 110D | 8 | S2' | un-preparable | — | — | — |
| Example 169D | 0.3 | S3' | 21.0 | ○ | ○ | ○ |
| Example 170D | 1 | S3' | 49.0 | ○ | ○ | ○ |
| Example 171D | 5 | S3' | 100 | ○ | ○ | ○ |
| Comparative Example 111D | 0.1 | S3' | 4.0 | x | x | x |
| Comparative Example 112D | 8 | S3' | un-preparable | — | — | — |
| Comparative Example 113D | 1 | H1' | 35.0 | separated | — | — |
| Comparative Example 114D | 1 | H2' | 23.0 | ○ | x | x |

TABLE 32

[Urethane emulsion added (amount 20.0% by weight)]

| | Cellulose Fibers | | | State of Gel | | |
|---|---|---|---|---|---|---|
| | Concentration (wt. %) | Type | Viscosity (Pa·s) | after 1 day | after 1 week | after 2 weeks |
| Example 172D | 0.3 | S1' | 18.0 | ○ | ○ | ○ |
| Example 173D | 1 | S1' | 48.0 | ○ | ○ | ○ |
| Example 174D | 5 | S1' | 110 | ○ | ○ | ○ |
| Comparative Example 115D | 0.1 | S1' | 5.5 | x | x | x |
| Comparative Example 116D | 8 | S1' | unpreparable | — | — | — |
| Example 175D | 0.3 | S2' | 20.0 | ○ | ○ | ○ |
| Example 176D | 1 | S2' | 52.0 | ○ | ○ | ○ |
| Example 177D | 5 | S2' | 130 | ○ | ○ | ○ |
| Comparative Example 117D | 0.1 | S2' | 7.8 | x | x | x |
| Comparative Example 118D | 8 | S2' | unpreparable | — | — | — |
| Example 178D | 0.3 | S3' | 17.0 | ○ | ○ | ○ |
| Example 179D | 1 | S3' | 41.0 | ○ | ○ | ○ |
| Example 180D | 5 | S3' | 100 | ○ | v | ○ |
| Comparative Example 119D | 0.1 | S3' | 3.2 | x | x | x |
| Comparative Example 120D | 8 | S3' | unpreparable | — | — | — |

TABLE 33

[Ethanol (organic acid 1) added (amount 10.0% by weight)]

| | Cellulose Fibers | | | State of Gel | | |
|---|---|---|---|---|---|---|
| | Concentration (wt. %) | Type | Viscosity (Pa·s) | after 1 day | after 1 week | after 2 weeks |
| Example 181D | 0.3 | S1' | 18.5 | ○ | ○ | ○ |
| Example 182D | 1 | S1' | 48.0 | ○ | ○ | ○ |
| Example 183D | 5 | S1' | 100 | ○ | ○ | ○ |
| Comparative Example 121D | 0.1 | S1' | 5.6 | x | x | x |
| Comparative Example 122D | 8 | S1' | unpreparable | — | — | — |
| Example 184D | 0.3 | S2' | 20.5 | ○ | ○ | ○ |
| Example 185D | 1 | S2' | 52.0 | ○ | ○ | ○ |
| Example 186D | 5 | S2' | 140 | ○ | ○ | ○ |
| Comparative Example 123D | 0.1 | S2' | 8.6 | x | x | x |
| Comparative Example 124D | 8 | S2' | unpreparable | — | — | — |
| Example 187D | 0.3 | S3' | 16.0 | ○ | ○ | ○ |
| Example 188D | 1 | S3' | 45.0 | ○ | ○ | ○ |
| Example 189D | 5 | S3' | 100 | ○ | ○ | ○ |
| Comparative Example 125D | 0.1 | S3' | 3.2 | x | x | x |
| Comparative Example 126D | 8 | S3' | unpreparable | — | — | — |
| Comparative Example 127D | 1 | H1' | 33.05 | separated | — | — |
| Comparative Example 128D | 1 | H2' | 23.0 | ○ | x | x |

TABLE 34

[Ethanol (organic acid 1) added (amount 33.0% by weight)]

| | Cellulose Fibers | | | State of Gel | | |
|---|---|---|---|---|---|---|
| | Concentration (wt. %) | Type | Viscosity (Pa·s) | after 1 day | after 1 week | after 2 weeks |
| Example 190D | 0.3 | S1' | 21.5 | ○ | ○ | ○ |
| Example 191D | 1 | S1' | 52.0 | ○ | ○ | ○ |
| Example 192D | 5 | S1' | 120 | ○ | ○ | ○ |
| Comparative Example 129D | 0.1 | S1' | 8.5 | x | x | x |
| Comparative Example 130D | 8 | S1' | unpreparable | — | — | — |
| Example 193D | 0.3 | S2' | 22.5 | ○ | ○ | ○ |
| Example 194D | 1 | S2' | 54.0 | ○ | ○ | ○ |
| Example 195D | 5 | S2' | 150 | ○ | ○ | ○ |
| Comparative Example 131D | 0.1 | S2' | 10.3 | x | x | x |
| Comparative Example 132D | 8 | S2' | unpreparable | — | — | — |
| Example 196D | 0.3 | S3' | 20.0 | ○ | ○ | ○ |
| Example 197D | 1 | S3' | 48.0 | ○ | ○ | ○ |
| Example 198D | 5 | S3' | 110 | ○ | ○ | ○ |
| Comparative Example 133D | 0.1 | S3' | 4.5 | x | x | x |
| Comparative Example 134D | 8 | S3' | unpreparable | — | — | — |

TABLE 35

[Isopropanol (organic acid 2) added (amount 33.0% by weight)]

| | Cellulose Fibers | | | State of Gel | | |
|---|---|---|---|---|---|---|
| | Concentration (wt. %) | Type | Viscosity (Pa·s) | after 1 day | after 1 week | after 2 weeks |
| Example 199D | 1 | S1' | 40.0 | ○ | ○ | ○ |
| Example 200D | 1 | S2' | 48.0 | ○ | ○ | ○ |
| Example 201D | 1 | S3' | 38.0 | ○ | ○ | ○ |

TABLE 36

[D-limonene (fragrance, deodorant 1) added (amount 0.2% by weight)]

| | Cellulose Fibers | | | State of Gel | | |
|---|---|---|---|---|---|---|
| | Concentration (wt. %) | Type | Viscosity (Pa·s) | after 1 day | after 1 week | after 2 weeks |
| Example 202D | 0.3 | S1' | 24.0 | ○ | ○ | ○ |
| Example 203D | 1 | S1' | 58.0 | ○ | ○ | ○ |
| Example 204D | 5 | S1' | 120 | ○ | ○ | ○ |
| Comparative Example 135D | 0.1 | S1' | 10.5 | x | x | x |
| Comparative Example 136D | 8 | S1' | unpreparable | — | — | — |
| Example 205D | 0.3 | S2' | 28.0 | ○ | ○ | ○ |
| Example 206D | 1 | S2' | 60.0 | ○ | ○ | ○ |
| Example 207D | 5 | S2' | 150 | ○ | ○ | ○ |
| Comparative Example 137D | 0.1 | S2' | 12.5 | x | x | x |
| Comparative Example 138D | 8 | S2' | unpreparable | — | — | — |
| Example 208D | 0.3 | S3' | 21.0 | ○ | ○ | ○ |
| Example 209D | 1 | S3' | 55.0 | ○ | ○ | ○ |
| Example 210D | 5 | S3' | 110 | ○ | ○ | ○ |

TABLE 36-continued

[D-limonene (fragrance, deodorant 1) added (amount 0.2% by weight)]

| | Cellulose Fibers | | | State of Gel | | |
|---|---|---|---|---|---|---|
| | Concentration (wt. %) | Type | Viscosity (Pa · s) | after 1 day | after 1 week | after 2 weeks |
| Comparative Example 139D | 0.1 | S3' | 9.8 | x | x | x |
| Comparative Example 140D | 8 | S3' | unpreparable | — | — | — |
| Comparative Example 141D | 1 | H1' | 30.5 | separated | — | — |
| Comparative Example 142D | 1 | H2' | 20.5 | ○ | x | x |

TABLE 37

[D-limonene (fragrance, deodorant 1) added (amount 2.0% by weight)]

| | Cellulose Fibers | | | State of Gel | | |
|---|---|---|---|---|---|---|
| | Concentration (wt. %) | Type | Viscosity (Pa · s) | after 1 day | after 1 week | after 2 weeks |
| Example 211D | 0.3 | S1' | 24.0 | ○ | ○ | ○ |
| Example 212D | 1 | S1' | 46.0 | ○ | ○ | ○ |
| Example 213D | 5 | S1' | 110 | ○ | ○ | ○ |
| Comparative Example 143D | 0.1 | S1' | 9.5 | x | x | x |
| Comparative Example 144D | 8 | S1' | unpreparable | — | — | — |
| Example 214D | 0.3 | S2' | 28.0 | ○ | ○ | ○ |
| Example 215D | 1 | S2' | 55.5 | ○ | ○ | ○ |
| Example 216D | 5 | S2' | 130 | ○ | ○ | ○ |
| Comparative Example 145D | 0.1 | S2' | 11.5 | x | x | x |
| Comparative Example 146D | 8 | S2' | unpreparable | — | — | — |
| Example 217D | 0.3 | S3' | 20.0 | ○ | ○ | ○ |
| Example 218D | 1 | S3' | 43.0 | ○ | ○ | ○ |
| Example 219D | 5 | S3' | 95 | ○ | ○ | ○ |
| Comparative Example 147D | 0.1 | S3' | 6.0 | x | x | x |
| Comparative Example 148D | 8 | S3' | unpreparable | — | — | — |

TABLE 38

[Orange oil (fragrance, deodorant 2) added (amount 2.0% by weight)]

| | Cellulose Fibers | | | State of Gel | | |
|---|---|---|---|---|---|---|
| | Concentration (wt. %) | Type | Viscosity (Pa · s) | after 1 day | after 1 week | after 2 weeks |
| Example 220D | 1 | S1' | 40.0 | ○ | ○ | ○ |
| Example 221D | 1 | S2' | 45.0 | ○ | ○ | ○ |
| Example 222D | 1 | S3' | 38.0 | ○ | ○ | ○ |

TABLE 39

| | Functional Additive | | Cellulose Fibers | | | State of Gel | | |
|---|---|---|---|---|---|---|---|---|
| | Concentration (wt. %) | Type | Concentration (wt. %) | Type | Viscosity (Pa · s) | after 1 day | after 1 week | after 2 weeks |
| Blank | — | — | 1.5 | A1' | 31.0 | ○ | ○ | ○ |
| Conventional Example 1D | 0.10 | NaCl | 1.5 | A1' | 0.9 | x | x | x |
| Conventional Example 2D | 1.00 | | 1.5 | A1' | — | separated | separated | separated |
| Conventional Example 3D | 0.05 | KCl | 1.5 | A1' | 4.5 | x | x | x |
| Conventional Example 4D | 0.10 | | 1.5 | A1' | 1.3 | x | x | x |
| Conventional Example 5D | 0.05 | CaCl$_2$ | 1.5 | A1' | 1.2 | x | x | x |
| Conventional Example 6D | 0.10 | | 1.5 | A1' | 1.2 | x | x | x |
| Conventional Example 7D | 0.05 | MgCl$_2$ | 1.5 | A1' | 1.1 | x | x | x |
| Conventional Example 8D | 0.10 | | 1.5 | A1' | 0.9 | x | x | x |
| Conventional Example 9D | 0.05 | (NH$_4$)$_2$SO$_4$ | 1.5 | A1' | 2.0 | x | x | x |
| Conventional Example 10D | 0.10 | | 1.5 | A1' | 1.5 | x | x | x |
| Conventional Example 11D | 0.05 | Na$_2$CO$_3$ | 1.5 | A1' | 2.9 | x | x | x |
| Conventional Example 12D | 0.10 | | 1.5 | A1' | 1.7 | x | x | x |

TABLE 39-continued

| | Functional Additive | | Cellulose Fibers | | | State of Gel | | |
|---|---|---|---|---|---|---|---|---|
| | Concentration (wt. %) | Type | Concentration (wt. %) | Type | Viscosity (Pa · s) | after 1 day | after 1 week | after 2 weeks |
| Conventional Example 13D | 1.0 | Activator 1 | 1.5 | A1' | 30.5 | separated | separated | separated |
| Conventional Example 14D | 3.0 | | 1.5 | A1' | 21.0 | x | x | x |
| Conventional Example 15D | 1.0 | Activator 2 | 1.5 | A1' | 7.0 | x | x | x |
| Conventional Example 16D | 3.0 | | 1.5 | A1' | 1.2 | x | x | x |
| Conventional Example 17D | 1.0 | Activator 3 | 1.5 | A1' | 0.3 | x | x | x |
| Conventional Example 18D | 3.0 | | 1.5 | A1' | 0.1 | x | x | x |

TABLE 40

| | Functional Additive | | Cellulose Fibers | | | State of Gel | | |
|---|---|---|---|---|---|---|---|---|
| | Concentration (wt. %) | Type | Concentration (wt. %) | Type | Viscosity (Pa · s) | after 1 day | after 1 week | after 2 weeks |
| Blank | — | — | 1.5 | A1' | 31.0 | ○ | ○ | ○ |
| Conventional Example 19D | 10.0 | Oil 1 | 1.5 | A1' | 30.0 | ○ | separated | separated |
| Conventional Example 20D | 33.0 | | 1.5 | A1' | immeasurable | separated | separated | separated |
| Conventional Example 21D | 10.0 | Oil 2 | 1.5 | A1' | immeasurable | separated | separated | separated |
| Conventional Example 22D | 33.0 | | 1.5 | A1' | immeasurable | separated | separated | separated |
| Conventional Example 23D | 10.0 | Oil 3 | 1.5 | A1' | immeasurable | separated | separated | separated |
| Conventional Example 24D | 33.0 | | 1.5 | A1' | immeasurable | separated | separated | separated |
| Conventional Example 25D | 33.0 | Organic Solvent 1 | 1.5 | A1' | 3.8 | x | x | x |
| Conventional Example 26D | 10.0 | Organic Solvent 2 | 1.5 | A1' | 12.4 | x | x | x |
| Conventional Example 27D | 33.0 | | 1.5 | A1' | 1.8 | x | x | x |

TABLE 41

| | Functional Additive | | Carboxyl Polymer | | | State of Gel | | |
|---|---|---|---|---|---|---|---|---|
| | Concentration (wt. %) | Type | Concentration (wt. %) | Type | Viscosity (Pa · s) | after 1 day | after 1 week | after 2 weeks |
| Blank | — | — | 0.5 | A2' | 61.0 | ○ | ○ | ○ |
| Conventional Example 28D | 0.10 | NaCl | 0.5 | A2' | 9.5 | x | x | x |
| Conventional Example 29D | 1.00 | | 0.5 | A2' | 0.2 | x | x | x |
| Conventional Example 30D | 0.05 | KCl | 0.5 | A2' | 8.8 | x | x | x |
| Conventional Example 31D | 0.10 | | 0.5 | A2' | 0.2 | x | x | x |
| Conventional Example 32D | 0.05 | $CaCl_2$ | 0.5 | A2' | — | separated | separated | separated |
| Conventional Example 33D | 0.10 | | 0.5 | A2' | — | separated | separated | separated |
| Conventional Example 34D | 0.05 | $MgCl_2$ | 0.5 | A2' | immeasurable | separated | separated | separated |

TABLE 41-continued

| | Functional Additive | | Carboxyl Polymer | | | State of Gel | | |
|---|---|---|---|---|---|---|---|---|
| | Concentration (wt. %) | Type | Concentration (wt. %) | Type | Viscosity (Pa · s) | after 1 day | after 1 week | after 2 weeks |
| Conventional Example 35D | 0.10 | | 0.5 | A2' | immeasurable | separated | separated | separated |
| Conventional Example 36D | 0.05 | $(NH_4)_2SO_4$ | 0.5 | A2' | immeasurable | separated | separated | separated |
| Conventional Example 37D | 0.10 | | 0.5 | A2' | immeasurable | separated | separated | separated |
| Conventional Example 38D | 0.05 | $Na_2CO_3$ | 0.5 | A2' | immeasurable | separated | separated | separated |
| Conventional Example 39D | 0.10 | | 0.5 | A2' | immeasurable | separated | separated | separated |
| Conventional Example 40D | 1.0 | Activator 3 | 0.5 | A2' | immeasurable | separated | separated | separated |
| Conventional Example 41D | 3.0 | | 0.5 | A2' | immeasurable | separated | separated | separated |
| Conventional Example 42D | 10.0 | Oil 1 | 0.5 | A2' | immeasurable | separated | separated | separated |
| Conventional Example 43D | 33.0 | | 0.5 | A2' | immeasurable | separated | separated | separated |
| Conventional Example 44D | 10.0 | Oil 2 | 0.5 | A2' | immeasurable | separated | separated | separated |
| Conventional Example 45D | 33.0 | | 0.5 | A2' | immeasurable | separated | separated | separated |
| Conventional Example 46D | 10.0 | Oil 3 | 0.5 | A2' | immeasurable | separated | separated | separated |
| Conventional Example 47D | 33.0 | | 0.5 | A2' | immeasurable | separated | separated | separated |
| Conventional Example 48D | 2.0 | Inorganic Fine particles 1 | 0.5 | A2' | immeasurable | separated | separated | separated |
| Conventional Example 49D | 20.0 | | 0.5 | A2' | immeasurable | separated | separated | separated |
| Conventional Example 50D | 2.0 | Inorganic Fine particles 2 | 0.5 | A2' | immeasurable | separated | separated | separated |
| Conventional Example 51D | 20.0 | | 0.5 | A2' | immeasurable | separated | separated | separated |

Thus obtained, the samples (compositions) were evaluated for the properties thereof according to the same criteria as mentioned above. The results are shown in the above Table 8 to Table 41.

From the results in the above Table 8 to Table 41, it is known that the compositions of Examples, in which any of the cellulose fibers S1' to S3' having an aldehyde group content of from 0.08 to 0.3 mmol/g and a carboxyl group content of from 0.6 to 2.0 mmol/g were used and in which the content of the cellulose fibers was from 0.3 to 5.0% by weight, kept gel and their viscosity reduction was small even when various functional additives (inorganic salts, etc.) were added thereto. However, the conventional compositions separated or could not keep gel as their viscosity reduction was great when various functional additives were added thereto.

As opposed to these, the compositions of Comparative Examples, in which any of the cellulose fibers S1' to S3' having an aldehyde group content of from 0.08 to 0.3 mmol/g and a carboxyl group content of from 0.6 to 2.0 mmol/g were used but in which the content of the cellulose fibers was lower than the lower limit (0.3% by weight), could not keep gel after one day. The compositions of Comparative Examples, in which any of the cellulose fibers S1' to S3' having an aldehyde group content of from 0.08 to 0.3 mmol/g and a carboxyl group content of from 0.6 to 2.0 mmol/g were used but in which the content of the cellulose fibers was more than the upper limit (5.0% by weight), could not be macroscopically homogeneous gel-type compositions.

In the compositions of Comparative Examples using the cellulose fibers H1' having a carboxyl group content of less than 0.6 mmol/g, the cellulose fibers partly separated and settled out to form macroscopically nonhomogeneous gel. The compositions of Comparative Examples using the cellulose fibers H2' having a carboxyl group content of more than 2.0 mmol/g became flowable with time, and after 2 days, the composition could not keep gel.

[Examples of Spray Composition]

Next described are Examples of the spray composition along with Comparative Examples. However, the present invention (spray composition) should not be limited to these Examples.

Prior to Examples and Comparative Examples, cellulose fibers S1" to S3" for Examples and cellulose fibers H1" and H2" for Comparative Examples were prepared as follows.

[Production of Cellulose Fibers S1" (for Examples)]

(1) Oxidation Step

Undried sulfite-bleached soft wood pulp (mainly including fibers having a fiber size of more than 1000 nm) in an amount corresponding to 200 g of the dry weight thereof, and 2.5 g of TEMPO and 25 g of sodium bromide were dispersed in 1000 ml of water, and an aqueous 13 wt. % sodium hypochlorite solution was added thereto so that the amount of sodium hypochlorite could be 5.4 mmol relative to 100 g of the pulp, and the reaction was started. During the reaction, an aqueous 0.5 M sodium hydroxide solution was kept dropwise added thereto to keep the pH at from 10 to 11, and at the time when no pH change could be seen, the reaction was considered to have ended (reaction time, 120 minutes).

(2) Purification Step

The reaction product was filtered through a glass filter, washed with a sufficient amount of ion-exchanged water and filtered, and the electric conductivity of the resulting filtrate was measured. At the time when there could be seen no electric conductivity change of the filtrate after repeated washing with water, the purification step was finished. In that manner, water-infiltrated reaction product fibers having a solid content of 20% by weight were produced.

(3) Dispersion Step (Fibrillation Step)

Water was added to the reaction product fibers to prepare a 2.0 wt. % slurry, and using an ultrahigh-pressure homogenizer (Microfluidizer, Model M-110-E/H, by Mizuho Industry), followed by processing twice under an operation pressure of $1.72 \times 10^8$ Pa, thereby giving fibrillated cellulose fibers S1".

[Production of Cellulose Fibers S2" and S3" (for Examples), and Cellulose Fibers H1" and H2" (for Comparative Examples)]

Cellulose fibers S2" and S3" (for Examples) and H1" and H2" (for Comparative Examples) were produced in the same manner as that for the production of the cellulose fibers S1" except that the amount of sodium hypochlorite to be added and the reaction time were changed as in the following Table 42.

TABLE 42

| | Cellulose Fibers | | | | |
| --- | --- | --- | --- | --- | --- |
| | for Examples | | | for Comparative Examples | |
| | S1" | S2" | S3" | H1" | H2" |
| Amount of sodium hypochlorite (mmol/g) | 5.4 | 4.2 | 11.9 | 3.4 | 15.2 |
| Reaction time (min) | 120 | 120 | 120 | 120 | 180 |
| Amount of carboxyl group (mmol/g) | 1.00 | 0.82 | 1.72 | 0.50 | 2.10 |
| Amount of aldehyde group (mmol/g) | 0.18 | 0.23 | 0.05 | 0.36 | 0.03 |
| Sum total of amount of carboxyl group and amount of aldehyde group (mmol/g) | 1.18 | 1.05 | 1.77 | 0.86 | 2.13 |
| Maximum Fiber Diameter (nm) | 10 | 12 | 10 | 35 | 10 |
| Number-Average Fiber Diameter (nm) | 7 | 7 | 6 | 15 | 6 |

Thus obtained the cellulose fibers S1" to S3" and H1" and H2" were analyzed for the following items, according to the criteria mentioned below. The results are shown in the above Table 42.

[Maximum Fiber Diameter, Number-Average Fiber Diameter]

Through TEM observation, the maximum fiber diameter and the number-average fiber diameter of the cellulose fibers were determined Briefly, the cellulose fibers were cast onto a hydrophilicated carbon film-coated grid, and stained with 2% uranyl acetate. On the stained negative TEM image of the sample, the fibers were analyzed.

[Determination of Amount of Carboxyl Group]

After preparing 60 ml of a 2.0 wt. % slurry of the cellulose fibers, its pH was made about 2.5 with an aqueous 0.1 M hydrochloric acid solution added thereto. Subsequently, an aqueous 0.05 M sodium hydroxide solution was dropwise added thereto, and its electric conductivity was measured. The measurement was continued until the pH could reach about 11. From the amount of sodium hydroxide (V) consumed in the neutralization stage of the weak acid having a gentle change of electric conductivity, the amount (a) of the functional group (the amount of the carboxyl group) was calculated according to the following formula (2).

[Numerical Formula 4]

$$\text{Amount of Functional Group (mmol/g)} = V \text{ (ml)} \times 0.05 / (\text{mass of cellulose, g}) \qquad (2)$$

[Measurement of Amount of Aldehyde Group]

The cellulose fibers were further oxidized in an aqueous 2 wt. % sodium hypochlorite solution, which had been controlled to have a pH of from 4 to 5 with acetic acid, for 48 hours at room temperature (25° C.). It was again neutralized, and from the amount (V) of sodium hydroxide consumed in the neutralization, the amount (b) of the functional group was determined according to the above formula (2). With that, the amount of the functional group added by this oxidation [(b)−(a)] was calculated, and this is the amount of the aldehyde group.

[Confirmation of Crystal Structure, Carboxyl Group and Aldehyde Group]

A part of the slurry was dried to give a transparent cellulose film, and the wide-angle X-ray diffraction image of the film confirmed the presence of the cellulose I-type crystal structure in all the cellulose fibers S1" to S3" and H1" and H2". In addition, in the attenuated total IR reflectiometry (ATR) of the sample, the presence of carbonyl group-caused absorption (at around 1608 $cm^{-1}$) and acid-type carboxyl group (COOH)-caused absorption (at around 1730 $cm^{-1}$) in all these cellulose fibers was confirmed.

[Confirmation on $^{13}$C-NMR Chart]

As to whether or not the hydroxyl group alone at the C6-position in the glucose unit in the surface of the cellulose fibers was selectively oxidized into a carboxyl group, the sample was confirmed on the $^{13}$C-NMR chart thereof. Specifically, the peak at 62 ppm corresponding to the C6-position of the primary hydroxyl group of the glucose unit, as confirmed on the $^{13}$C-NMR chart of the cellulose before oxidation, disappeared after the oxidation, and in place of it, a peak derived from the carboxyl group appeared at 178 ppm. From this, it was confirmed that, in the cellulose fibers S1" to S3", the C6-position hydroxyl group alone of the glucose unit was oxidized into an aldehyde group and a carboxyl group.

[Production of Cellulose Fine Particles (for Comparative Examples)]

According to Example 1 described in JP-A 2003-73229, cellulose fine particles were produced. Specifically, a starting pulp having a mean degree of polymerization (DP) of 760, as prepared by cutting a pure pulp sheet into chips of 5 mm×5 mm, was dissolved in an aqueous 65 wt. % sulfuric acid solution at −5° C. in such a manner that the cellulose concentration could be 5% by weight to prepare a transparent and viscous cellulose dope. The cellulose dope was poured into water (5° C.) in an amount of 2.5 times by weight of the dope with stirring to prepare a suspension of solid cellulose flocs. The suspension was hydrolyzed at 85° C. for 20 minutes, then the dispersion medium of the aqueous sulfuric acid solution was removed by filtration under reduced pressure through a glass filter. This was fully washed with water repeatedly many times until the pH of the wash waste could reach about 3, then washed (neutralized) with an aqueous dilute ammonia solution at a pH of about 11, and further washed with ion-exchanged water to prepare a semitransparent white gel having a cellulose concentration of 6.0% by weight. Thus obtained, the gel was diluted with water to have a cellulose concentration of 4.0% by weight, and dispersed with a homomixer (T.K. Robomix by Primix) at a number of revolutions of 15000 rpm for 10 minutes, and then processed five times with an ultrahigh-pressure homogenizer (Microfluidizer Model M-110-E/H, by Mizuho Industry) under an operation pressure of $1.72 \times 10^8$ Pa to prepare a highly-transparent cellulose (aqueous dispersion of cellulose fine particles) (pH=6.7).

Examples 1E to 9E, Comparative Examples 1E to 11E

First, the cellulose fibers S1" to S3" and H1" and H2" (cellulose fibers for Examples and Comparative Examples) produced in the above were prepared as a thickener. In addition, the cellulose fine particles produced in the above, as well as a carboxyvinyl polymer (Carbopol 980, sold by Chugai Trade), a polyacrylamide (having a mean molecular weight of from 9,000,000 to 10,000,000, by Kishida Chemical), and synthetic smectite fine particles (Smecton SA, by Kunimine Industry) were also prepared. Ion-exchanged water alone was added to the thickener to prepare samples having a concentration of 0.5% by weight, 1.0% by weight or 1.5% by weight (see Table 43). The carboxyvinyl polymer solution (Comparative Examples 6E, 7E) was, after the carboxyvinyl polymer had been dissolved therein, neutralized with dilute ammonia water. Each sample prepared as above was dispersed with a homomixer (T.K. Robomix, by Primix) at a number of revolutions of 15000 rpm for 10 minutes to prepare a spray composition.

By using a cone-plate type rotatory viscometer (Rheosol-G2000, by UBM), the spray composition thus produced as above was analyzed at 20° C. in a shear rate region including from $1 \times 10^{-3}$ $S^{-1}$ to $1 \times 10^3$ $S^{-1}$, and the maximum value ($\eta_{max}$) and the minimum value ($\eta_{min}$) of the viscosity thereof are shown in the following Table 43.

Each spray composition was charged in a commercially-available dispenser-type spray atomizer having a capacity of 50 ml (by SANPLATEC), and tested for the spraying characteristics (atomizability) thereof according to the following test method and criteria. The results are shown in the following Table 43.
<Test Method and Criteria>
[Gel State]
The spray atomizer filled with the composition was turned upside down, and the movement of the liquid surface was checked visually. The composition in which a part of the cellulose fibers or the functional additive had separated was expressed as "separated" in the Table.
x: When turned upside down, the liquid surface immediately moved greatly.
Δ: When turned upside down, the liquid surface moved slowly.
○: When turned upside down, the liquid surface did not move.
[Spray Condition]
Actually sprayed, the composition was checked for the spraying condition thereof
x: The composition was not jetted out through the nozzle and spraying was impossible; or the composition could be jetted out through the nozzle but could not be misty.
○: The composition was jetted out through the nozzle as a good mist.
[Spraying Unevenness]
A frosted glass plate of 18 cm×18 cm was stood vertically, and at a position spaced by 20 cm as the vertical distance therebetween, the spray atomizer was pushed once toward the glass plate, and immediately, the dispersion condition of the liquid droplets having adhered to the glass surface was observed. This was compared with a control case where ion-exchanged water alone was used as the mother liquid of spray.
x: Large droplets scattered, and obvious spraying unevenness was confirmed.
Δ: Large droplets were not seen, but as compared with the case of ion-exchanged water alone, the distribution of the droplets was rough.
○: Liquid droplets distributed densely on the same level as or on a higher level than that of the case of ion-exchanged water alone
[Dripping]
Under the same condition as that in evaluation of spraying unevenness, the spraying was repeated a few times and continued until liquid droplets could be sprayed on the vertical glass face densely with no space therebetween, and while the glass place was kept stood vertically, the sprayed surface was checked at every spraying for the presence or absence of dripping thereon.
x: In one spraying, dripping occurred.
Δ: In one spraying, dripping did not occur, but with the increase in the thickness of the sprayed liquid on the glass surface, dripping occurred.
○: In spraying multiple times, no dripping occurred.

TABLE 43

| | Thickener | Thickener Concentration | $\eta_{max}$ (mPa · s) | $\eta_{min}$ (mPa · s) | Gel State | Spray Condition | Spraying Unevenness | Dripping |
|---|---|---|---|---|---|---|---|---|
| Example 1E | cellulose fibers S1" | 0.5 wt. % | $2 \times 10^4$ | $2.4 \times 10^1$ | ○ | ○ | ○ | ○ |
| Example 2E | cellulose fibers S1" | 1.0 wt. % | $2 \times 10^5$ | $3.3 \times 10^1$ | ○ | ○ | ○ | ○ |
| Example 3E | cellulose fibers S1" | 1.5 wt. % | $8 \times 10^6$ | $5.6 \times 10^1$ | ○ | ○ | ○ | ○ |
| Example 4E | cellulose fibers S2" | 0.5 wt. % | $4 \times 10^4$ | $1.2 \times 10^1$ | ○ | ○ | ○ | ○ |
| Example 5E | cellulose fibers S2" | 1.0 wt. % | $5 \times 10^5$ | $2.7 \times 10^1$ | ○ | ○ | ○ | ○ |
| Example 6E | cellulose fibers S2" | 1.5 wt. % | $1 \times 10^7$ | $8.5 \times 10^1$ | ○ | ○ | ○ | ○ |
| Example 7E | cellulose fibers S3" | 0.5 wt. % | $2 \times 10^4$ | $2.7 \times 10^1$ | ○ | ○ | ○ | ○ |
| Example 8E | cellulose fibers S3" | 1.0 wt. % | $2 \times 10^5$ | $3.1 \times 10^1$ | ○ | ○ | ○ | ○ |

TABLE 43-continued

| | Thickener | Thickener Concentration | $\eta_{max}$ (mPa·s) | $\eta_{min}$ (mPa·s) | Gel State | Spray Condition | Spraying Unevenness | Dripping |
|---|---|---|---|---|---|---|---|---|
| Example 9E | cellulose fibers S3" | 1.5 wt. % | $9 \times 10^6$ | $8.0 \times 10^1$ | ○ | ○ | ○ | ○ |
| Comparative Example 1E | cellulose fibers H1" | 0.5 wt. % | $3 \times 10^3$ | $1.8 \times 10^2$ | separated | x | Δ | ○ |
| Comparative Example 2E | cellulose fibers H1" | 1.5 wt. % | $5 \times 10^6$ | $5.8 \times 10^2$ | separated | x | Δ | ○ |
| Comparative Example 3E | cellulose fibers H2" | 0.5 wt. % | $4 \times 10^3$ | $1.5 \times 10^2$ | x | ○ | Δ | x |
| Comparative Example 4E | cellulose fibers H2" | 1.5 wt. % | $3 \times 10^6$ | $3.8 \times 10^2$ | ○ | x | Δ | Δ |
| Comparative Example 5E | cellulose fine particles | 0.5 wt. % | $2 \times 10^3$ | $1.1 \times 10^1$ | x | ○ | ○ | Δ |
| Comparative Example 6E | Carboxyvinyl polymer | 0.5 wt. % | $3 \times 10^6$ | $6.8 \times 10^2$ | ○ | x | — | — |
| Comparative Example 7E | Carboxyvinyl polymer | 1.5 wt. % | $1 \times 10^7$ | $4.3 \times 10^3$ | ○ | x | — | — |
| Comparative Example 8E | polyacrylamide | 0.5 wt. % | $4 \times 10^3$ | $1.5 \times 10^2$ | x | Δ | x | x |
| Comparative Example 9E | polyacrylamide | 1.5 wt. % | $4 \times 10^4$ | $8.9 \times 10^2$ | Δ | x | — | — |
| Comparative Example 10E | synthetic smectite fine particles | 0.5 wt. % | $3 \times 10^3$ | $2.4 \times 10^1$ | Δ | ○ | ○ | x |
| Comparative Example 11E | synthetic smectite fine particles | 1.5 wt. % | $1 \times 10^6$ | $3.6 \times 10^1$ | ○ | ○ | ○ | x |

As obvious from the results in the above Table, it is known that the spray compositions of Examples 1E to 9E showed a good gel state and good spray characteristics. As opposed to these, in the spray compositions of Comparative Examples 1E to 2E, a part of cellulose settled out. Therefore, during spraying, the nozzle clogged and spraying became impossible. The spray compositions of Comparative Examples 3E to 5E were disadvantageous in that the gel state thereof was poor and the sprayed composition could not form a mist. Of the compositions of Comparative Examples 6E to 9E in which carboxyvinyl polymer or polyacrylamide was used as a thickener, the spray characteristics were bad, and it is known that the viscous liquid of those Comparative Examples is unsuitable as a spray composition. Although the compositions of Comparative Examples 10E to 11E in which synthetic smectite fine particles were used as the thickener had good gel characteristics and spray characteristics, they were problematic in that they drip when their concentration is low as in these cases and there was the problem of the compositions of the type is that their concentration must be high.

Examples 10E to 27E, Comparative Examples 12E to 29E

First, the thickeners (cellulose fibers S1" to S3" and H1" and H2", and cellulose fine particles) used in the above-mentioned Examples and Comparative Examples were prepared. Ion-exchanged water, and inorganic salt/electrolyte (any of sodium chloride, sodium edetate, sodium ascorbate) as in the combination shown in the following Table 44 to Table 46 were added to each thickener to prepare a sample having a thickener concentration of 0.5% by weight, 1.0% by weight or 1.5% by weight (see Table 44 to Table 46), and an inorganic salt/electrolyte concentration of 0.1% by weight. Thus prepared, the sample was dispersed with a homomixer (T.K. Robomix, by Primix) at a number of revolutions of 15000 rpm for 10 minutes, thereby preparing a spray composition.

By using a cone-plate type rotatory viscometer (Rheosol-G2000, by UBM), the spray composition thus produced as above was analyzed at 20° C. in a shear rate region including from $1 \times 10^{-3}$ S$^1$ to $1 \times 10^3$ S$^{-1}$, and the maximum value ($\eta_{max}$) and the minimum value ($\eta_{min}$) of the viscosity thereof are shown in the following Table 44 to Table 46.

Each spray composition was charged in a commercially-available dispenser-type spray atomizer having a capacity of 50 ml (by SANPLATEC), and tested for the spraying characteristics (atomizability) thereof according to the test method and criteria indicated in the above-mentioned Examples 1E to 9E and Comparative Examples 1E to 11E. The results are shown in the following Table 44 to Table 46.

TABLE 44

| | Thickener | Inorganic Salt/ Electrolyte | Thickener Concentration | $\eta_{max}$ (mPa·s) | $\eta_{min}$ (mPa·s) | Gel State | Spray Condition | Spraying Unevenness | Dripping |
|---|---|---|---|---|---|---|---|---|---|
| Example 10E | cellulose fibers S1" | sodium chloride | 0.5 wt. % | $1.5 \times 10^4$ | $1.0 \times 10^1$ | ○ | ○ | ○ | ○ |
| Example 11E | cellulose fibers S1" | sodium chloride | 1.5 wt. % | $2 \times 10^6$ | $3.5 \times 10^1$ | ○ | ○ | ○ | ○ |
| Example 12E | cellulose fibers S2" | sodium chloride | 0.5 wt. % | $4 \times 10^4$ | $1.2 \times 10^1$ | ○ | ○ | ○ | ○ |

TABLE 44-continued

| | Thickener | Inorganic Salt/ Electrolyte | Thickener Concentration | $\eta_{max}$ (mPa · s) | $\eta_{min}$ (mPa · s) | Gel State | Spray Condition | Spraying Unevenness | Dripping |
|---|---|---|---|---|---|---|---|---|---|
| Example 13E | cellulose fibers S2" | sodium chloride | 1.5 wt. % | $8 \times 10^6$ | $3.8 \times 10^1$ | ○ | ○ | ○ | ○ |
| Example 14E | cellulose fibers S3" | sodium chloride | 0.5 wt. % | $2 \times 10^4$ | $1.1 \times 10^1$ | ○ | ○ | ○ | ○ |
| Example 15E | cellulose fibers S3" | sodium chloride | 1.5 wt. % | $7 \times 10^6$ | $3.5 \times 10^1$ | ○ | ○ | ○ | ○ |
| Comparative Example 12E | cellulose fibers H1" | sodium chloride | 0.5 wt. % | $1 \times 10^3$ | $1.0 \times 10^1$ | Separated | x | ○ | x |
| Comparative Example 13E | cellulose fibers H1" | sodium chloride | 1.5 wt. % | $8 \times 10^5$ | $1.2 \times 10^2$ | Separated | x | Δ | Δ |
| Comparative Example 14E | cellulose fibers H2" | sodium chloride | 0.5 wt. % | $1 \times 10^3$ | $1.1 \times 10^1$ | x | ○ | ○ | x |
| Comparative Example 15E | cellulose fibers H2" | sodium chloride | 1.5 wt. % | $3 \times 10^5$ | $1.3 \times 10^2$ | Δ | x | Δ | Δ |
| Comparative Example 16E | cellulose fine particles | sodium chloride | 0.5 wt. % | $1 \times 10^2$ | $1.0 \times 10^1$ | x | ○ | ○ | x |
| Comparative Example 17E | cellulose fine particles | sodium chloride | 1.5 wt. % | $1 \times 10^2$ | $2.8 \times 10^1$ | x | ○ | ○ | x |

TABLE 45

| | Thickener | Inorganic Salt/ Electrolyte | Thickener Concentration | $\eta_{max}$ (mPa · s) | $\eta_{min}$ (mPa · s) | Gel State | Spray Condition | Spraying Unevenness | Dripping |
|---|---|---|---|---|---|---|---|---|---|
| Example 16E | cellulose fibers S1" | Na edetate | 0.5 wt. % | $2 \times 10^4$ | $1.2 \times 10^1$ | ○ | ○ | ○ | ○ |
| Example 17E | cellulose fibers S1" | Na edetate | 1.5 wt. % | $5 \times 10^6$ | $2.5 \times 10^1$ | ○ | ○ | ○ | ○ |
| Example 18E | cellulose fibers S2" | Na edetate | 0.5 wt. % | $3 \times 10^4$ | $1.1 \times 10^1$ | ○ | ○ | ○ | ○ |
| Example 19E | cellulose fibers S2" | Na edetate | 1.5 wt. % | $7 \times 10^6$ | $2.0 \times 10^1$ | ○ | ○ | ○ | ○ |
| Example 20E | cellulose fibers S3" | Na edetate | 0.5 wt. % | $1.5 \times 10^4$ | $1.0 \times 10^1$ | ○ | ○ | ○ | ○ |
| Example 21E | cellulose fibers S3" | Na edetate | 1.5 wt. % | $7 \times 10^6$ | $2.0 \times 10^1$ | ○ | ○ | ○ | ○ |
| Comparative Example 18E | cellulose fibers H1" | Na edetate | 0.5 wt. % | $2 \times 10^3$ | $1.2 \times 10^1$ | separated | x | ○ | x |
| Comparative Example 19E | cellulose fibers H1" | Na edetate | 1.5 wt. % | $4 \times 10^5$ | $1.5 \times 10^2$ | separated | x | Δ | Δ |
| Comparative Example 20E | cellulose fibers H2" | Na edetate | 0.5 wt. % | $1 \times 10^3$ | $1.6 \times 10^1$ | Δ | ○ | ○ | x |
| Comparative Example 21E | cellulose fibers H2" | Na edetate | 1.5 wt. % | $2 \times 10^5$ | $2.0 \times 10^2$ | ○ | ○ | Δ | x |
| Comparative Example 22E | cellulose fine particles | Na edetate | 0.5 wt. % | immeasurable | immeasurable | separated | ○ | x | x |
| Comparative Example 23E | cellulose fine particles | Na edetate | 1.5 wt. % | immeasurable | immeasurable | separated | ○ | x | Δ |

TABLE 46

| | Thickener | Inorganic Salt/ Electrolyte | Thickener Concentration | $\eta_{max}$ (mPa · s) | $\eta_{min}$ (mPa · s) | Gel State | Spray Condition | Spraying Unevenness | Dripping |
|---|---|---|---|---|---|---|---|---|---|
| Example 22E | cellulose fibers S1" | Na ascorbate | 0.5 wt. % | $3 \times 10^4$ | $1.1 \times 10^1$ | ○ | ○ | ○ | ○ |
| Example 23E | cellulose fibers S1" | Na ascorbate | 1.5 wt. % | $6 \times 10^6$ | $2.3 \times 10^1$ | ○ | ○ | ○ | ○ |
| Example 24E | cellulose fibers S2" | Na ascorbate | 0.5 wt. % | $2 \times 10^4$ | $1.2 \times 10^1$ | ○ | ○ | ○ | ○ |

TABLE 46-continued

|  | Thickener | Inorganic Salt/ Electrolyte | Thickener Concentration | $\eta_{max}$ (mPa·s) | $\eta_{min}$ (mPa·s) | Gel State | Spray Condition | Spraying Unevenness | Dripping |
|---|---|---|---|---|---|---|---|---|---|
| Example 25E | cellulose fibers S2" | Na ascorbate | 1.5 wt. % | $7 \times 10^6$ | $2.6 \times 10^1$ | ○ | ○ | ○ | ○ |
| Example 26E | cellulose fibers S3" | Na ascorbate | 0.5 wt. % | $1.5 \times 10^4$ | $1.1 \times 10^1$ | ○ | ○ | ○ | ○ |
| Example 27E | cellulose fibers S3" | Na ascorbate | 1.5 wt. % | $4 \times 10^6$ | $2.1 \times 10^1$ | ○ | ○ | ○ | ○ |
| Comparative Example 24E | cellulose fibers H1" | Na ascorbate | 0.5 wt. % | $1 \times 10^3$ | $1.8 \times 10^1$ | separated | x | ○ | x |
| Comparative Example 25E | cellulose fibers H1" | Na ascorbate | 1.5 wt. % | $4 \times 10^5$ | $2.0 \times 10^2$ | separated | x | Δ | Δ |
| Comparative Example 26E | cellulose fibers H2" | Na ascorbate | 0.5 wt. % | $2 \times 10^3$ | $2.1 \times 10^1$ | Δ | ○ | ○ | x |
| Comparative Example 27E | cellulose fibers H2" | Na ascorbate | 1.5 wt. % | $1 \times 10^5$ | $1.8 \times 10^2$ | ○ | ○ | Δ | x |
| Comparative Example 28E | cellulose fine particles | Na ascorbate | 0.5 wt. % | immeasurable | immeasurable | separated | ○ | x | x |
| Comparative Example 29E | cellulose fine particles | Na ascorbate | 1.5 wt. % | immeasurable | immeasurable | separated | ○ | x | Δ |

As obvious from the results in the above Tables, it is known that the spray compositions of Examples using any of the cellulose fibers S1" to S3" all showed a good gel state and good spray characteristics even though an inorganic salt or an electrolyte was added thereto. As opposed to these, of the spray compositions of Comparative Examples using the cellulose fibers H1" or H2" or the cellulose fine particles as the thickener, the viscosity greatly lowered owing to addition of the inorganic salt or the electrolyte thereto, and as a result, the compositions could hardly keep the gel state thereof (some separated). Though they could be sprayed, there occurred spraying unevenness or dripping. Some of them failed to be sprayed on the way as the flocs formed therein clogged the nozzle.

Examples 28E to 45E, Comparative Examples 30E to 46E

The thickeners (cellulose fibers S1" to S3" and H1" and H2", and cellulose fine particles) used in the above-mentioned Examples and Comparative Examples were prepared. Ion-exchanged water, and additive (any of ethanol, dimethylpolysiloxane, glyceryl trioctanoate) as in the combination shown in the following Table 47 to Table 49 were added to each thickener in such a manner that the concentration of the thickener could be as in the following Table 47 to Table 49. The sample thus prepared was dispersed with a homomixer (T.K. Robomix, by Primix) at a number of revolutions of 15000 rpm for 10 minutes, thereby preparing a spray composition.

Using a cone-plate type rotatory viscometer (Rheosol-G2000, by UBM), the spray composition thus produced as above was analyzed at 20° C. in a shear rate region including from $1 \times 10^{-3}$ S$^{-1}$ to $1 \times 10^3$ S$^{-1}$, and the maximum value ($\eta_{max}$) and the minimum value ($\eta_{min}$) of the viscosity thereof are shown in the following Table 47 to Table 49.

Each spray composition was charged in a commercially-available dispenser-type spray atomizer having a capacity of 50 ml (by SANPLATEC), and tested for the spraying characteristics thereof according to the test method and criteria indicated in the above-mentioned Examples 1E to 9E and Comparative Examples 1E to 11E. The results are shown in the following Table 47 to Table 49.

TABLE 47

|  | Thickener | Additive | Thickener Concentration | $\eta_{max}$ (mPa·s) | $\eta_{min}$ (mPa·s) | Gel State | Spray Condition | Spraying Unevenness | Dripping |
|---|---|---|---|---|---|---|---|---|---|
| Example 28E | cellulose fibers S1" | *1 | 0.5 wt. % | $4 \times 10^4$ | $1.0 \times 10^1$ | Δ | ○ | ○ | ○ |
| Example 29E | cellulose fibers S1" | *1 | 1.5 wt. % | $5 \times 10^5$ | $1.8 \times 10^1$ | ○ | ○ | ○ | ○ |
| Example 30E | cellulose fibers S2" | *1 | 0.5 wt. % | $4 \times 10^4$ | $1.0 \times 10^1$ | Δ | ○ | ○ | ○ |
| Example 31E | cellulose fibers S2" | *1 | 1.5 wt. % | $6 \times 10^5$ | $1.6 \times 10^1$ | ○ | ○ | ○ | ○ |
| Example 32E | cellulose fibers S3" | *1 | 0.5 wt. % | $1.5 \times 10^4$ | $1.0 \times 10^1$ | Δ | ○ | ○ | ○ |
| Example 33E | cellulose fibers S3" | *1 | 1.5 wt. % | $9 \times 10^4$ | $1.7 \times 10^1$ | ○ | ○ | ○ | ○ |
| Comparative Example 30E | cellulose fibers H1" | *1 | 0.5 wt. % | $1 \times 10^3$ | $1.0 \times 10^1$ | separated | x | ○ | x |
| Comparative Example 31E | cellulose fibers H1" | *1 | 1.5 wt. % | $8 \times 10^4$ | $1.6 \times 10^2$ | separated | x | Δ | x |
| Comparative Example 32E | cellulose fibers H2" | *1 | 0.5 wt. % | $1 \times 10^3$ | $1.0 \times 10^1$ | Δ | ○ | ○ | x |

TABLE 47-continued

|  | Thickener | Additive | Thickener Concentration | $\eta_{max}$ (mPa·s) | $\eta_{min}$ (mPa·s) | Gel State | Spray Condition | Spraying Unevenness | Dripping |
|---|---|---|---|---|---|---|---|---|---|
| Comparative Example 33E | cellulose fibers H2" | *1 | 1.5 wt. % | $6 \times 10^4$ | $1.1 \times 10^2$ | ○ | ○ | x | x |
| Comparative Example 34E | cellulose fine particles | *1 | 0.5 wt. % | $8 \times 10^2$ | $3.1 \times 10^1$ | x | ○ | x | x |
| Comparative Example 35E | cellulose fine particles | *1 | 1.5 wt. % | $4 \times 10^4$ | $1.0 \times 10^1$ | x | ○ | x | x |

*1: ethanol (ethanol concentration, 20% by weight of the entire composition)

TABLE 48

|  | Thickener | Additive | Thickener Concentration | $\eta_{max}$ (mPa·s) | $\eta_{min}$ (mPa·s) | Gel State | Spray Condition | Spraying Unevenness | Dripping |
|---|---|---|---|---|---|---|---|---|---|
| Example 34E | cellulose fibers S1" | *2 | 0.5 wt. % | $3 \times 10^4$ | $1.3 \times 10^1$ | ○ | ○ | ○ | ○ |
| Example 35E | cellulose fibers S1" | *2 | 1.5 wt. % | $2 \times 10^6$ | $1.8 \times 10^1$ | ○ | ○ | ○ | ○ |
| Example 36E | cellulose fibers S2" | *2 | 0.5 wt. % | $4 \times 10^4$ | $1.1 \times 10^1$ | ○ | ○ | ○ | ○ |
| Example 37E | cellulose fibers S2" | *2 | 1.5 wt. % | $5 \times 10^6$ | $1.8 \times 10^1$ | ○ | ○ | ○ | ○ |
| Example 38E | cellulose fibers S3" | *2 | 0.5 wt. % | $2 \times 10^4$ | $1.0 \times 10^1$ | ○ | ○ | ○ | ○ |
| Example 39E | cellulose fibers S3" | *2 | 1.5 wt. % | $4 \times 10^6$ | $1.5 \times 10^1$ | ○ | ○ | ○ | ○ |
| Comparative Example 36E | cellulose fibers H1" | *2 | 0.5 wt. % | $2 \times 10^3$ | $1.2 \times 10^1$ | separated | x | ○ | x |
| Comparative Example 37E | cellulose fibers H1" | *2 | 1.5 wt. % | $5 \times 10^5$ | $1.8 \times 10^1$ | separated | x | Δ | x |
| Comparative Example 38E | cellulose fibers H2" | *2 | 0.5 wt. % | $1 \times 10^3$ | $1.2 \times 10^1$ | x | ○ | ○ | x |
| Comparative Example 39E | cellulose fibers H2" | *2 | 1.5 wt. % | $4 \times 10^4$ | $2.5 \times 10^2$ | ○ | ○ | x | x |
| Comparative Example 40E | cellulose fine particles | *2 | 0.5 wt. % | $6 \times 10^2$ | $1.8 \times 10^1$ | x | ○ | Δ | x |
| Comparative Example 41E | cellulose fine particles | *2 | 1.5 wt. % | $2 \times 10^2$ | $3.6 \times 10^2$ | ○ | ○ | x | Δ |

*2: dimethylpolysiloxane (incorporated in a ratio of 10% by weight of the entire composition)

TABLE 49

|  | Thickener | Additive | Thickener Concentration | $\eta_{max}$ (mPa·s) | $\eta_{min}$ (mPa·s) | Gel State | Spray Condition | Spraying Unevenness | Dripping |
|---|---|---|---|---|---|---|---|---|---|
| Example 40E | cellulose fibers S1" | *3 | 0.5 wt. % | $4 \times 10^4$ | $1.0 \times 10^1$ | Δ | ○ | ○ | Δ |
| Example 41E | cellulose fibers S1" | *3 | 1.5 wt. % | $2 \times 10^6$ | $1.5 \times 10^1$ | ○ | ○ | ○ | ○ |
| Example 42E | cellulose fibers S2" | *3 | 0.5 wt. % | $3 \times 10^4$ | $1.2 \times 10^1$ | Δ | ○ | ○ | ○ |
| Example 43E | cellulose fibers S2" | *3 | 1.5 wt. % | $5 \times 10^6$ | $1.8 \times 10^1$ | ○ | ○ | ○ | ○ |
| Example 44E | cellulose fibers S3" | *3 | 0.5 wt. % | $2 \times 10^4$ | $1.0 \times 10^1$ | ○ | ○ | ○ | ○ |
| Example 45E | cellulose fibers S3" | *3 | 1.5 wt. % | $5 \times 10^6$ | $1.6 \times 10^1$ | ○ | ○ | ○ | ○ |
| Comparative Example 42E | cellulose fibers H1" | *3 | 0.5 wt. % | $8 \times 10^2$ | $1.8 \times 10^1$ | separated | x | ○ | x |
| Comparative Example 43E | cellulose fibers H1" | *3 | 1.5 wt. % | $2 \times 10^5$ | $1.6 \times 10^2$ | separated | x | Δ | x |
| Comparative Example 44E | cellulose fibers H2" | *3 | 0.5 wt. % | $6 \times 10^2$ | $3.6 \times 10^1$ | x | ○ | ○ | x |

TABLE 49-continued

| | Thickener | Additive | Thickener Concentration | $\eta_{max}$ (mPa·s) | $\eta_{min}$ (mPa·s) | Gel State | Spray Condition | Spraying Unevenness | Dripping |
|---|---|---|---|---|---|---|---|---|---|
| Comparative Example 45E | cellulose fine particles | *3 | 0.5 wt. % | immeasurable | immeasurable | separated | ○ | x | x |
| Comparative Example 46E | cellulose fine particles | *3 | 1.5 wt. % | immeasurable | immeasurable | separated | ○ | x | x |

*3 glyceryl trioctanoate (incorporated in a ratio of 10% by weight of the entire composition)

As obvious from the results in the above Tables, it is known that, though their viscosity somewhat lowered owing to addition of the oil or the alcohol thereto, the spray compositions of Examples using any of the cellulose fibers S1" to S3" all showed a good gel state and good spray characteristics by somewhat increasing the amount of the cellulose fibers therein. As opposed to these, of the spray compositions of Comparative Examples using the cellulose fibers H1" or H2" or the cellulose fine particles as the thickener, the viscosity greatly lowered owing to addition of the oil or the alcohol, and as a result, the compositions could hardly keep the gel state thereof (some separated). Regarding the spray characteristics of the compositions, there occurred remarkable spraying unevenness or dripping. Some of them failed to be sprayed on the way as the flocs formed therein clogged the nozzle.

Examples 46E to 51E, Comparative Examples 47E to 52E

The thickeners (cellulose fibers S1" to S3" and H1" and H2", and cellulose fine particles) used in the above-mentioned Examples and Comparative Examples were prepared. Ion-exchanged water, and as an additive, titanium oxide (TTO-V3, by Ishihara Sangyo) were added to each thickener in such a manner that the concentration of the thickener could be as in the following Table 50, and that the titanium oxide concentration could be 0.1% by weight. The sample thus prepared was dispersed with a homomixer (T.K. Robomix, by Primix) at a number of revolutions of 15000 rpm for 10 minutes, thereby preparing a spray composition.

Using a cone-plate type rotatory viscometer (Rheosol-G2000, by UBM), the spray composition thus produced as above was analyzed at 20° C. in a shear rate region including from $1 \times 10^{-3}$ $S^{-1}$ to $1 \times 10^3$ $S^{-1}$, and the maximum value ($\eta_{max}$) and the minimum value ($\eta_{min}$) of the viscosity thereof are shown in the following Table 50.

Each spray composition was charged in a commercially-available dispenser-type spray atomizer having a capacity of 50 ml (by SANPLATEC), and tested for the spraying characteristics thereof according to the test method and criteria indicated in the above-mentioned Examples 1E to 9E and Comparative Examples 1E to 11E. The results are shown in the following Table 50.

TABLE 50

| | Thickener | Additive | Thickener Concentration | $\eta_{max}$ (mPa·s) | $\eta_{min}$ (mPa·s) | Gel State | Spray Condition | Spraying Unevenness | Dripping |
|---|---|---|---|---|---|---|---|---|---|
| Example 46E | cellulose fibers S1" | titanium oxide | 0.5 wt. % | $3 \times 10^4$ | $1.8 \times 10^1$ | ○ | ○ | ○ | ○ |
| Example 47E | cellulose fibers S1" | titanium oxide | 1.5 wt. % | $1 \times 10^7$ | $3.6 \times 10^1$ | ○ | ○ | ○ | ○ |
| Example 48E | cellulose fibers S2" | titanium oxide | 0.5 wt. % | $4 \times 10^4$ | $2.2 \times 10^1$ | ○ | ○ | ○ | ○ |
| Example 49E | cellulose fibers S2" | titanium oxide | 1.5 wt. % | $3 \times 10^7$ | $5.6 \times 10^1$ | ○ | ○ | ○ | ○ |
| Example 50E | cellulose fibers S3" | titanium oxide | 0.5 wt. % | $1 \times 10^4$ | $1.7 \times 10^1$ | ○ | ○ | ○ | ○ |
| Example 51E | cellulose fibers S3" | titanium oxide | 1.5 wt. % | $2 \times 10^7$ | $7.6 \times 10^1$ | ○ | ○ | ○ | ○ |
| Comparative Example 47E | cellulose fibers H1" | titanium oxide | 0.5 wt. % | $2 \times 10^4$ | $9.5 \times 10^1$ | separated | x | Δ | Δ |
| Comparative Example 48E | cellulose fibers H1" | titanium oxide | 1.5 wt. % | $8 \times 10^6$ | $2.3 \times 10^2$ | separated | x | Δ | Δ |
| Comparative Example 49E | cellulose fibers H2" | titanium oxide | 0.5 wt. % | $1 \times 10^4$ | $7.8 \times 10^1$ | ○ | ○ | x | Δ |
| Comparative Example 50E | cellulose fibers H2" | titanium oxide | 1.5 wt. % | $6 \times 10^6$ | $1.3 \times 10^2$ | ○ | ○ | x | Δ |
| Comparative Example 51E | cellulose fine particles | titanium oxide | 0.5 wt. % | immeasurable | immeasurable | separated | ○ | x | Δ |
| Comparative Example 52E | cellulose fine particles | titanium oxide | 1.5 wt. % | immeasurable | immeasurable | separated | ○ | x | ○ |

As obvious from the results in the above Table, it is known that, though their viscosity somewhat lowered owing to addition of titanium oxide thereto, the spray compositions of Examples using any of the cellulose fibers S1" to S3" all showed a good gel state and good spray characteristics by somewhat increasing the amount of the cellulose fibers therein. As opposed to these, the spray compositions of Comparative Examples using the cellulose fibers H1" or H2" or the cellulose fine particles as the thickener separated while releasing water in the upper part thereof, though they kept gel. In addition, regarding the spray characteristics of the compositions, spraying unevenness that would be caused by separation was remarkably observed.

INDUSTRIAL APPLICABILITY

The viscous composition of the present invention is usable as a cosmetic composition, a gel-type composition, a spray composition, etc. The cosmetic composition can be used in various applications of, for example, skincare cosmetics such as face lotion, emulsion, cold cream, vanishing cream, massage cream, emollient cream, cleansing cream, beauty essence, pack, foundation, sunscreen cosmetic, suntanning cosmetic, moisture cream, hand cream, skin-whitening emulsion, various lotions, etc.; hair-care cosmetics such as shampoo, rinse, hair conditioner, rinse-in shampoo, hair-styling agent (hair foam, gel-type hair dressing, etc.), hair treatment agent (hair cream, treatment lotion, etc.), hair dye, lotion-type hair-growing agent, hair tonic, etc.; cleaning agents such as hand cleaner, etc.; as well as pre-shaving lotion, after-shaving lotion, air freshener, dentifrice, ointment, adhesive patch, etc.

The gel-type composition uses cellulose fibers of a natural material and is rich in compatibility with various functional additives. Therefore, it is favorably and widely used for cosmetic bases and bases of toiletries such as air refreshers, etc.

The spray composition is gel and uses a natural material as the thickener therein, and the composition is rich in compatibility with various functional additives. Therefore, it is favorably and widely used for spray-type cosmetics and bases of toiletries such as spray-type air refreshers, etc.

The invention claimed is:

1. A viscous gel composition containing components (A') and (B):
   (A') cellulose fibers having a maximum fiber diameter of 1000 nm or less and a number-average fiber diameter of from 2 to 150 nm, wherein the cellulose has a cellulose I-type crystal structure; the hydroxyl group at the C6-position of the glucose unit in the cellulose molecule is selectively oxidized and modified into an aldehyde group and a carboxyl group; and the amount of the aldehyde group is from 0.08 to 0.3 mmol/g and the amount of the carboxyl group is from 0.6 to 2.0 mmol/g, and
   (B) water, wherein the content of component (A') is within a range of from 0.3 to 5.0% by weight of the entire gel composition.

2. The viscous gel composition according to claim 1, wherein the cellulose fibers of component (A') are prepared by oxidizing a portion of the hydroxyl groups of the cellulose fibers into a carboxyl group and an aldehyde group by the use of a co-oxidizing agent in the presence of an N-oxyl compound.

3. The viscous gel composition according to claim 1, further comprising a functional additive (C').

4. The viscous gel composition according to claim 3, wherein the functional additive (C') is at least one selected from inorganic salts, surfactants, oils, moisturizers, antiseptics, organic fine particles, inorganic fine particles, deodorants, fragrances and organic solvents.

* * * * *